US008026344B2

(12) United States Patent
Zhou et al.

(10) Patent No.: US 8,026,344 B2
(45) Date of Patent: Sep. 27, 2011

(54) TARGETED BINDING AGENTS DIRECTED TO UPAR AND USES THEREOF

(75) Inventors: Qing Zhou, Fremont, CA (US); Stephen Charles Emery, Macclesfield (GB); Paul Elvin, Macclesfield (GB)

(73) Assignee: MedImmune Limited, Cambridge (GB)

( * ) Notice: Subject to any disclaimer, the term of this patent is extended or adjusted under 35 U.S.C. 154(b) by 537 days.

(21) Appl. No.: 11/733,157

(22) Filed: Apr. 9, 2007

(65) Prior Publication Data

US 2008/0152587 A1    Jun. 26, 2008

Related U.S. Application Data

(60) Provisional application No. 60/790,642, filed on Apr. 10, 2006.

(51) Int. Cl.
*C07K 16/00* (2006.01)
*C07K 16/46* (2006.01)
*C07K 16/24* (2006.01)
*A61K 39/395* (2006.01)

(52) U.S. Cl. ............. 530/388.23; 530/387.1; 530/387.3; 530/388.1; 530/388.15; 424/130.1; 424/134.1; 424/141.1; 424/145.1; 424/142.1

(58) Field of Classification Search .................. None
See application file for complete search history.

(56) References Cited

U.S. PATENT DOCUMENTS 5,519,120 A * 5/1996 Dano et al. ............... 530/388.22
6,113,897 A    9/2000 Dano et al.

FOREIGN PATENT DOCUMENTS

| EP | 1013285 | 6/2000 |
|---|---|---|
| WO | WO03/09808 | 5/1993 |
| WO | WO06/094828 | 9/2006 |

OTHER PUBLICATIONS

Rudikoff et al. Proc Natl Acad Sci USA 1982 vol. 79 p. 1979.*
Pascalis et al. The Journal of Immunology (2002) 169, 3076-3084.*
Casset et al. BBRC 2003, 307:198-205.*
Vajdos et al. J. Mol. Biol. (2002) 320, 415-428.*
Chen et al. J. Mol. Bio. (1999) 293, 865-881.*
Wu et al. J. Mol. Biol. (1999) 294, 151-162.*
Padlan et al. PNAS 1989, 86:5938-5942.*
Lamminmaki et al. JBC 2001, 276:36687-36694.*
MacCallum et al. J. Mol. Biol. (1996) 262, 732-745.*
Gondi et al. *Oncogene.* 22: 5967-5975 (2003).
Guo et al. *FASEB J.* 14:1400-1410 (2000).
Li et al. *Gene Therapy.* 5:1105-1113 (1998).
Li et al. *Human Gene Therapy.* 16: 1157-1167 (2005).
Mohan et al. *Cancer Research.* 59: 3369-3373 (1999).
Rabbani et al. *Cancer Research.* 62:2390-2397 (2002).
Zhu et al. *DNA and Cell Biology.* 20(5): 297-305 (2001).
Kirschenhofer et al., "Inhibition of uPA/uPAR interaction by recombinant single chain antibody scFvIIIF10: A promising agent for tumor therapy," Anticancer Research, 22(6C):4321 (Nov. 2002) and 2nd Conference on Experimental Tumor Biology; Slovenia; Mar. 2002 (abstract).
Kanse et al., "Induction of vascular SMC proliferation by urokinase indicates a novel mechanism of action in vasoproliferative disorders," Arteriosclerosis, Thrombosis, and Vascular Biology, 17(11):2848-2854 (Nov. 1997).
Sidenius, et al., "Domain 1 of the urokinase receptor (uPAR) is required for uPAR-mediated cell binding to vitronectin," FEBS Letters, 470(1):40-46 (Mar. 2000).
Okumura, et al., "Kinetic analysis of the interaction between vitronectin and the urokinase receptor," Journal of Biological Chemistry, 277(11):9395-9404 (Mar. 2002).
Hanes, et al., "Picomolar affinity antibodies from a fully synthetic naive library selected and evolved by ribosome display," Nature Biotechnology, 18(12):1287-1292 (Dec. 2000).
Wark, et al., "Latest technologies for the enhancement of antibody affinity," Advanced Drug Delivery Reviews, 58 (5-6):657-670 (Aug. 2006).
Cameliet, et al., "Urokinase-generated plasmin activates matrix metalloproteinases during aneurysm formation," Nature Genetics, 17(4):439-444 (Dec. 1997).
Little, et al., "Of mice and men: hybridoma and recombinant antibodies," Immunology today, 21(8):364-370 (Aug. 2000).
Davies, et al., "Affinity improvement of single antibody VH domains: residues in all three hypervariable regions affect antigen binding," Immunotechnology 2(3):169-179 (Sep. 1996).
Holt, et al., "Domain antibodies: proteins for therapy," Trends in Biotechnology, 21(11):484-490 (Nov. 2003).
Ueshima, et al., "Growth inhibition of vascular smooth muscle cells derived from urokinase receptor (u__PAR)-deficient mice in the presence of carcinoma cells," Thrombosis Research, 113(1):41-9 (2004).
Fuhrman, et al., "Urokinase plasminogen activator upregulates paraoxonase 2 expression in macrophages via an NADPH oxidase-dependent mechanism," Arteriosclerosis, Thrombosis, and Vascular Biology, 28(7):1361-7 (Apr. 2008).
Gu, et al., "Urokinase plasminogen activator receptor promotes macrophage infiltration into the vascular wall of ApoE deficient mice," Journal of Cell Physiology, 204(1):73-82 (2005).
Oka, et al., "Lysophosphatidylcholine induces urokinase-type plasminogen activator and its receptor in human macrophages partly through redox-sensitive pathway," Arteriosclerosis, Thrombosis, and Vascular Biology, 20(1):73-82 (2005).
Pepper, et al., "Upregulation of urokinase receptor expression on migrating endothelial cells," Cell Biology, 122 (3):673-84 (Aug. 1993).
Busso, et al., "Plasminogen activation in synovial tissues: differences between normal, osteoarthritis, and rheumatoid arthritis joints," Annals of Rheumatic Diseases., 56(9):550-7 (Sep. 1997).
Schwab, et al., "Expression of the urokinase-type plasminogen activator receptor in human articular chondrocytes: association with caveolin and beta 1-integrin," Histochemistry and Cell Biology,115(4):317-23 (Mar. 2001).

(Continued)

*Primary Examiner* — Sharon Wen

(57) ABSTRACT

Targeted binding agents directed to the antigen uPAR and uses of such antibodies are described. In particular, fully human monoclonal antibodies directed to the antigen uPAR. Nucleotide sequences encoding, and amino acid sequences comprising, heavy and light chain immunoglobulin molecules, particularly sequences corresponding to contiguous heavy and light chain sequences spanning the framework regions and/or complementarity determining regions (CDR's), specifically from FR1 through FR4 or CDR1 through CDR3. Hybridomas or other cell lines expressing such immunoglobulin molecules and monoclonal antibodies.

18 Claims, 9 Drawing Sheets

OTHER PUBLICATIONS

Furlan, et al., "Urokinase plasminogen activator receptor affects bone homeostasis by regulating osteoblast and osteoclast function," Journal of Bone and Mineral Research, 22(9):1387-96 (Sep. 2007).

Allan, et al., Prostaglandin E2 regulates production of plasminogen activator isoenzymes, urokinase receptor, and plasminogen activator inhibitor-1 in primary cultures of rat calvarial, Journal of Cellular Physiology, 165(3):521-9 (1995).

Leonard, et al., "Urokinase plasminogen activator, uPa receptor, and its inhibitor in vernal keratoconjunctivitis," Investigative Opthalmology & Visual Science, 46(4):1364-70 (Apr. 2005).

International Search Report mailed Jul. 4, 2008 in International Application No. PCT/US2007/008913.

* cited by examiner

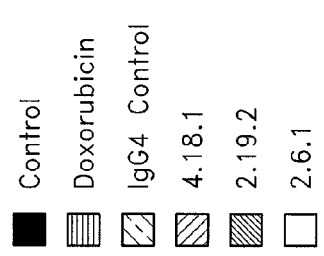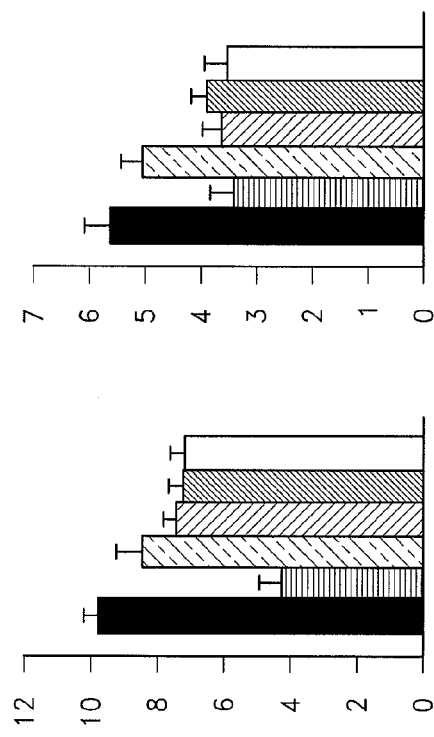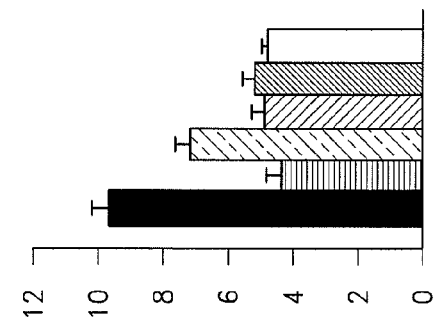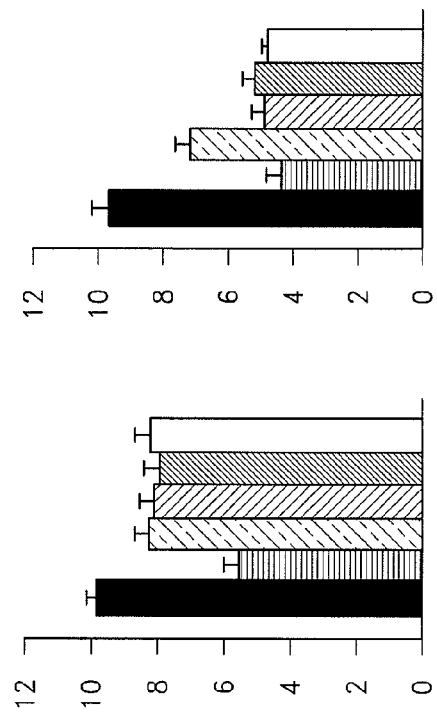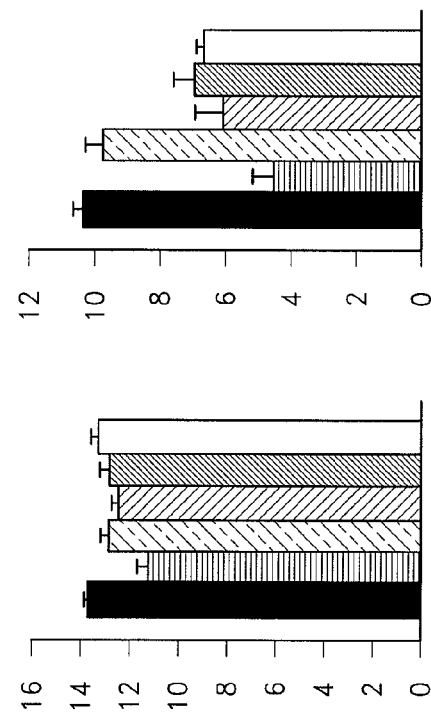

TARGETED BINDING AGENTS DIRECTED TO UPAR AND USES THEREOF

CROSS-REFERENCE TO RELATED APPLICATIONS

This application claims priority under 35 U.S.C. §119 to U.S. Provisional Application Ser. No. 60/790,642, filed Apr. 10, 2006, the entirety of which is hereby incorporated by reference.

REFERENCE TO SEQUENCE LISTING

The present application is being filed along with a Sequence Listing in electronic format. The Sequence Listing is provided as a file entitled ABXAZ__005.TXT, created Mar. 7, 2007, which is 84 Kb in size. The information in the electronic format of the Sequence Listing is incorporated herein by reference in its entirety.

FIELD

The invention relates to targeted binding agents against urokinase-type plasminogen activator receptor (uPAR) and uses of such agents. More specifically, the invention relates to fully human monoclonal antibodies directed to uPAR. The described binding agents are useful as diagnostics and for the treatment of diseases associated with the activity and/or overproduction of uPAR.

BACKGROUND

The urokinase-type plasminogen activator receptor (uPAR, CD87), GenBank Accession Number NP__002650, is a 55-60 kDa highly glycosylated 313 residue polypeptide that is linked to the outer leaflet of the cell membrane by a glycophosphatidylinositol (GPI)-anchor. The protein is folded into three highly homologous domains, DI, DII and DIII (Huai et al, Science 311: 656-659 2006). The N-terminal end of uPAR provides a urokinase plasminogen activator (uPA)-binding site (DI) (Gardsvoll et al, J Biol Chem 274: 37995-38003 1999). Evidence suggests that residues in domain 3 participate in the assembly of the ligand-binding site, and that domains 2 and 3 increase the affinity of uPA binding to domain 1 (Liang et al, J Biol Chem 276: 28946-28953 2001). The C-terminal domain (DIII) is processed to add a glycophosphatidylinositol (GPI)-anchor involving residues ser282, gly283, ala284. Proteolytic cleavage in the linker region between DI and DII (Hoyer-Hansen et al, Eur J Biochem 243: 21-26 1997; Andolfo et al, Thromb Hemost 88: 298-306 2002) and at residues within the C-terminal domain (Beaufort et al, J Immunol 172: 5450-549 2004) result in the presence of both a membrane anchored form comprising DII and DIII and a soluble forms of uPAR (suPAR) that comprise DI-DIII or DII-DIII. Cleavage of the glycolipid anchor may also release uPAR from the cell surface (Wilhelm et al, J Cell Physiol 180: 225-235 1999). Soluble uPAR incorporating DI retains the ability to bind urokinase (Higazi et al, J Biol Chem 270: 17375-17380 1995).

uPAR is expressed on the surface of many types of cells, including circulating leukocytes, vascular smooth muscle cells, angiogenic endothelial cells, bone marrow cells, and fibroblasts. Upregulation of uPAR expression at the cell surface, and plasminogen activation, has been linked to a number of conditions including inflammation, wound repair, arthritis (Szekanecz et al, J Clin Pathol 50: 314-319 1997), atherosclerosis (Carmeliet et al, Nature Genetics, 17: 439-444 1997), angiogenesis and tumor invasion and metastasis. The presence of elevated levels of soluble uPAR in plasma has been shown to be a prognostic marker in colorectal cancer (Stephens et al, J Natl Cancer Inst 91: 869-874 1999).

Activation of the inactive zymogen plasminogen to the serine protease plasmin is a key event regulating fibrinolysis. There are two plasminogen activators, tissue plasminogen activator (tPA) and urokinase plasminogen activator (uPA). Whereas tPA appears to be the key plasminogen activator in plasma, uPA is associated with cell surface plasminogen activation as a result of binding to uPAR. Urokinase is secreted as a single chain zymogen (scuPA) that exhibits very low or no intrinsic enzymatic activity. After enzymatic cleavage by plasmin, the scuPA is converted into an active, disulfide bond-linked, two-chain high molecular weight (HMW)-uPA. This HMW-uPA, is comprised of an A-chain (aa 1-158) and a B-chain, or LMW-uPA (aa 159-411). The primary interaction of uPA with uPAR is mediated through the growth factor domain (GFD) aa 1-48 of uPA in the A-chain, located in the amino-terminal fragment (ATF). A second site in uPA that interacts with uPAR (connecting peptide, aa 136-143) has been identified.

Binding affinity of uPA for uPAR is about 1 nM (Kd). Comparing the primary structure of uPAR among different species, human uPAR is 95% identical to that of Cynomolgus monkey (*Macaca fascicularis*), and only 60% identical to that of mouse (*Mus musculus*). Furthermore, the high affinity binding of uPA and uPAR is species specific. The affinities of the uPA for uPAR across species (e.g. human uPA to rat uPAR) differ by at least two orders of magnitude.

Cell surface recruitment of uPA to uPAR regulates cell surface plasminogen activation: scuPA is activated more efficiently when receptor bound (Ellis et al, J Biol Chem 264: 2185-2188 1989); the catalytic efficiency of receptor bound uPA is increased relative to uPA in solution phase (Higazi et al, J Biol Chem 270: 17375-17380 1995); PAI-1 is less efficient as an inhibitor of receptor bound uPA (Ellis et al, J Biol Chem 265: 9904-9908 1990). Plasminogen in turn is recruited to the cell surface through low and high affinity interactions and plasmin generation proceeds more effectively at the cell surface and is also less susceptible to its physiological inhibitors. At the tumor cell surface, plasminogen activation facilitates a number of processes that contribute to tumor progression including, activation of matrix-metalloproteases, degradation of extracellular matrix proteins, release and activation of growth factors that drive tumor growth and invasion (Andreasen et al, Int J Cancer 72: 1-22 1997).

In addition to the well established role in plasminogen activation, more recently evidence has established the role of uPAR as an adhesion receptor for vitronectin, a complex interaction that involves uPAR, uPA and PAI-1 (Waltz and Chapman, J Biol Chem 269: 14746-14750 1994; Czekay et al, J Cell Biol 160: 781-791 2003; Li et al, J Biol Chem 278: 29925-29932 2003). Cleavage of cell surface uPAR exposes an epitope on the DII domain that has been shown to be chemotactic in vitro (Degryse et al, J Biol Chem 280: 24792-24803 2005). Interactions with integrin receptors have been reported (e.g. Wei et al, J Cell Biol 168: 501-511 2005; Wei et al, Mol Biol Cell 12: 2975-2986 2001), and activation of cellular signaling pathways as a result of uPA binding have been demonstrated (reviewed in Blasi and Carmeliet, Nature Rev Mol Cell Biol 3: 932-943 2002)

Increased expression of uPAR and urokinase have been correlated with tumor progression in a range of human cancers including, breast, urinary bladder, gastric cancer, endometrial cancer, colorectal cancer (Edo de Bock and Wang, Med Res Reviews 24: 13-39 2004). uPAR gene expression is increased by tumor promoters, growth factors, cytokines and hormones as well as by atherogenic lipoproteins or hypoxia. Immunohistochemical and in situ hybridization studies have shown the uPA/uPAR complex to be localized to the invasive edge of a tumor, (Pyke et al, Am J Pathol 138: 1059-1067 1991) and correlated with tumor invasion. High expression levels of each uPA, uPAR or PAI-1 is linked to poor prognosis in different types of tumors (Duffy and Duggan, Clin Biochem 37: 541-548 2004).

Others have shown that a polyclonal urokinase receptor antibody can reduce tumor volume and detect the presence of occult tumor metastases in vivo (Rabbani and Gladu, Cancer Res. 62:2390-7 2002). Adenovirus mediated delivery of the uPA—ATF (Li et al, Gene Therapy 5 1105-1113 1998; Human Gene Therapy 16: 1157-1167 2005), stable transfection of uPA-ATF (Zhu et al, DNA Cell Biol 20: 297-305 2001), anti-sense uPAR (Mohan et al, Cancer Res 59: 3369-3373 1999) or combined antisense uPAR/uPA (Gondi et al, Oncogene 22: 5967-5975 2003) resulted in blockade or loss of uPAR activity and inhibition of invasion in vitro and tumor growth and invasion in vivo. In addition, a peptide derived from the non-receptor binding region of urokinase plasminogen activator (uPA) inhibited tumor progression and angiogenesis and induced tumor cell death in vivo (Guo et al, FASEB J. 14:1400-1410 2000).

SUMMARY

Embodiments of the invention relate to fully human targeted binding agents that specifically bind to uPAR and thereby inhibit plasminogen activation and activation of certain matrix-metalloproteases. The targeted binding agents also inhibit tumor cell adhesion and/or invasion, and/or cellular metastasis. In addition, the targeted binding agents are useful for reducing tumor growth. Mechanisms by which this can be achieved can include and are not limited to either inhibiting binding of uPA to its receptor uPAR, inhibiting uPAR/uPA localized uPA enzymatic activity, abrogation of intereactions with integrins or extracellular matrix proetins such as vitronectin, thereby reducing the effective concentration of uPAR.

Thus one embodiment of the invention is a targeted binding agent that specifically binds to uPAR and inhibits binding of uPA to uPAR. The targeted binding agent may bind uPAR with a $K_d$ of less than 100 µM, 10 µM, 1 µM, 100 nM, 10 nM, 1 nM, 500 pM, 400 pM, 300 pM, 200 pM, 100 pM or 50 pM.

Yet another embodiment is a targeted binding agent that binds to uPAR and inhibits greater than 90% of plasminogen activation on U937 cells at antibody concentrations as low as 100 µg/ml, 10 µg/ml, 8 µg/ml, 6 µg/ml, 4 µg/ml, 2 µg/ml, 1 µg/ml, 100 ng/ml, 10 ng/ml, 1 ng/ml, or 100 µg/ml or less.

Yet another embodiment is a targeted binding agent that binds to uPAR and inhibits plasminogen activation on U937 cells with an $IC_{50}$ of less than 10 µg/ml, 1 µg/ml, 0.1 µg/ml, 0.08 µg/ml, 0.06 µg/ml, 0.04 µg/ml, 0.02 µg/ml or 0.01 µg/ml.

Yet another embodiment is a targeted binding agent that binds to uPAR and inhibits greater than 90% of uPAR-mediated cell adhesion of U937 cells to vitronectin at targeted binding agent concentrations as low as 100 µg/ml, 10 µg/ml, 8 µg/ml, 6 µg/ml, 4 µg/ml, 2 µg/ml, 1 µg/ml, 100 ng/ml, 10 ng/ml, 1 ng/ml, or 100 pg/ml or less. Yet another embodiment is a targeted binding agent that binds to uPAR and inhibits greater than 80% of uPAR-mediated cell adhesion of U937 cells to vitronectin at targeted binding agent concentrations as low as 100 µg/ml, 10 µg/ml, 8 µg/ml, 6 µg/ml, 4 µg/ml, 2 µg/ml, 1 µg/ml, 100 ng/ml, 10 ng/ml, 1 ng/ml, 100 ng/ml, 10 ng/ml, 1 ng/ml, or 100 pg/ml or less.

Yet another embodiment is a targeted binding agent that binds to uPAR and inhibits greater than 90% of invasion of HT-1080 cells through Matrigel™ at targeted binding agent concentrations as low as 1000 µg/ml, 100 µg/ml, 10 µg/ml, 8 µg/ml, 6 µg/ml, 4 µg/ml, 2 µg/ml, 1 µg/ml, 100 ng/ml, 10 ng/ml, 1 ng/ml or 100 pg/ml or less.

In another embodiment the targeted binding agent may comprise a sequence comprising any one of the complementarity determining regions (CDR), CDR1, CDR2 or CDR3 sequences as shown in Table 18. In another embodiment the targeted binding agent may comprise a sequence comprising any two of a CDR1, CDR2 or CDR3 sequence as shown in Table 18 (that is either a CDR1 and CDR2, a CDR1 and CDR3, or a CDR2 and CDR3). In another embodiment the targeted binding agent may comprise a sequence comprising a CDR1, CDR2 and CDR3 sequence as shown in Table 18. It is noted that those of ordinary skill in the art can readily accomplish CDR determinations. See for example, Kabat et al., *Sequences of Proteins of Immunological Interest*, Fifth Edition, NIH Publication 91-3242, Bethesda Md. (1991), vols. 1-3.

In another embodiment the targeted binding agent may comprise a sequence comprising any one of a CDR1, CDR2 or CDR3 sequence as shown in Table 18. In another embodiment the targeted binding agent may comprise a sequence comprising any two of a CDR1, CDR2 or CDR3 sequence as shown in Table 18 (that is either a CDR1 and CDR2, a CDR1 and CDR3 or a CDR2 and CDR3). In another embodiment the targeted binding agent may comprise a sequence comprising a CDR1, CDR2 and CDR3 sequence as shown in Table 18.

In another embodiment the targeted binding agent may comprise a sequence comprising any one of a CDR1, CDR2 or CDR3 sequence as shown in Table 19. In another embodiment the targeted binding agent may comprise a sequence comprising any two of a CDR1, CDR2 or CDR3 sequence as shown in Table 19 (that is either a CDR1 and CDR2, a CDR1 and CDR3 or a CDR2 and CDR3). In another embodiment the targeted binding agent may comprise a sequence comprising a CDR1, CDR2 and CDR3 sequence as shown in Table 19.

In another embodiment the targeted binding agent may comprise a sequence comprising any one of a CDR1, CDR2 or CDR3 sequence of any one of either fully human monoclonal antibody 2.19.2 (ATCC Accession Number PTA-7474), 2.6.1 (ATCC Accession Number PTA-7475) or 4.18.1 (ATCC Accession Number PTA-7476), as shown in Table 18. PTA-7474, PTA-7475 and PTA-7476 were deposited on Apr. 6, 2006 with ATCC 10801 University Blvd, Manassas, Va., 20110-2209. In another embodiment the targeted binding agent may comprise a sequence comprising any two of a CDR1, CDR2 or CDR3 sequence of either fully human monoclonal antibody 2.19.2, 2.6.1 or 4.18.1 as shown in Table 18 (that is either a CDR1 and CDR2, a CDR1 and CDR3 or a CDR2 and CDR3). In another embodiment the targeted binding agent may comprise a sequence comprising a CDR1, CDR2 and CDR3 sequence of either fully human monoclonal antibody 2.19.2, 2.6.1 or 4.18.1 as shown in Table 18.

In another embodiment the targeted binding agent may comprise a sequence comprising any one of a CDR1, CDR2 or CDR3 sequence of either fully human monoclonal antibody 2.19.2 (SEQ ID NO.:100, SEQ ID NO.:101 and SEQ ID NO.: 102, respectively), 2.6.1 (SEQ ID NO.:103, SEQ ID NO.:104 and SEQ ID NO.: 105, respectively) or 4.18.1 (SEQ ID NO.:106, SEQ ID NO.:107 and SEQ ID NO.: 108, respectively) as shown in Table 19. In another embodiment the targeted binding agent may comprise a sequence comprising any two of a CDR1, CDR2 or CDR3 sequence of either fully human monoclonal antibody 2.19.2, 2.6.1 or 4.18.1 as shown in Table 19 (that is either a CDR1 and CDR2, a CDR1 and CDR3 or a CDR2 and CDR3). In another embodiment the targeted binding agent may comprise a sequence comprising a CDR1, CDR2 and CDR3 sequence of either fully human monoclonal antibody 2.19.2, 2.6.1 or 4.18.1 as shown in Table 19.

In another embodiment the targeted binding agent comprises a sequence comprising any one of a CDR1, CDR2 or CDR3 sequence as shown in Table 18 and any one of a CDR1, CDR2 or CDR3 sequence as shown in Table 19. In another embodiment the targeted binding agent comprises any two of a CDR1, CDR2 or CDR3 sequence shown in Table 18 and any two of a CDR1, CDR2 or CDR3 sequence as shown in Table 19 (that is either a CDR1 and CDR2, a CDR1 and CDR3 or a CDR2 and CDR3). In another embodiment the targeted binding agent comprises a CDR1, CDR2 and CDR3 sequence as shown in Table 18 and a CDR1, CDR2 and CDR3 sequence as shown in Table 19.

In another embodiment the targeted binding agent comprises a sequence comprising any one of a CDR1, CDR2 or CDR3 sequence of either fully human monoclonal antibody 2.19.2, 2.6.1 or 4.18.1 as shown in Table 18, and any one of a CDR1, CDR2 or CDR3 sequence of either fully human monoclonal antibody 2.19.2, 2.6.1 or 4.18.1 as shown in Table 19. In another embodiment the targeted binding agent comprises any two of a CDR1, CDR2 or CDR3 sequence of either fully human monoclonal antibody 2.19.2, 2.6.1 or 4.18.1 as shown in Table 18, and any two of a CDR1, CDR2 or CDR3 sequence of either fully human monoclonal antibody 2.19.2, 2.6.1 or 4.18.1 as shown in Table 19 (that is either a CDR1 and CDR2, a CDR1 and CDR3 or a CDR2 and CDR3). In another embodiment the targeted binding agent comprises a CDR1, CDR2 and CDR3 sequence of either fully human monoclonal antibody 2.19.2, 2.6.1 or 4.18.1 as shown in Table 18, and a CDR1, CDR2 and CDR3 sequence of either fully human monoclonal antibody 2.19.2, 2.6.1 or 4.18.1 as shown in Table 19.

In another embodiment the targeted binding agent comprises a sequence comprising a CDR1, CDR2 and CDR3 sequence of fully human monoclonal antibody 2.19.2 as shown in Table 18, and a CDR1, CDR2 and CDR3 sequence of fully human monoclonal antibody 2.19.2 as shown in Table 19. In another embodiment the targeted binding agent comprises a sequence comprising a CDR1, CDR2 and CDR3 sequence of fully human monoclonal antibody 2.6.1 as shown in Table 18, and a CDR1, CDR2 and CDR3 sequence of fully human monoclonal antibody 2.6.1 as shown in Table 19. In another embodiment the targeted binding agent comprises a sequence comprising a CDR1, CDR2 and CDR3 sequence of fully human monoclonal antibody 4.18.1 as shown in Table 18, and a CDR1, CDR2 and CDR3 sequence of fully human monoclonal antibody 4.18.1 as shown in Table 19.

In one embodiment of the invention, the targeted binding agent is an antibody. In one embodiment of the invention, the targeted binding agent is a monoclonal antibody. In one embodiment of the invention, the targeted binding agent is a fully human monoclonal antibody.

In another embodiment there is an antibody that binds to uPAR and comprises a light chain amino acid sequence comprising any one of a CDR1, CDR2 or CDR3 sequence as shown in Table 19. In another embodiment there is an antibody that binds to uPAR and comprises a light chain amino acid sequence comprising any two of a CDR1, CDR2 or CDR3 sequence as shown in Table 19 (that is either a CDR1 and CDR2, a CDR1 and CDR3 or a CDR2 and CDR3). In another embodiment there is an antibody that binds to uPAR and comprises a light chain amino acid sequence comprising a CDR1, a CDR2 and a CDR3 sequence as shown in Table 19. In certain embodiments the antibody is a fully human monoclonal antibody.

Yet another embodiment is an antibody that binds to uPAR and comprises a heavy chain amino acid sequence comprising any one of a CDR1, CDR2 or CDR3 sequence as shown in Table 18. In another embodiment there is an antibody that binds to uPAR and comprises a heavy chain amino acid sequence comprising any two of a CDR1, CDR2 or CDR3 sequence as shown in Table 18 (that is either a CDR1 and CDR2, a CDR1 and CDR3 or a CDR2 and CDR3). In another embodiment there is an antibody that binds to uPAR and comprises a heavy chain amino acid sequence comprising a CDR1, a CDR2 and a CDR3 sequence as shown in Table 18. In certain embodiments the antibody is a fully human monoclonal antibody.

In another embodiment the antibody that binds to uPAR may comprise an amino acid sequence comprising any one of a CDR1, CDR2 or CDR3 sequence of either fully human monoclonal antibody 2.19.2, 2.6.1 or 4.18.1 as shown in Table 18. In another embodiment the antibody may comprise an amino acid sequence comprising any two of a CDR1, CDR2 or CDR3 sequence of either fully human monoclonal antibody 2.19.2, 2.6.1 or 4.18.1 as shown in Table 18 (that is either a CDR1 and CDR2, a CDR1 and CDR3 or a CDR2 and CDR3). In another embodiment the antibody may comprise an amino acid sequence comprising a CDR1, CDR2 and CDR3 sequence of either fully human monoclonal antibody 2.19.2, 2.6.1 or 4.18.1 as shown in Table 18.

In another embodiment the antibody that binds to uPAR may comprise an amino acid sequence comprising any one of a CDR1, CDR2 or CDR3 sequence of either fully human monoclonal antibody 2.19.2, 2.6.1 or 4.18.1 as shown in Table 19. In another embodiment the antibody may comprise an amino acid sequence comprising any two of a CDR1, CDR2 or CDR3 sequence of either fully human monoclonal antibody 2.19.2, 2.6.1 or 4.18.1 as shown in Table 19 (that is either a CDR1 and CDR2, a CDR1 and CDR3 or a CDR2 and CDR3). In another embodiment the antibody may comprise an amino acid sequence comprising a CDR1, CDR2 and CDR3 sequence of either fully human monoclonal antibody 2.19.2, 2.6.1 or 4.18.1 as shown in Table 19.

In another embodiment the antibody that binds to uPAR comprises a heavy chain amino acid sequence comprising any one of a CDR1, CDR2 or CDR3 sequence as shown in Table 18 and a light chain amino acid sequence comprising one of a CDR1, CDR2 or CDR3 sequence as shown in Table 19. In another embodiment the antibody comprises a heavy chain amino acid sequence comprising any two of a CDR1, CDR2 or CDR3 sequence as shown in Table 18 and a light chain amino acid sequence comprising any two of a CDR1, CDR2 or CDR3 sequence as shown in Table 19 (that is either a CDR1 and CDR2, a CDR1 and CDR3 or a CDR2 and CDR3). In another embodiment the antibody comprises a heavy chain amino acid sequence comprising a CDR1, CDR2 and CDR3 sequence as shown in Table 18 and a light chain amino acid sequence comprising a CDR1, CDR2 and CDR3 sequence as shown in Table 19.

In another embodiment the antibody that binds to uPAR comprises a heavy chain amino acid sequence comprising any one of a CDR1, CDR2 or CDR3 sequence of either fully human monoclonal antibody 2.19.2, 2.6.1 or 4.18.1 as shown in Table 18 and a light chain amino acid sequence comprising any one of a CDR1, CDR2 or CDR3 sequence of either fully human monoclonal antibody 2.19.2, 2.6.1 or 4.18.1 as shown in Table 19. In another embodiment the antibody comprises a heavy chain amino acid sequence comprising any two of a CDR1, CDR2 or CDR3 sequence of either fully human monoclonal antibody 2.19.2, 2.6.1 or 4.18.1 as shown in Table 18 and a light chain amino acid sequence comprising any two of a CDR1, CDR2 or CDR3 sequence of either fully human monoclonal antibody 2.19.2, 2.6.1 or 4.18.1 as shown in Table 19 (that is either a CDR1 and CDR2, a CDR1 and CDR3 or a CDR2 and CDR3). In another embodiment the antibody comprises a heavy chain amino acid sequence comprising a CDR1, CDR2 and CDR3 sequence of either fully human monoclonal antibody 2.19.2, 2.6.1 or 4.18.1 as shown in Table 18 and a light chain amino acid sequence comprising a CDR1, CDR2 and CDR3 sequence of either fully human monoclonal antibody 2.19.2, 2.6.1 or 4.18.1 as shown in Table 19.

In another embodiment the antibody comprises a heavy chain amino acid sequence comprising a CDR1, CDR2 and CDR3 sequence of fully human monoclonal antibody 2.19.2 as shown in Table 18 and a light chain amino acid sequence comprising a CDR1, CDR2 and CDR3 sequence of fully human monoclonal antibody 2.19.2 as shown in Table 19. In another embodiment the antibody comprises a heavy chain amino acid sequence comprising a CDR1, CDR2 and CDR3 sequence of fully human monoclonal antibody 2.6.1 as shown in Table 18 and a light chain amino acid sequence comprising a CDR1, CDR2 and CDR3 sequence of fully human monoclonal antibody 2.6.1 as shown in Table 19. In another embodiment the antibody comprises a heavy chain amino acid sequence comprising a CDR1, CDR2 and CDR3 sequence of fully human monoclonal antibody 4.18.1 as shown in Table 18 and a light chain amino acid sequence comprising a CDR1, CDR2 and CDR3 sequence of fully human monoclonal antibody 4.18.1 as shown in Table 19.

A further embodiment of the invention is a targeted binding agent which cross-competes for binding to uPAR with the targeted binding agent or antibodies of the invention. In another embodiment of the invention there is an antibody which cross-competes for binding to uPAR with the targeted binding agent or antibodies of the invention.

In another embodiment the targeted binding agent or antibody cross-competes for binding to uPAR with any one of fully human monoclonal antibodies 2.19.2, 2.6.1 and 4.18.1. In one embodiment of the invention is an antibody which cross-competes with any one of fully human monoclonal antibodies 2.19.2, 2.6.1 and 4.18.1 for binding to uPAR.

A further embodiment of the invention is a targeted binding agent that binds to the same epitope on uPAR as the targeted binding agent or antibodies of the invention. In another embodiment of the invention there is an antibody that binds to the same epitope on uPAR as the targeted binding agent or antibodies of the invention.

In one embodiment of the invention is a targeted binding agent that binds to the same epitope on uPAR as any one of fully human monoclonal antibodies 2.19.2, 2.6.1 and 4.18.1. In one embodiment of the invention is an antibody that binds to the same epitope on uPAR as any one of fully human monoclonal antibodies 2.19.2, 2.6.1 and 4.18.1.

In one embodiment, the targeted binding agent comprises one or more of fully human monoclonal antibodies 2.19.2 (ATCC Accession Number PTA-7474), 2.6.1 (ATCC Accession Number PTA-7475) and/or 4.18.1 (ATCC Accession Number PTA-7476) which specifically bind to uPAR, as discussed in more detail below.

In one embodiment there is provided a targeted binding agent or antibody produced by the hybridoma selected from ATCC Accession Number PTA-7474, ATCC Accession Number PTA-7475 and ATCC Accession Number PTA-7476. In one embodiment there is provided a targeted binding agent or an antibody derivable from the antibody produced by the hybridoma selected from ATCC Accession Number PTA-7474, ATCC Accession Number PTA-7475 and ATCC Accession Number PTA-7476.

In one embodiment, the targeted binding agent comprises an antibody derivable from one or more of fully human monoclonal antibodies 2.19.2 (ATCC Accession Number PTA-7474), 2.6.1 (ATCC Accession Number PTA-7475) and/or 4.18.1 (ATCC Accession Number PTA-7476).

In one embodiment, the targeted binding agent comprises a polypeptide having the sequence of SEQ ID NO.: 26, 30 or 50. In one embodiment, the targeted binding agent comprises a polypeptide having the sequence of SEQ ID NO.: 28, 32 or 52. In one embodiment, the antibody of the invention comprises a heavy chain polypeptide having the sequence of SEQ ID NO.: 26, 30 or 50. In one embodiment, the antibody of the invention comprises a light chain polypeptide having the sequence of SEQ ID NO.: 28, 32 or 52.

In one embodiment, the targeted binding agent of the invention comprises a polypeptide comprising the sequence of SEQ ID NO.: 26, wherein the sequence has any one of the unique combination of germline and non-germline residues indicated by each row of Table 15. In one embodiment, the targeted binding agent of the invention comprises a polypeptide comprising the sequence of SEQ ID NO.: 30, wherein the sequence has any one of the unique combination of germline and non-germline residues indicated by each row of Table 13. In one embodiment, the targeted binding agent of the invention comprises a polypeptide comprising the sequence of SEQ ID NO.: 50, wherein the sequence has any one of the unique combination of germline and non-germline residues indicated by each row of Table 17. In one embodiment, the targeted binding agent of the invention comprises a polypeptide comprising the sequence of SEQ ID NO.: 28, wherein the sequence has any one of the unique combination of germline and non-germline residues indicated by each row of Table 14. In one embodiment, the targeted binding agent of the invention comprises a polypeptide comprising the sequence of SEQ ID NO.: 32, wherein the sequence has any one of the unique combination of germline and non-germline residues indicated by each row of Table 12. In one embodiment, the targeted binding agent of the invention comprises a polypeptide comprising the sequence of SEQ ID NO.: 52, wherein the sequence has any one of the unique combination of germline and non-germline residues indicated by each row of Table 16.

In one embodiment, the antibody of the invention comprises a heavy chain polypeptide comprising the sequence of SEQ ID NO.: 26, wherein the sequence has any one of the unique combination of germline and non-germline residues indicated by each row of Table 15. In one embodiment, the antibody of the invention comprises a heavy chain polypeptide comprising the sequence of SEQ ID NO.: 30, wherein the sequence has any one of the unique combination of germline and non-germline residues indicated by each row of Table 13. In one embodiment, the antibody of the invention comprises a heavy chain polypeptide comprising the sequence of SEQ ID NO.: 50, wherein the sequence has any one of the unique combination of germline and non-germline residues indicated by each row of Table 17. In one embodiment, the antibody of the invention comprises a light chain polypeptide comprising the sequence of SEQ ID NO.: 28, wherein the sequence has any one of the unique combination of germline and non-germline residues indicated by each row of Table 14. In one embodiment, the antibody of the invention comprises a light chain polypeptide comprising the sequence of SEQ ID NO.: 32, wherein the sequence has any one of the unique combination of germline and non-germline residues indicated by each row of Table 12. In one embodiment, the antibody of the invention comprises a light chain polypeptide comprising the sequence of SEQ ID NO.: 52, wherein the sequence has any one of the unique combination of germline and non-germline residues indicated by each row of Table 16.

The invention further provides methods for assaying the level of uPAR in a patient sample, comprising contacting a targeted binding agent or an anti-uPAR antibody of the invention with a biological sample from a patient, and detecting the level of binding between said antibody and uPAR in said sample. In more specific embodiments, the biological sample is blood, plasma, saliva, cerebrospinal fluid, bone marrow or urine.

In other embodiments the invention provides compositions, including a targeted binding agent of the invention or binding fragment thereof, and a pharmaceutically acceptable carrier. In other embodiments the invention provides compositions, including an antibody of the invention or binding fragment thereof, and a pharmaceutically acceptable carrier.

The invention provides methods of treating a malignant tumor in an animal by selecting an animal in need of treatment for a malignant tumor and administering to the animal a therapeutically effective dose of the targeted binding agent of the invention that binds to uPAR. In certain embodiments, the animal is human. In certain embodiments, the targeted binding agent is an antibody of the invention and may be selected from the group consisting of 2.19.2 (ATCC Accession Number PTA-7474), 2.6.1 (ATCC Accession Number PTA-7475) and 4.18.1 (ATCC Accession Number PTA-7476).

In certain embodiments, the malignant tumor can be selected from the group consisting of: melanoma, small cell lung cancer, non-small cell lung cancer, glioma, hepatocellular (liver) carcinoma, thyroid tumor, gastric (stomach) cancer, prostate cancer, breast cancer, ovarian cancer, bladder cancer, lung cancer, glioblastoma, endometrial cancer, kidney cancer, colon cancer, pancreatic cancer, esophageal carcinoma, head and neck cancers, mesothelioma, sarcomas, biliary (cholangiocarcinoma), small bowel adenocarcinoma, pediatric malignancies and epidermoid carcinoma.

Still further embodiments of the invention include methods of effectively treating an animal suffering from a cell adhesion- and/or invasion-related diseases, including selecting an animal in need of treatment for a cell adhesion- and/or invasion-related disease, and administering to the animal a therapeutically effective dose of a targeted binding agent of the invention that specifically binds to uPAR. In certain embodiments, the animal is human. In certain embodiments, the targeted binding agent is a fully human monoclonal antibody. In certain embodiments, the cell adhesion- or cell invasion-related disease is tumor metastasis. In certain embodiments, the targeted binding agent is an antibody of the invention and may be selected from the group consisting of 2.19.2 (ATCC Accession Number PTA-7474), 2.6.1 (ATCC Accession Number PTA-7475) and 4.18.1 (ATCC Accession Number PTA-7476).

Treatable cell adhesion- and invasion-related diseases include neoplastic diseases, such as, melanoma, small cell lung cancer, non-small cell lung cancer, glioma, hepatocellular (liver) carcinoma, thyroid tumor, gastric (stomach) cancer, prostate cancer, breast cancer, ovarian cancer, bladder cancer, lung cancer, glioblastoma, endometrial cancer, kidney cancer, colon cancer, pancreatic cancer, esophageal carcinoma, head and neck cancers, mesothelioma, sarcomas, biliary (cholangiocarcinoma), small bowel adenocarcinoma, pediatric malignancies and epidermoid carcinoma.

Treatable cell adhesion- and invasion-related diseases include non-neoplastic diseases, such as, inflammatory, or hyperprolifearative diseases including but not limited to arthritis, atherosclerosis, allergic conjunctivitis.

Additional embodiments of the invention include methods of inhibiting uPAR induced cell adhesion and/or invasion in an animal. These methods include selecting an animal in need of treatment for uPAR induced cell adhesion and invasion, and administering to said animal a therapeutically effective dose of a targeted binding agent or fully human monoclonal antibody of the invention wherein said antibody specifically binds to uPAR.

Further embodiments of the invention include the use of a targeted binding agent or an antibody of the invention in the preparation of medicament for the treatment of cell adhesion- or invasion-related diseases in an animal, wherein said monoclonal antibody specifically binds to uPAR.

In still further embodiments, the targeted binding agents described herein can be used for the preparation of a medicament for the effective treatment of uPAR induced cell adhesion, and/or invasion in an animal, wherein said targeted binding agent specifically binds to uPAR. In still further embodiments, the antibodies described herein can be used for the preparation of a medicament for the effective treatment of uPAR induced cell adhesion, and/or invasion in an animal, wherein said antibody specifically binds to uPAR.

Embodiments of the invention described herein relate to targeted binding agents that bind uPAR and affect uPAR function. Other embodiments of the invention described herein relate to monoclonal antibodies that bind uPAR and affect uPAR function. Other embodiments relate to anti-uPAR antibodies of the invention with desirable properties from a therapeutic perspective, including high binding affinity for uPAR, the ability to neutralize uPAR in vitro and in vivo and the ability to inhibit uPAR induced cell adhesion and/or invasion and/or tumor growth. Other embodiments relate to preparations of an anti-uPAR antibody of the invention with desirable properties from a therapeutic perspective, including high binding affinity for uPAR, the ability to neutralize uPAR in vitro and in vivo and the ability to inhibit uPAR induced cell adhesion and/or invasion and/or tumor growth. Other embodiments relate to fully human anti-uPAR antibodies of the invention with desirable properties from a therapeutic perspective, including high binding affinity for uPAR, the ability to neutralize uPAR in vitro and in vivo and the ability to inhibit uPAR induced cell adhesion and/or invasion and/or tumor growth. Other embodiments relate to preparations of a fully human anti-uPAR antibody of the invention with desirable properties from a therapeutic perspective, including high binding affinity for uPAR, the ability to neutralize uPAR in vitro and in vivo and the ability to inhibit uPAR induced cell adhesion and/or invasion and/or tumor growth.

In one embodiment, the invention includes antibodies that bind to uPAR with very high affinities (Kd). For example a human, rabbit, mouse, chimeric or humanized antibody that is capable of binding uPAR with a $K_d$ less than, but not limited to, $10^{-5}$, $10^{-6}$, $10^{-7}$, $10^{-8}$, $10^{-9}$, $10^{-10}$ or $10^{-11}$M, or any range or value therein. Affinity and/or avidity measurements can be measured by KinExA® and/or BIACORE®, as described herein.

One embodiment of the invention includes isolated antibodies, or fragments of those antibodies, that bind to uPAR. As known in the art, the antibodies can be, for example, polyclonal, oligoclonal, monoclonal, chimeric, humanized, and/or fully human antibodies. Embodiments of the invention described herein also provide cells for producing these antibodies.

It will be appreciated that embodiments of the invention are not limited to any particular form of an antibody or method of generation or production. For example, the anti-uPAR antibody of the invention may be a full-length antibody (e.g., having an intact human Fc region) or an antibody fragment (e.g., a Fab, Fab', F(ab')$_2$, Fv or Dab (Dabs are the smallest functional binding units of human antibodies). In addition, the antibody may be manufactured from a hybridoma that secretes the antibody, or from a recombinantly produced cell that has been transformed or transfected with a gene or genes encoding the antibody.

Other embodiments of the invention include isolated nucleic acid molecules encoding any of the targeted binding agents, antibodies or fragments thereof as described herein, vectors having isolated nucleic acid molecules encoding anti-uPAR antibodies or a host cell transformed with any of such nucleic acid molecules. In addition, one embodiment of the invention is a method of producing an anti-uPAR antibody of the invention by culturing host cells under conditions wherein a nucleic acid molecule is expressed to produce the antibody followed by recovering the antibody. It should be realized that embodiments of the invention also include any nucleic acid molecule which encodes an antibody or fragment of an antibody of the invention including nucleic acid sequences optimized for increasing yields of antibodies or fragments thereof when transfected into host cells for antibody production.

A further embodiment includes a method of producing high affinity antibodies to uPAR by immunizing a mammal with human uPAR, or a fragment thereof, and one or more orthologous sequences or fragments thereof.

Other embodiments are based upon the generation and identification of isolated antibodies that bind specifically to uPAR. uPAR is expressed at elevated levels in cell adhesion- and/or invasion-related diseases, such as neoplastic diseases. Inhibition of the biological activity of uPAR can prevent uPAR induced cell adhesion and invasion and other desired effects.

Another embodiment of the invention includes a method of diagnosing diseases or conditions in which an antibody prepared as described herein is utilized to detect the level of uPAR in a patient sample. In one embodiment, the patient sample is blood or blood serum. In further embodiments, methods for the identification of risk factors, diagnosis of disease, and staging of disease is presented which involves the identification of the overexpression of uPAR using anti-uPAR antibodies.

Another embodiment of the invention includes a method for diagnosing a condition associated with the expression of uPAR in a cell by contacting the serum or a cell with a targeted binding agent or an anti-uPAR antibody of the invention, and thereafter detecting the presence of uPAR. Preferred conditions include cell adhesion- and/or invasion-related diseases including, but not limited to, neoplastic diseases, such as, melanoma, small cell lung cancer, non-small cell lung cancer, glioma, hepatocellular (liver) carcinoma, glioblastoma, and carcinoma of the thyroid, stomach, prostate, breast, ovary, bladder, lung, uterus, kidney, colon, and pancreas, salivary gland, and colorectum.

In another embodiment, the invention includes an assay kit for detecting uPAR in mammalian tissues, cells, or body fluids to screen for uPAR-related diseases. The kit includes a targeted binding agent or an antibody of the invention that binds to uPAR and a means for indicating the reaction of the antibody with uPAR, if present. In one embodiment, the antibody is a monoclonal antibody. In another embodiment, the antibody that binds uPAR is labeled. In still another embodiment the antibody is an unlabeled primary antibody and the kit further includes a means for detecting the primary antibody. In one embodiment, the means for detecting includes a labeled second antibody that is an anti-immunoglobulin. The antibody may be labeled with a marker selected from the group consisting of a fluorochrome, an enzyme, a radionuclide and a radiopaque material.

Other embodiments of the invention include pharmaceutical compositions having an effective amount of a targeted binding agent or an anti-uPAR antibody of the invention in admixture with a pharmaceutically acceptable carrier or diluent. In yet other embodiments, the targeted binding agent or anti-uPAR antibody of the invention, or a fragment thereof, is conjugated to a therapeutic agent. The therapeutic agent can be, for example, a toxin or a radioisotope.

Yet another embodiment includes methods for treating diseases or conditions associated with the expression of uPAR in a patient, by administering to the patient an effective amount of a targeted binding agent or an anti-uPAR antibody of the invention. The targeted binding agent or anti-uPAR antibody of the invention can be administered alone, or can be administered in combination with additional antibodies or chemotherapeutic drug or radiation therapy. For example, a monoclonal, oligoclonal or polyclonal mixture of uPAR antibodies that block cell adhesion and/or invasion can be administered in combination with a drug shown to inhibit tumor cell proliferation directly. The method can be performed in vivo and the patient is preferably a human patient. In a preferred embodiment, the method concerns the treatment of cell adhesion- and/or invasion-related diseases including, but not limited to, neoplastic diseases, such as, melanoma, small cell lung cancer, non-small cell lung cancer, glioma, hepatocellular (liver) carcinoma, glioblastoma, and carcinoma of the thyroid, stomach, prostate, breast, ovary, bladder, lung, uterus, kidney, colon, and pancreas, salivary gland, and colorectum.

In another embodiment, the invention provides an article of manufacture including a container. The container includes a composition containing a targeted binding agent or an anti-uPAR antibody of the invention, and a package insert or label indicating that the composition can be used to treat cell adhesion- and/or invasion-related diseases characterized by the overexpression of uPAR.

In some embodiments, the targeted binding agent or anti-uPAR antibody of the invention is administered to a patient, followed by administration of a clearing agent to remove excess circulating antibody from the blood.

Yet another embodiment is the use of a targeted binding agent or an anti-uPAR antibody of the invention in the preparation of a medicament for the treatment of diseases such as cell adhesion- and/or invasion-related diseases. In one embodiment, the cell adhesion- and/or invasion-related diseases include carcinoma, such as breast, ovarian, stomach, endometrial, salivary gland, lung, kidney, colon, colorectum, esophageal, thyroid, pancreatic, prostate and bladder cancer. In another embodiment, the cell adhesion- and/or invasion-related diseases include, but are not limited to, neoplastic diseases, such as, melanoma, small cell lung cancer, non-small cell lung cancer, glioma, hepatocellular (liver) carcinoma, sarcoma, head and neck cancers, mesothelioma, biliary (cholangiocarcinoma), small bowel adenocarcinoma, pediatric malignancies and glioblastoma.

Yet another embodiment is the use of a targeted binding agent or an anti-uPAR antibody of the invention in the preparation of a medicament for the treatment of a malignant tumour in an animal.

Yet another embodiment of the invention is the use of a targeted binding agent or an anti-uPAR antibody of the invention in the preparation of a medicament for the treatment of a non-neoplastic disease. Yet another embodiment of the invention is the use of a targeted binding agent or an anti-uPAR antibody of the invention in the preparation of a medicament for the treatment of inflammatory, or hyperproliferative diseases including but not limited to arthritis, atherosclerosis, allergic conjunctivitis.

BRIEF DESCRIPTION OF THE DRAWINGS

FIGS. 8A-F are bar graphs showing the activity of anti-uPAR monoclonal antibodies on tumour biomarker expression, measured in primary tumors of MDA-MB231-GFP orthotopic xenografts. The data represents the mean+/−standard deviation of staining intensity (density) measured from tumors of six animals per treatment group; ki-67 (FIG. 8a), CD31 (FIG. 8b), MAPK (FIG. 8c), pMAPK (FIG. 8d), FAK (FIG. 8e), pFAK (FIG. 8f), including untreated, doxorubicin and IgG4 controls.

DETAILED DESCRIPTION

Figure 1:
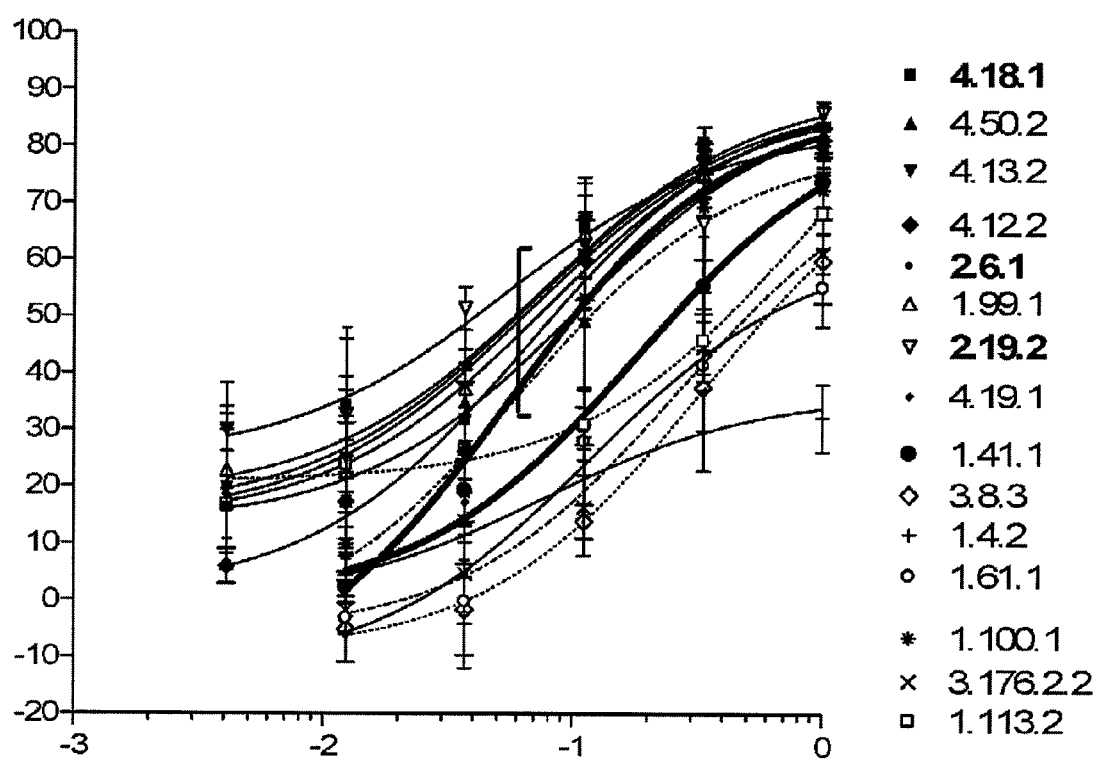
FIG. 1 is a line graph showing the inhibitory effect of fifteen anti-uPAR monoclonal antibodies in a plasminogen activation inhibition assay. The dose-response relationship curve for each mAb is illustrated. The eight antibodies which exhibited the highest efficacy and potency are indicated by the vertical bracket. Bold face legends indicate antibodies which exhibited the strongest inhibition. Percentage of inhibition ("% Inhibition") is shown as a function of antibody concentration with units of Log [mAb](μg/ml).

Embodiments of the invention relate to targeted binding agents that bind to urokinase-type plasminogen activator receptor (uPAR). In some embodiments, the binding agents bind to uPAR and inhibit the binding of urokinase-type plasminogen activator (uPA) to its receptor, uPAR. In one embodiment, the targeted binding agents are monoclonal antibodies, or binding fragments thereof.

Other embodiments of the invention include fully human anti-uPAR antibodies, and antibody preparations that are therapeutically useful. In one embodiment, preparations of the anti-uPAR antibody of the invention have desirable therapeutic properties, including strong binding affinity for uPAR, the ability to inhibit plasminogen activation in vitro, and the ability to inhibit uPAR-induced cell adhesion and invasion in vitro and in vivo.

Embodiments of the invention also include isolated binding fragments of anti-uPAR antibodies. In one embodiment the binding fragments are derived from fully human anti-uPAR antibodies. Exemplary fragments include Fv, Fab', Dabor other well-known antibody fragments, as described in more detail below. Embodiments of the invention also include cells that express fully human antibodies against uPAR. Examples of cells include hybridomas, or recombinantly created cells, such as Chinese hamster ovary (CHO) cells, variants of CHO cells (for example DG44) and NS0 cells that produce antibodies against uPAR. Additional information about variants of CHO cells can be found in Andersen and Reilly (2004) *Current Opinion in Biotechnology* 15, 456-462 which is incorporated herein in its entirety by reference.

In addition, embodiments of the invention include methods of using these antibodies for treating diseases. Anti-uPAR antibodies of the invention are useful for preventing uPAR-mediated plasminogen activation, thereby inhibiting cell adhesion and/or invasion. While not being limited to any particular theory, the mechanism of action of this inhibition may include inhibition of uPA from binding to its receptor, uPAR. Anti-uPAR antibodies of the invention may also inhibit uPAR/uPA localized uPA enzymatic activity, thereby reducing the effective concentration of uPAR. Anti-uPAR antibodies of the invention may inhibit uPAR dependent adhesion of cells to vitronectin and may also disrupt uPAR modification of integrin mediated cell adhesion. Anti-uPAR antibodies of the invention may also modify intracellular signalling as a result of inhibiting uPA binding to uPAR or disruption of uPAR interactions with integrins and growth factor receptors. Diseases that are treatable through this inhibition mechanism include, but are not limited to, neoplastic diseases, such as melanoma, small cell lung cancer, non-small cell lung cancer, glioma, hepatocellular (liver) carcinoma, glioblastoma, and cancers and tumors of the thyroid, stomach, prostate, breast, ovary, bladder, lung, uterus, kidney, colon, and pancreas, salivary gland, and colorectum.

Other embodiments of the invention include diagnostic assays for specifically determining the quantity of uPAR in a biological sample. The assay kit can include anti-uPAR antibodies of the invention along with the necessary labels for detecting such antibodies. These diagnostic assays are useful to screen for cell adhesion- and invasion-related diseases including, but not limited to, neoplastic diseases, such as, melanoma, small cell lung cancer, non-small cell lung cancer, glioma, hepatocellular (liver) carcinoma, glioblastoma, and carcinoma of the thyroid, stomach, prostate, breast, ovary, bladder, lung, uterus, kidney, colon, and pancreas, salivary gland, and colorectum.

Another aspect of the invention is an antagonist of the biological activity of uPAR wherein the antagonist binds to uPAR. In one embodiment, the antagonist is a targeted binding agent, such as an antibody. The antagonist may bind to:
  i) uPAR; or
  ii) the uPA/uPAR complex,
or a combination of these. In one embodiment the antagonist is able to antagonize the biological activity of uPAR in vitro and in vivo. The antagonist may be selected from an antibody described herein, for example fully human monoclonal antibody 2.19.2 (ATCC Accession Number PTA-7474), 2.6.1 (ATCC Accession Number PTA-7475) and 4.18.1 (ATCC Accession Number PTA-7476).

In one embodiment the antagonist of the biological activity of uPAR may bind to uPAR and thereby prevent uPAR mediated plasminogen activation, thereby inhibiting cell adhesion and/or invasion. The mechanism of action of this inhibition may include binding of the antagonist to uPAR and inhibiting the binding of uPA to its receptor, uPAR. Without wishing to be bound by any particular theoretical considerations, mechanisms by which antagonism of the biological activity of uPAR can be achieved include, but are not limited to, inhibition of binding of uPA to the receptor uPAR, or inhibition of uPAR/uPA localized uPA enzymatic activity.

One embodiment is a targeted binding agent which binds to the same epitope or epitopes as fully human monoclonal antibody 2.19.2, 2.6.1 or 4.18.1.

One embodiment is an antibody which binds to the same epitope or epitopes as fully human monoclonal antibody 2.19.2, 2.6.1 or 4.18.1.

In one embodiment, the targeted binding agent binds uPAR with a $K_d$ of less than 1 nanomolar (nM). The targeted binding agent may bind with a $K_d$ less than 500 picomolar (pM). The targeted binding agent may bind with a $K_d$ less than 400 picomolar (pM). The targeted binding agent may bind with a $K_d$ less than 300 picomolar (pM). In another embodiment, the targeted binding agent binds with a $K_d$ of less than 200 pM.

One embodiment is a hybridoma that produces the targeted binding agent as described hereinabove. In one embodiment is a hybridoma that produces the light chain and/or the heavy chain of the antibodies as described hereinabove. In one embodiment the hybridoma produces the light chain and/or the heavy chain of a fully human monoclonal antibody. In another embodiment the hybridoma produces the light chain and/or the heavy chain of the fully human monoclonal antibody 2.19.2, 2.6.1 or 4.18.1. Alternatively the hybridoma may produce an antibody which binds to the same epitope or epitopes as fully human monoclonal antibody 2.19.2, 2.6.1 or 4.18.1.

Another embodiment is a nucleic acid molecule encoding the targeted binding agent as described hereinabove. In one embodiment is a nucleic acid molecule encoding the light chain or the heavy chain of an antibody as described hereinabove. In one embodiment the nucleic acid molecule encodes the light chain or the heavy chain of a fully human monoclonal antibody. Still another embodiment is a nucleic acid molecule encoding the light chain or the heavy chain of a fully human monoclonal antibody selected from antibodies 2.19.2, 2.6.1 or 4.18.1.

Another embodiment of the invention is a vector comprising a nucleic acid molecule or molecules as described hereinabove, wherein the vector encodes a targeted binding agent as defined hereinabove. In one embodiment of the invention is a vector comprising a nucleic acid molecule or molecules as described hereinabove, wherein the vector encodes a light chain and/or a heavy chain of an antibody as defined hereinabove.

Yet another embodiment of the invention is a host cell comprising a vector as described hereinabove. Alternatively the host cell may comprise more than one vector.

In addition, one embodiment of the invention is a method of producing a targeted binding agent or of the invention by culturing host cells under conditions wherein a nucleic acid molecule is expressed to produce the targeted binding agent, followed by recovery of the targeted binding agent. In one embodiment of the invention is a method of producing an antibody of the invention by culturing host cells under conditions wherein a nucleic acid molecule is expressed to produce the antibody, followed by recovery of the antibody.

In one embodiment the invention includes a method of making an targeted binding agent by transfecting at least one host cell with at least one nucleic acid molecule encoding the targeted binding agent as described hereinabove, expressing the nucleic acid molecule in the host cell and isolating the targeted binding agent. In one embodiment the invention includes a method of making an antibody by transfecting at least one host cell with at least one nucleic acid molecule encoding the antibody as described hereinabove, expressing the nucleic acid molecule in the host cell and isolating the antibody.

According to another aspect, the invention includes a method of antagonising the biological activity of uPAR by administering an antagonist as described herein. The method may include selecting an animal in need of treatment for disease-related cell adhesion and/or invasion, and administering to the animal a therapeutically effective dose of an antagonist of the biological activity of uPAR.

Another aspect of the invention includes a method of antagonising the biological activity of uPAR by administering a targeted binding agent as described hereinabove. The method may include selecting an animal in need of treatment for disease-related cell adhesion and/or invasion, and administering to the animal a therapeutically effective dose of a targeted binding agent which antagonises the biological activity of uPAR.

Another aspect of the invention includes a method of antagonising the biological activity of uPAR by administering an antibody as described hereinabove. The method may include selecting an animal in need of treatment for disease-related cell adhesion and/or invasion, and administering to the animal a therapeutically effective dose of an antibody which antagonises the biological activity of uPAR.

According to another aspect there is provided a method of treating disease-related cell adhesion and/or invasion in a mammal by administering a therapeutically effective amount of an antagonist of the biological activity of uPAR. The method may include selecting an animal in need of treatment for disease-related cell adhesion and/or invasion, and administering to the animal a therapeutically effective dose of an antagonist of the biological activity of uPAR.

According to another aspect there is provided a method of treating disease-related cell adhesion and/or invasion in a mammal by administering a therapeutically effective amount of a targeted binding agent which antagonizes the biological activity of uPAR. The method may include selecting an animal in need of treatment for disease-related cell adhesion and/or invasion, and administering to the animal a therapeutically effective dose of a targeted binding agent which antagonises the biological activity of uPAR. The targeted binding agent can be administered alone, or can be administered in combination with additional antibodies or chemotherapeutic drugs or radiation therapy.

According to another aspect there is provided a method of treating disease-related cell adhesion and/or invasion in a mammal by administering a therapeutically effective amount of an antibody which antagonizes the biological activity of uPAR. The method may include selecting an animal in need of treatment for disease-related cell adhesion and/or invasion, and administering to the animal a therapeutically effective dose of an antibody which antagonises the biological activity of uPAR. The antibody can be administered alone, or can be administered in combination with additional antibodies or chemotherapeutic drugs or radiation therapy.

According to another aspect there is provided a method of treating cancer in a mammal by administering a therapeutically effective amount of an antagonist of the biological activity of uPAR. The method may include selecting an animal in need of treatment for cancer, and administering to the animal a therapeutically effective dose of an antagonist which antagonises the biological activity of uPAR. The antagonist can be administered alone, or can be administered in combination with additional antibodies or chemotherapeutic drugs or radiation therapy.

According to another aspect there is provided a method of treating cancer in a mammal by administering a therapeutically effective amount of a targeted binding agent which antagonizes the biological activity of uPAR. The method may include selecting an animal in need of treatment for cancer, and administering to the animal a therapeutically effective dose of a targeted binding agent which antagonises the biological activity of uPAR. The targeted binding agent can be administered alone, or can be administered in combination with additional antibodies or chemotherapeutic drugs or radiation therapy.

According to another aspect there is provided a method of treating cancer in a mammal by administering a therapeutically effective amount of an antibody which antagonizes the biological activity of uPAR. The method may include selecting an animal in need of treatment for cancer, and administering to the animal a therapeutically effective dose of an antibody which antagonises the biological activity of uPAR. The antibody can be administered alone, or can be administered in combination with additional antibodies or chemotherapeutic drugs or radiation therapy.

According to another aspect of the invention there is provided the use of an antagonist of the biological activity of uPAR for the manufacture of a medicament for the treatment of disease-related cell adhesion and/or invasion.

According to another aspect of the invention there is provided the use of a targeted binding agent which antagonizes the biological activity of uPAR for the manufacture of a medicament for the treatment of disease-related cell adhesion and/or invasion.

According to another aspect of the invention there is provided the use of an antibody which antagonizes the biological activity of uPAR for the manufacture of a medicament for the treatment of disease-related cell adhesion and/or invasion.

In one embodiment the present invention is particularly suitable for use in antagonizing uPAR, in patients with a tumor which is dependent alone, or in part, on a uPAR receptor.

Another embodiment of the invention includes an assay kit for detecting uPAR in mammalian tissues, cells, or body fluids to screen for cell adhesion- and invasion-related diseases. The kit includes a targeted binding agent that binds to uPAR and a means for indicating the reaction of the targeted binding agent with uPAR, if present. In one embodiment, the targeted binding agent that binds uPAR is labeled. In another embodiment the targeted binding agent is an unlabeled and the kit further includes a means for detecting the targeted binding agent. Preferably the targeted binding agent is labeled with a marker selected from the group consisting of a fluorochrome, an enzyme, a radionuclide and a radio-opaque material.

Another embodiment of the invention includes an assay kit for detecting uPAR in mammalian tissues, cells, or body fluids to screen for cell adhesion- and invasion-related diseases. The kit includes an antibody that binds to uPAR and a means for indicating the reaction of the antibody with uPAR, if present. The antibody may be a monoclonal antibody. In one embodiment, the antibody that binds uPAR is labeled. In another embodiment the antibody is an unlabeled primary antibody and the kit further includes a means for detecting the primary antibody. In one embodiment, the means includes a labeled second antibody that is an anti-immunoglobulin. Preferably the antibody is labeled with a marker selected from the group consisting of a fluorochrome, an enzyme, a radionuclide and a radio-opaque material.

Further embodiments, features, and the like regarding anti-uPAR antibodies are provided in additional detail below.

Sequence Listing

Embodiments of the invention include the specific anti-uPAR antibodies listed below in Table 1. This table reports the identification number of each anti-uPAR antibody, along with the SEQ ID number of the variable domain of the corresponding heavy chain and light chain genes. Each antibody has been given an identification number that includes three numbers separated by two decimal points.

TABLE 1

| mAb ID No.: | Sequence | SEQ ID NO: |
|---|---|---|
| 1.4.2 | Nucleotide sequence encoding the variable region of the heavy chain | 1 |
| | Amino acid sequence encoding the variable region of the heavy chain | 2 |
| | Nucleotide sequence encoding the variable region of the light chain | 3 |
| | Amino acid sequence encoding the variable region of the light chain | 4 |
| 1.41.1 | Nucleotide sequence encoding the variable region of the heavy chain | 5 |
| | Amino acid sequence encoding the variable region of the heavy chain | 6 |
| | Nucleotide sequence encoding the variable region of the light chain | 7 |
| | Amino acid sequence encoding the variable region of the light chain | 8 |
| 1.61.1 | Nucleotide sequence encoding the variable region of the heavy chain | 9 |
| | Amino acid sequence encoding the variable region of the heavy chain | 10 |

TABLE 1-continued

| mAb ID No.: | Sequence | SEQ ID NO: |
|---|---|---|
| | Nucleotide sequence encoding the variable region of the light chain | 11 |
| | Amino acid sequence encoding the variable region of the light chain | 12 |
| 1.99.1 | Nucleotide sequence encoding the variable region of the heavy chain | 13 |
| | Amino acid sequence encoding the variable region of the heavy chain | 14 |
| | Nucleotide sequence encoding the variable region of the light chain | 15 |
| | Amino acid sequence encoding the variable region of the light chain | 16 |
| 1.100.1 | Nucleotide sequence encoding the variable region of the heavy chain | 17 |
| | Amino acid sequence encoding the variable region of the heavy chain | 18 |
| | Nucleotide sequence encoding the variable region of the light chain | 19 |
| | Amino acid sequence encoding the variable region of the light chain | 20 |
| 1.113.2 | Nucleotide sequence encoding the variable region of the heavy chain | 21 |
| | Amino acid sequence encoding the variable region of the heavy chain | 22 |
| | Nucleotide sequence encoding the variable region of the light chain | 23 |
| | Amino acid sequence encoding the variable region of the light chain | 24 |
| 2.6.1 | Nucleotide sequence encoding the variable region of the heavy chain | 25 |
| | Amino acid sequence encoding the variable region of the heavy chain | 26 |
| | Nucleotide sequence encoding the variable region of the light chain | 27 |
| | Amino acid sequence encoding the variable region of the light chain | 28 |
| 2.19.2 | Nucleotide sequence encoding the variable region of the heavy chain | 29 |
| | Amino acid sequence encoding the variable region of the heavy chain | 30 |
| | Nucleotide sequence encoding the variable region of the light chain | 31 |
| | Amino acid sequence encoding the variable region of the light chain | 32 |
| 3.8.3 | Nucleotide sequence encoding the variable region of the heavy chain | 33 |
| | Amino acid sequence encoding the variable region of the heavy chain | 34 |
| | Nucleotide sequence encoding the variable region of the light chain | 35 |
| | Amino acid sequence encoding the variable region of the light chain | 36 |
| 3.176.2 | Nucleotide sequence encoding the variable region of the heavy chain | 37 |
| | Amino acid sequence encoding the variable region of the heavy chain | 38 |
| | Nucleotide sequence encoding the variable region of the light chain | 39 |
| | Amino acid sequence encoding the variable region of the light chain | 40 |
| 4.12.1 | Nucleotide sequence encoding the variable region of the heavy chain | 41 |
| | Amino acid sequence encoding the variable region of the heavy chain | 42 |
| | Nucleotide sequence encoding the variable region of the light chain | 43 |
| | Amino acid sequence encoding the variable region of the light chain | 44 |
| 4.13.1 | Nucleotide sequence encoding the variable region of the heavy chain | 45 |
| | Amino acid sequence encoding the variable region of the heavy chain | 46 |
| | Nucleotide sequence encoding the variable region of the light chain | 47 |
| | Amino acid sequence encoding the variable region of the light chain | 48 |
| 4.18.1 | Nucleotide sequence encoding the variable region of the heavy chain | 49 |
| | Amino acid sequence encoding the variable region of the heavy chain | 50 |
| | Nucleotide sequence encoding the variable region of the light chain | 51 |
| | Amino acid sequence encoding the variable region of the light chain | 52 |
| 4.19.1 | Nucleotide sequence encoding the variable region of the heavy chain | 53 |
| | Amino acid sequence encoding the variable region of the heavy chain | 54 |
| | Nucleotide sequence encoding the variable region of the light chain | 55 |
| | Amino acid sequence encoding the variable region of the light chain | 56 |
| 4.50.1 | Nucleotide sequence encoding the variable region of the heavy chain | 57 |
| | Amino acid sequence encoding the variable region of the heavy chain | 58 |
| | Nucleotide sequence encoding the variable region of the light chain | 59 |
| | Amino acid sequence encoding the variable region of the light chain | 60 |

DEFINITIONS

Unless otherwise defined, scientific and technical terms used herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art.

Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g. Sambrook et al. *Molecular Cloning: A Laboratory Manual* (3rd ed., Cold Spring Harbor Laboratory Press, Cold Spring Harbor, N.Y. (2001)), which is incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

An antagonist may be a polypeptide, nucleic acid, carbohydrate, lipid, small molecular weight compound, an oligonucleotide, an oligopeptide, RNA interference (RNAi), antisense, a recombinant protein, an antibody, or fragments thereof or conjugates or fusion proteins thereof. For a review of RNAi see Milhavet O. Gary D S, Mattson M P. (Pharmacol Rev. 2003 December; 55(4):629-48. Review.) and antisense see Opalinska J B, Gewirtz A M. (Sci STKE. 2003 Oct. 28; 2003 (206):pe47.)

Disease-related cell adhesion and/or invasion may be any abnormal, undesirable or pathological cell adhesion and/or invasion, for example tumor-related cell adhesion and/or invasion. Cell adhesion- and/or invasion-related diseases include, but are not limited to, non-solid tumors such as leukemia, multiple myeloma or lymphoma, and also solid tumors such as melanoma, small cell lung cancer, non-small cell lung cancer, glioma, hepatocellular (liver) carcinoma, glioblastoma, carcinoma of the thyroid, bile duct, bone, gastric, brain/CNS, head and neck, hepatic system, stomach, prostate, breast, renal, testicle, ovary, skin, cervix, lung, muscle, neuron, oesophageal, bladder, lung, uterus, vulva, endometrium, kidney, colorectum, pancreas, pleural/peritoneal membranes, salivary gland, and epidermous.

A compound refers to any small molecular weight compound with a molecular weight of less than about 2000 Daltons.

The term "uPAR" refers to the molecule urokinase-type plasminogen activator receptor.

The term "neutralizing" when referring to an targeted binding agent such as an antibody relates to the ability of an antibody to eliminate, or significantly reduce, the activity of a target antigen. Accordingly, a "neutralizing" anti-uPAR antibody of the invention is capable of eliminating or significantly reducing the activity of uPAR. A neutralizing uPAR antibody may, for example, act by blocking the binding of uPA to its receptor uPAR. By blocking this binding, the uPA mediated plasminogen activation is significantly, or completely, eliminated. Ideally, a neutralizing antibody against uPAR inhibits cell adhesion and/or invasion.

The term "polypeptide" is used herein as a generic term to refer to native protein, fragments, or analogs of a polypeptide sequence. Hence, native protein, fragments, and analogs are species of the polypeptide genus. Preferred polypeptides in accordance with the invention comprise the human heavy chain immunoglobulin molecules and the human kappa light chain immunoglobulin molecules, as well as antibody molecules formed by combinations comprising the heavy chain immunoglobulin molecules with light chain immunoglobulin molecules, such as the kappa or lambda light chain immunoglobulin molecules, and vice versa, as well as fragments and analogs thereof. Preferred polypeptides in accordance with the invention may also comprise solely the human heavy chain immunoglobulin molecules or fragments thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described that are in a relationship permitting them to function in their intended manner. For example, a control sequence "operably linked" to a coding sequence is connected in such a way that expression of the coding sequence is achieved under conditions compatible with the control sequences.

The term "polynucleotide" as referred to herein means a polymeric form of nucleotides of at least 10 bases in length, either ribonucleotides or deoxynucleotides or a modified form of either type of nucleotide, or RNA-DNA hetero-duplexes. The term includes single and double stranded forms of DNA.

The term "oligonucleotide" referred to herein includes naturally occurring, and modified nucleotides linked together by naturally occurring, and non-naturally occurring linkages. Oligonucleotides are a polynucleotide subset generally comprising a length of 200 bases or fewer. Preferably, oligonucleotides are 10 to 60 bases in length and most preferably 12, 13, 14, 15, 16, 17, 18, 19, or 20 to 40 bases in length. Oligonucleotides are usually single stranded, e.g. for probes; although oligonucleotides may be double stranded, e.g. for use in the construction of a gene mutant. Oligonucleotides can be either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phosphoraniladate, phosphoroamidate, and the like. See e.g., LaPlanche et al. *Nucl. Acids Res.* 14:9081 (1986); Stec et al. *J. Am. Chem. Soc.* 106:6077 (1984); Stein et al. *Nucl. Acids Res.* 16:3209 (1988); Zon et al. *Anti-Cancer Drug Design* 6:539 (1991); Zon et al. *Oligonucleotides and Analogues: A Practical Approach*, pp. 87-108 (F. Eckstein, Ed., Oxford University Press, Oxford England (1991)); Stec et al. U.S. Pat. No. 5,151,510; Uhlmann and Peyman *Chemical Reviews* 90:543 (1990), the disclosures of which are hereby incorporated by reference. An oligonucleotide can include a label for detection, if desired.

Two amino acid sequences are "homologous" if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least about 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in *Atlas of Protein Sequence and Structure*, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. It should be appreciated that there can be differing regions of homology within two orthologous sequences. For example, the functional sites of mouse and human orthologues may have a higher degree of homology than non-functional regions.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence.

In contradistinction, the term "complementary to" is used herein to mean that the complementary sequence is homologous to all or a portion of a reference polynucleotide sequence. For illustration, the nucleotide sequence "TATAC"

corresponds to a reference sequence "TATAC" and is complementary to a reference sequence "GTATA".

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or amino acid residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more preferably at least 99 percent sequence identity, as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See *Immunology—A Synthesis* ($2^{nd}$ Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity. Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99% sequence identity to the antibodies or immunoglobulin molecules described herein. In particular, conservative amino acid replacements are contemplated. Conservative replacements are those that take place within a family of amino acids that have related side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are an aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding function or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. *Science* 253:164 (1991). Thus, the foregoing examples demonstrate that those of skill in the art can recognize sequence motifs and structural conformations that may be used to define structural and functional domains in accordance with the antibodies described herein.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W. H. Freeman and Company, New York (1984)); *Introduction to Protein Structure* (C. Branden and J. Tooze, eds., Garland Publishing, New York, N.Y. (1991)); and Thornton et at. *Nature* 354:105 (1991), which are each incorporated herein by reference.

The term "polypeptide fragment" as used herein refers to a polypeptide that has an amino-terminal and/or carboxy-terminal deletion, but where the remaining amino acid sequence is identical to the corresponding positions in the naturally-occurring sequence deduced, for example, from a full-length cDNA sequence. Fragments typically are at least 5, 6, 8 or 10 amino acids long, preferably at least 14 amino acids long, more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has at least one of the following properties: (1) specific binding to a uPAR, under suitable binding conditions, (2) ability to block appropriate uPA/uPAR binding, or (3) ability to inhibit uPA activity. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics". Fauchere, *J. Adv. Drug Res.* 15:29 (1986); Veber and Freidinger *TINS* p. 392 (1985); and Evans et al. *J. Med. Chem.* 30:1229 (1987), which are incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —$CH_2NH$—, —$CH_2S$—, —$CH_2$—$CH_2$—, —CH=CH— (cis and trans), —$COCH_2$—, —CH(OH)$CH_2$—, and —$CH_2SO$—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch *Ann. Rev. Biochem.* 61:387 (1992), incorporated herein by reference); for example, by adding internal cysteine residues capable of forming intramolecular disulfide bridges which cyclize the peptide.

As used herein, the term "antibody" refers to a polypeptide or group of polypeptides that are comprised of at least one binding domain that is formed from the folding of polypeptide chains having three-dimensional binding spaces with internal surface shapes and charge distributions complementary to the features of an antigenic determinant of an antigen. An antibody typically has a tetrameric form, comprising two identical pairs of polypeptide chains, each pair having one "light" and one "heavy" chain. The variable regions of each light/heavy chain pair form an antibody binding site.

As used herein, targeted binding agent, targeted binding protein, specific binding protein and like terms refer to an antibody, or binding fragment thereof, that preferentially binds to a target site. In one embodiment, the targeted binding agent is specific for only one target site. In other embodiments, the targeted binding agent is specific for more than one target site. In one embodiment, the targeted binding agent may be a monoclonal antibody and the target site may be an epitope.

"Binding fragments" of an antibody are produced by recombinant DNA techniques, or by enzymatic or chemical cleavage of intact antibodies. Binding fragments include Fab, Fab', F(ab')$_2$, Fv, Dab and single-chain antibodies. An antibody other than a "bispecific" or "bifunctional" antibody is understood to have each of its binding sites identical. An antibody substantially inhibits adhesion of a receptor to a counter-receptor when an excess of antibody reduces the quantity of receptor bound to counter-receptor by at least about 20%, 40%, 60% or 80%, and more usually greater than about 85% (as measured in an in vitro competitive binding assay).

An antibody may be oligoclonal, a polyclonal antibody, a monoclonal antibody, a chimeric antibody, a CDR-grafted antibody, a multi-specific antibody, a bi-specific antibody, a catalytic antibody, a chimeric antibody, a humanized antibody, a fully human antibody, an anti-idiotypic antibody and antibodies that can be labeled in soluble or bound form as well as fragments, variants or derivatives thereof, either alone or in combination with other amino acid sequences provided by known techniques. An antibody may be from any species. The term antibody also includes binding fragments of the antibodies of the invention; exemplary fragments include Fv, Fab, Fab', single stranded antibody (svFC), dimeric variable region (Diabody) and disulphide stabilized variable region (dsFv).

The term "epitope" includes any protein determinant capable of specific binding to an immunoglobulin or T-cell receptor. Epitopic determinants usually consist of chemically active surface groupings of molecules such as amino acids or sugar side chains and may, but not always, have specific three-dimensional structural characteristics, as well as specific charge characteristics. An antibody is said to specifically bind an antigen when the dissociation constant is $\leq 1$ µM, preferably $\leq 100$ nM and most preferably $\leq 10$ nM.

The term "agent" is used herein to denote a chemical compound, a mixture of chemical compounds, a biological macromolecule, or an extract made from biological materials.

"Active" or "activity" in regard to a uPAR polypeptide refers to a portion of an uPAR polypeptide that has a biological or an immunological activity of a native uPAR polypeptide. "Biological" when used herein refers to a biological function that results from the activity of the native uPAR polypeptide. A preferred uPAR biological activity includes, for example, uPAR induced cell adhesion and invasion.

"Mammal" when used herein refers to any animal that is considered a mammal. Preferably, the mammal is human.

Digestion of antibodies with the enzyme, papain, results in two identical antigen-binding fragments, known also as "Fab" fragments, and a "Fc" fragment, having no antigen-binding activity but having the ability to crystallize. Digestion of antibodies with the enzyme, pepsin, results in the a F(ab')$_2$ fragment in which the two arms of the antibody molecule remain linked and comprise two-antigen binding sites. The F(ab')$_2$ fragment has the ability to crosslink antigen.

"Fv" when used herein refers to the minimum fragment of an antibody that retains both antigen-recognition and antigen-binding sites.

"Fab" when used herein refers to a fragment of an antibody that comprises the constant domain of the light chain and the CH1 domain of the heavy chain.

"Dab" when used herein refers to a fragment of an antibody that is the smallest functional binding unit of a human antibodies.

The term "mAb" refers to monoclonal antibody.

"Liposome" when used herein refers to a small vesicle that may be useful for delivery of drugs that may include the uPAR polypeptide of the invention or antibodies to such an uPAR polypeptide to a mammal.

"Label" or "labeled" as used herein refers to the addition of a detectable moiety to a polypeptide, for example, a radiolabel, fluorescent label, enzymatic label chemiluminescent labeled or a biotinyl group. Radioisotopes or radionuclides may include $^3$H, $^{14}$C, $^{15}$N, $^{35}$S, $^{90}$Y, $^{99}$Tc, $^{111}$In, $^{125}$I, $^{131}$I, fluorescent labels may include rhodamine, lanthanide phosphors or FITC and enzymatic labels may include horseradish peroxidase, β-galactosidase, luciferase, alkaline phosphatase.

The term "pharmaceutical agent or drug" as used herein refers to a chemical compound or composition capable of inducing a desired therapeutic effect when properly administered to a patient. Other chemistry terms herein are used according to conventional usage in the art, as exemplified by *The McGraw-Hill Dictionary of Chemical Terms* (Parker, S., Ed., McGraw-Hill, San Francisco (1985)), (incorporated herein by reference).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term "patient" includes human and veterinary subjects.

Human Antibodies and Humanization of Antibodies

Human antibodies avoid some of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, fully human antibodies can be generated through the introduction of functional human antibody loci into a rodent, other mammal or animal so that the rodent, other mammal or animal produces fully human antibodies.

One method for generating fully human antibodies is through the use of XenoMouse® strains of mice that have been engineered to contain up to but less than 1000 kb-sized germline configured fragments of the human heavy chain locus and kappa light chain locus. See Mendez et al. *Nature Genetics* 15:146-156 (1997) and Green and Jakobovits *J. Exp. Med.* 188:483-495 (1998). The XenoMouse® strains are available from Abgenix, Inc. (Fremont, Calif.).

The production of the XenoMouse® strains of mice is further discussed and delineated in U.S. patent application Ser. No. 07/466,008, filed Jan. 12, 1990, Ser. No. 07/610,515, filed Nov. 8, 1990, Ser. No. 07/919,297, filed Jul. 24, 1992, Ser. No. 07/922,649, filed Jul. 30, 1992, Ser. No. 08/031,801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430,938, filed Apr. 27, 1995, Ser. No. 08/464,584, filed Jun. 5, 1995, Ser. No. 08/464,582, filed Jun. 5, 1995, Ser. No. 08/463,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. No. 08/724,752, filed Oct. 2, 1996, Ser. No. 08/759,620, filed Dec. 3, 1996, U.S. Publication 2003/0093820, filed Nov. 30, 2001 and U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2. See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, WO 98/24893, published Jun. 11, 1998, WO 00/76310, published Dec. 21, 2000. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more V$_H$ genes, one or more D$_H$ genes, one or more J$_H$ genes, a mu constant region, and usually a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661,016, 5,770,429, 5,789,650, 5,814,318, 5,877,397, 5,874,299, and 6,255,458 each to Lonberg and Kay, U.S. Pat. Nos. 5,591,669 and 6,023.010 to Krimpenfort and Berns, U.S. Pat. Nos. 5,612,205, 5,721,367, and 5,789,215 to Berns et al., and U.S. Pat. No. 5,643,763 to Choi and Dunn, and GenPharm International U.S. patent application Ser. No. 07/574,748, filed Aug. 29, 1990, Ser. No. 07/575,962, filed Aug. 31, 1990, Ser. No. 07/810,279, filed Dec. 17, 1991, Ser. No. 07/853,408, filed Mar. 18, 1992, Ser. No. 07/904,068, filed Jun. 23, 1992, Ser. No. 07/990,860, filed Dec. 16, 1992, Ser. No. 08/053,131, filed Apr. 26, 1993, Ser. No. 08/096,762, filed Jul. 22, 1993, Ser. No. 08/155,301, filed Nov. 18, 1993, Ser. No. 08/161,739, filed Dec. 3, 1993, Ser. No. 08/165,699, filed Dec. 10, 1993, 08/209,741, filed Mar. 9, 1994, the disclosures of which are hereby incorporated by reference. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175, the disclosures of which are hereby incorporated by reference in their entirety. See further Taylor et al., 1992, Chen et al., 1993, Tuaillon et al., 1993, Choi et al., 1993, Lonberg et al., (1994), Taylor et al., (1994), and Tuaillon et al., (1995), Fishwild et al., (1996), the disclosures of which are hereby incorporated by reference in their entirety.

Kirin has also demonstrated the generation of human antibodies from mice in which, through microcell fusion, large pieces of chromosomes, or entire chromosomes, have been introduced. See European Patent Application Nos. 773 288 and 843 961, the disclosures of which are hereby incorporated by reference. Additionally, KM™—mice, which are the result of cross-breeding of Kirin's Tc mice with Medarex's minilocus (Humab) mice have been generated. These mice possess the human IgH transchromosome of the Kirin mice and the kappa chain transgene of the Genpharm mice (Ishida et al., Cloning Stem Cells, (2002) 4:91-102).

Human antibodies can also be derived by in vitro methods. Suitable examples include but are not limited to phage display (CAT, Morphosys, Dyax, Biosite/Medarex, Xoma, Symphogen, Alexion (formerly Proliferon), Affimed) ribosome display (CAT), yeast display, and the like.

Preparation of Antibodies

Antibodies, as described herein, were prepared through the utilization of the XenoMouse® technology, as described below. Such mice, then, are capable of producing human immunoglobulin molecules and antibodies and are deficient in the production of murine immunoglobulin molecules and antibodies. Technologies utilized for achieving the same are disclosed in the patents, applications, and references disclosed in the background section herein. In particular, however, a preferred embodiment of transgenic production of mice and antibodies therefrom is disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. See also Mendez et al. *Nature Genetics* 15:146-156 (1997), the disclosure of which is hereby incorporated by reference.

Through the use of such technology, fully human monoclonal antibodies to a variety of antigens have been produced. Essentially, XenoMouse® lines of mice are immunized with an antigen of interest (e.g. uPAR), lymphatic cells (such as B-cells) are recovered from the hyper-immunized mice, and the recovered lymphocytes are fused with a myeloid-type cell line to prepare immortal hybridoma cell lines. These hybridoma cell lines are screened and selected to identify hybridoma cell lines that produced antibodies specific to the antigen of interest. Provided herein are methods for the production of multiple hybridoma cell lines that produce antibodies specific to uPAR. Further, provided herein are characterization of the antibodies produced by such cell lines, including nucleotide and amino acid sequence analyses of the heavy and light chains of such antibodies.

Alternatively, instead of being fused to myeloma cells to generate hybridomas, B cells can be directly assayed. For example, CD19+ B cells can be isolated from hyperimmune XenoMouse® mice and allowed to proliferate and differentiate into antibody-secreting plasma cells. Antibodies from the cell supernatants are then screened by ELISA for reactivity against the uPAR immunogen. The supernatants might also be screened for immunoreactivity against fragments of uPAR to further map the different antibodies for binding to domains of functional interest on uPAR. The antibodies may also be screened other related human receptors and against the rat, the mouse, and non-human primate, such as Cynomolgus monkey, orthologues of uPAR, the last to determine species cross-reactivity. B cells from wells containing antibodies of interest may be immortalized by various methods including fusion to make hybridomas either from individual or from pooled wells, or by infection with EBV or transfection by known immortalizing genes and then plating in suitable medium. Alternatively, single plasma cells secreting antibodies with the desired specificities are then isolated using a uPAR-specific hemolytic plaque assay (see for example Babcook et al., *Proc. Natl. Acad. Sci. USA* 93:7843-48 (1996)). Cells targeted for lysis are preferably sheep red blood cells (SRBCs) coated with the uPAR antigen.

In the presence of a B-cell culture containing plasma cells secreting the immunoglobulin of interest and complement, the formation of a plaque indicates specific uPAR-mediated lysis of the sheep red blood cells surrounding the plasma cell of interest. The single antigen-specific plasma cell in the center of the plaque can be isolated and the genetic information that encodes the specificity of the antibody is isolated from the single plasma cell. Using reverse-transcription followed by PCR (RT-PCR), the DNA encoding the heavy and light chain variable regions of the antibody can be cloned. Such cloned DNA can then be further inserted into a suitable expression vector, preferably a vector cassette such as a pcDNA, more preferably such a pcDNA vector containing the constant domains of immunglobulin heavy and light chain. The generated vector can then be transfected into host cells, e.g., BEK293 cells, CHO cells, and cultured in conventional nutrient media modified as appropriate for inducing transcription, selecting transformants, or amplifying the genes encoding the desired sequences.

In general, antibodies produced by the fused hybridomas were human IgG2 heavy chains with fully human kappa or lambda light chains. Antibodies described herein possess human IgG4 heavy chains as well as IgG2 heavy chains. Antibodies can also be of other human isotypes, including IgG1. The antibodies possessed high affinities, typically possessing a $K_d$ of from about $10^{-6}$ through about $10^{-12}$ M or below, when measured by solid phase and solution phase techniques. Antibodies possessing a KD of at least $10^{-11}$ M are preferred to inhibit the activity of uPAR.

As will be appreciated, antibodies can be expressed in cell lines other than hybridoma cell lines. Sequences encoding particular antibodies can be used to transform a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference). The transformation procedure used depends upon the host to be transformed. Methods for introducing heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Cell lines of particular preference are selected through determining which cell lines have high expression levels and produce antibodies with constitutive uPAR binding properties.

Based on the ability of mAbs to significantly neutralize uPAR activity (as demonstrated in the Examples below), these antibodies will have therapeutic effects in treating symptoms and conditions resulting from uPAR expression. In specific embodiments, the antibodies and methods herein relate to the treatment of symptoms resulting from uPAR induced cell adhesion, invasion and intracellular signalling.

According to another aspect of the invention there is provided a pharmaceutical composition comprising an antagonist of the biological activity of uPAR, and a pharmaceutically acceptable carrier. In one embodiment the antagonist comprises an antibody. According to another aspect of the invention there is provided a pharmaceutical composition comprising an antagonist of the biological activity of uPAR, and a pharmaceutically acceptable carrier. In one embodiment the antagonist comprises an antibody.

Anti-uPAR antibodies are useful in the detection of uPAR in patient samples and accordingly are useful as diagnostics for disease states as described herein. In addition, based on their ability to significantly inhibit uPA activity (as demonstrated in the Examples below), anti-uPAR antibodies have therapeutic effects in treating symptoms and conditions resulting from uPAR expression. In specific embodiments, the antibodies and methods herein relate to the treatment of symptoms resulting from uPAR induced cell adhesion, invasion and intracellular signalling. Further embodiments involve using the antibodies and methods described herein to treat cell adhesion- and invasion-related diseases including neoplastic diseases, such as, melanoma, small cell lung cancer, non-small cell lung cancer, glioma, hepatocellular (liver) carcinoma, thyroid tumor, gastric (stomach) cancer, prostate cancer, breast cancer, ovarian cancer, bladder cancer, lung cancer, glioblastoma, endometrial cancer, kidney cancer, colon cancer, and pancreatic cancer. The antibodies may also be useful in treating cell adhesion and/or invasion in arthritis, atherosclerosis and diseases involving angiogenesis.

Therapeutic Administration and Formulations

Embodiments of the invention include sterile pharmaceutical formulations of anti-uPAR antibodies that are useful as treatments for diseases. Such formulations would inhibit the binding of uPA to its receptor uPAR, thereby effectively treating pathological conditions where, for example, serum or tissue uPAR is abnormally elevated. Anti-uPAR antibodies preferably possess adequate affinity to potently inhibit uPA, and preferably have an adequate duration of action to allow for infrequent dosing in humans. A prolonged duration of action will allow for less frequent and more convenient dosing schedules by alternate parenteral routes such as subcutaneous or intramuscular injection.

Sterile formulations can be created, for example, by filtration through sterile filtration membranes, prior to or following lyophilization and reconstitution of the antibody. The antibody ordinarily will be stored in lyophilized form or in solution. Therapeutic antibody compositions generally are placed into a container having a sterile access port, for example, an intravenous solution bag or vial having an adapter that allows retrieval of the formulation, such as a stopper pierceable by a hypodermic injection needle.

The route of antibody administration is in accord with known methods, e.g., injection or infusion by intravenous, intraperitoneal, intracerebral, intramuscular, intraocular, intraarterial, intrathecal, inhalation or intralesional routes, direct injection to a tumor site, or by sustained release systems as noted below. The antibody is preferably administered continuously by infusion or by bolus injection.

An effective amount of antibody to be employed therapeutically will depend, for example, upon the therapeutic objectives, the route of administration, and the condition of the patient. Accordingly, it is preferred that the therapist titer the dosage and modify the route of administration as required to obtain the optimal therapeutic effect. Typically, the clinician will administer antibody until a dosage is reached that achieves the desired effect. The progress of this therapy is easily monitored by conventional assays or by the assays described herein.

Antibodies, as described herein, can be prepared in a mixture with a pharmaceutically acceptable carrier. This therapeutic composition can be administered intravenously or through the nose or lung, preferably as a liquid or powder aerosol (lyophilized). The composition may also be administered parenterally or subcutaneously as desired. When administered systemically, the therapeutic composition should be sterile, pyrogen-free and in a parenterally acceptable solution having due regard for pH, isotonicity, and stability. These conditions are known to those skilled in the art. Briefly, dosage formulations of the compounds described herein are prepared for storage or administration by mixing the compound having the desired degree of purity with pharmaceutically acceptable carriers, excipients, or stabilizers. Such materials are non-toxic to the recipients at the dosages and concentrations employed, and include buffers such as TRIS HCl, phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium and/or nonionic surfactants such as TWEEN, PLURONICS or polyethyleneglycol.

Sterile compositions for injection can be formulated according to conventional pharmaceutical practice as described in *Remington: The Science and Practice of Pharmacy* ($20^{th}$ ed, Lippincott Williams & Wilkens Publishers (2003)). For example, dissolution or suspension of the active compound in a pharmaceutically acceptable carrier such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice.

Suitable examples of sustained-release preparations include semipermeable matrices of solid hydrophobic polymers containing the polypeptide, which matrices are in the form of shaped articles, films or microcapsules. Examples of sustained-release matrices include polyesters, hydrogels (e.g., poly(2-hydroxyethyl-methacrylate) as described by Langer et al., *J. Biomed Mater. Res.*, (1981) 15:167-277 and Langer, *Chem. Tech.*, (1982) 12:98-105, or poly(vinylalcohol)), polylactides (U.S. Pat. No. 3,773,919, EP 58,481), copolymers of L-glutamic acid and gamma ethyl-L-glutamate (Sidman et al., *Biopolymers*, (1983) 22:547-556), non-degradable ethylene-vinyl acetate (Langer et al., supra), degradable lactic acid-glycolic acid copolymers such as the LUPRON Depot™ (injectable microspheres composed of lactic acid-glycolic acid copolymer and leuprolide acetate), and poly-D-(−)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through disulfide interchange, stabilization may be achieved by modifying sulfhydryl residues, lyophilizing from acidic solutions, controlling moisture content, using appropriate additives, and developing specific polymer matrix compositions.

Sustained-released compositions also include preparations of crystals of the antibody suspended in suitable formulations capable of maintaining crystals in suspension. These preparations when injected subcutaneously or intraperitoneally can produce a sustained release effect. Other compositions also include liposomally entrapped antibodies. Liposomes containing such antibodies are prepared by methods known per se: U.S. Pat. No. DE 3,218,121; Epstein et al., *Proc. Natl. Acad. Sci. USA*, (1985) 82:3688-3692; Hwang et al., *Proc. Natl. Acad. Sci. USA*, (1980) 77:4030-4034; EP 52,322; EP 36,676; EP 88,046; EP 143,949; 142,641; Japanese patent application 83-118008; U.S. Pat. Nos. 4,485,045 and 4,544,545; and EP 102,324.

The dosage of the antibody formulation for a given patient will be determined by the attending physician taking into consideration various factors known to modify the action of drugs including severity and type of disease, body weight, sex, diet, time and route of administration, other medications and other relevant clinical factors. Therapeutically effective dosages may be determined by either in vitro or in vivo methods.

An effective amount of the antibodies, described herein, to be employed therapeutically will depend, for example, upon the therapeutic objectives, the route of administration, and the condition of the patient. Accordingly, it is preferred for the therapist to titer the dosage and modify the route of administration as required to obtain the optimal therapeutic effect. A typical daily dosage might range from about 0.001 mg/kg, 0.01 mg/kg, 0.1 mg/kg, 1 mg/kg, 10 mg/kg to up to 100 mg/kg, 1000 mg/kg, 10000 mg/kg or more, depending on the factors mentioned above. Typically, the clinician will administer the therapeutic antibody until a dosage is reached that achieves the desired effect. The progress of this therapy is easily monitored by conventional assays or as described herein.

It will be appreciated that administration of therapeutic entities in accordance with the compositions and methods herein will be administered with suitable carriers, excipients, and other agents that are incorporated into formulations to provide improved transfer, delivery, tolerance, and the like. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." *Regul. Toxicol. Pharmacol.* 32(2): 210-8 (2000), Wang W. "Lyophilization and development of solid protein pharmaceuticals." *Int. J. Pharm.* 203(1-2):1-60 (2000), Charman W N "Lipids, lipophilic drugs, and oral drug delivery-some emerging concepts." *J Pharm Sci* 89(8):967-78 (2000), Powell et al. "Compendium of excipients for parenteral formulations" *PDA J Pharm Sci Technol.* 52:238-311 (1998) and the citations therein for additional information related to formulations, excipients and carriers well known to pharmaceutical chemists.

Design and Generation of Other Therapeutics

In accordance with the present invention and based on the activity of the antibodies that are produced and characterized herein with respect to uPAR, the design of other therapeutic modalities beyond antibody moieties is facilitated. Such modalities include, without limitation, advanced antibody therapeutics, such as bispecific antibodies, immunotoxins, and radiolabeled therapeutics, single domain antibodies, antibody fragments, such as a Fab, Fab', F(ab')$_2$, Fv or Dab, generation of peptide therapeutics, uPAR binding domains in novel scaffolds, gene therapies, particularly intrabodies, antisense therapeutics, and small molecules.

In connection with the generation of advanced antibody therapeutics, where complement fixation is a desirable attribute, it may be possible to sidestep the dependence on complement for cell killing through the use of bispecific antibodies, immunotoxins, or radiolabels, for example.

Bispecific antibodies can be generated that comprise (i) two antibodies one with a specificity to uPAR and another to a second molecule that are conjugated together, (ii) a single antibody that has one chain specific to uPAR and a second chain specific to a second molecule, or (iii) a single chain antibody that has specificity to uPAR and the other molecule. Such bispecific antibodies can be generated using techniques that are well known; for example, in connection with (i) and (ii) see e.g. Fanger et al. *Immunol Methods* 4:72-81 (1994) and Wright and Harris, supra. and in connection with (iii) see e.g. Traunecker et al. *Int. J. Cancer (Suppl.)* 7:51-52 (1992). In each case, the second specificity can be made to the heavy chain activation receptors, including, without limitation, CD16 or CD64 (see e.g. Deo et al. *Immunol. Today* 18:127 (1997)) or CD89 (see e.g. Valerius et al. *Blood* 90:4485-4492 (1997)).

In connection with immunotoxins, antibodies can be modified to act as immunotoxins utilizing techniques that are well known in the art. See e.g. Vitetta *Immunol Today* 14:252 (1993). See also U.S. Pat. No. 5,194,594. In connection with the preparation of radiolabeled antibodies, such modified antibodies can also be readily prepared utilizing techniques that are well known in the art. See e.g. Junghans et al. in *Cancer Chemotherapy and Biotherapy* 655-686 (2d edition, Chafner and Longo, eds., Lippincott Raven (1996)). See also U.S. Pat. Nos. 4,681,581, 4,735,210, 5,101,827, 5,102,990 (RE 35,500), 5,648,471, and 5,697,902.

Combinations

The anti-tumor treatment defined herein may be applied as a sole therapy or may involve, in addition to the compounds of the invention, conventional surgery or radiotherapy or chemotherapy. Such chemotherapy may include one or more of the following categories of anti tumor agents:

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumor antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD05530; International Patent Application WO 01/94341) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661), and metalloproteinase inhibitors like marimastat, other inhibitors of urokinase plasminogen activator receptor function or, inhibitors of cathepsins, inhibitors of serine proteases for example matriptase, hepsin, urokinase, inhibitors of heparanase);

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy) quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy)quinazoline (AZD2171; Example 240 within WO 00/47212), vatalanib (PTK787; WO 98/35985) and SU11248 (sunitinib; WO 01/60814), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumor cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumor cell lines and approaches using anti-idiotypic antibodies.

In one embodiment the anti-tumor treatment defined herein may involve, in addition to the compounds of the invention, treatment with other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumor antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin).

In one embodiment the anti-tumor treatment defined herein may involve, in addition to the compounds of the invention, treatment with gemcitabine.

Such conjoint treatment may be achieved by way of the simultaneous, sequential or separate dosing of the individual components of the treatment. Such combination products employ the compounds of this invention, or pharmaceutically acceptable salts thereof, within the dosage range described hereinbefore and the other pharmaceutically active agent within its approved dosage range.

EXAMPLES

The following examples, including the experiments conducted and results achieved are provided for illustrative purposes only and are not to be construed as limiting upon the teachings herein.

Example 1

Immunization and Titering

Immunization

Immunizations were conducted using soluble uPAR (recombinant human uPAR/His6, Cat. #807-UK-100, R&D Systems, Inc.) and cell-bound uPAR (B300.19 transfectants expressing human uPAR at the cell surface), respectively. For the generation of a B300.19 transfectant, human full length uPAR cDNA was inserted into the pcDNA 3 expression vector. B300.19 cells were transiently transfected via electroporation. Expression of human uPAR on the cell surface at a level suitable for immunization was confirmed by Fluorescence-Activated Cell Sorter (FACS) analysis. Ten μg/mouse for soluble protein for Campaign 1, and $1 \times 10^7$ cells/mouse of B300.19 transfected cells for Campaign 2, were used for immunization in XenoMouse™ according to the methods disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. The immunization programs are summarized in Table 2.

Selection of Animals for Harvest by Titer

Titers of the antibody against human uPAR were tested by FACS. At the end of the immunization program, fusions were performed using mouse myeloma cells and lymphocytes isolated from the spleens and lymph nodes of the immunized mice by means of electroporation, as described in Example 2.

TABLE 2

Summary of Immunization Programs

| Campaign | Group | Immunogen | Strain | No of mice | Immunization routes |
|---|---|---|---|---|---|
| 1 | 1 | Soluble uPAR (R&D 807-UK) | IgG2 | 10 | Fp, twice/wk, ×4 wks |
| 1 | 2 | Soluble uPAR (R&D 807-UK) | IgG4 | 10 | Fp, twice/wk, ×4 wks |
| 2 | 3 | Cell-bound uPAR (B300.19 transfectants) | IgG2 | 10 | Fp, twice/wk, ×4 wks |
| 2 | 4 | Cell-bound uPAR(B300.19) transfectants) | IgG4 | 10 | Fp, twice/wk, ×4 wks |

"Fp" refers to "foot pad"

Example 2

Recovery of Lymphocytes, B-Cell Isolations, Fusions and Generation of Hybridomas Immunized mice were sacrificed by cervical dislocation, and the draining lymph nodes harvested and pooled from each cohort. The lymphoid cells were dissociated by grinding in DMEM to release the cells from the tissues and the cells were suspended in DMEM. The cells were counted, and 0.9 ml DMEM per 100 million lymphocytes added to the cell pellet to resuspend the cells gently but completely. Using 100 μl of CD90+ magnetic beads per 100 million cells, the cells were labeled by incubating the cells with the magnetic beads at 4° C. for 15 minutes. The magnetically labeled cell suspension containing up to $10^8$ positive cells (or up to $2 \times 10^9$ total cells) was loaded onto a LS+ column and the column washed with DMEM. The total effluent was collected as the CD90-negative fraction (most of these cells were expected to be B cells).

The fusion was performed by mixing washed enriched B cells from above and nonsecretory myeloma P3X63Ag8.653 cells purchased from ATCC, cat. #CRL 1580 (Kearney et al, J. Immunol. 123, 1979, 1548-1550) at a ratio of 1:1. The cell mixture was gently pelleted by centrifugation at 800×g. After complete removal of the supernatant, the cells were treated with 2-4 mL of Pronase solution (CalBiochem, cat. #53702; 0.5 mg/ml in PBS) for no more than 2 minutes. Then 3-5 ml of FBS was added to stop the enzyme activity and the suspension was adjusted to 40 ml total volume using electro cell fusion solution, (ECFS, 0.3M Sucrose, Sigma, Cat #S7903, 0.1 mM Magnesium Acetate, Sigma, Cat #M2545, 0.1 mM Calcium Acetate, Sigma, Cat #C4705). The supernatant was removed after centrifugation and the cells were resuspended in 40 ml ECFS. This wash step was repeated and the cells again were resuspended in ECFS to a concentration of $2 \times 10^6$ cells/ml.

Electro-cell fusion was performed using a fusion generator (model ECM2001, Genetronic, Inc., San Diego, Calif.). The fusion chamber size used was 2.0 ml, using the following instrument settings:

Alignment condition: voltage: 50 V, time: 50 sec.
Membrane breaking at: voltage: 3000 V, time: 30 μsec
Post-fusion holding time: 3 sec After ECF, the cell suspensions were carefully removed from the fusion chamber under sterile conditions and transferred into a sterile tube containing the same volume of Hybridoma Culture Medium (DMEM, JRH Biosciences), 15% FBS (Hyclone), supplemented with L-glutamine, pen/strep, OPI (oxaloacetate, pyruvate, bovine insulin) (all from Sigma) and IL-6 (Boehringer Mannheim). The cells were incubated for 15-30 minutes at 37° C., and then centrifuged at 400×g (1000 rpm) for five minutes. The cells were gently resuspended in a small volume of Hybridoma Selection Medium (Hybridoma Culture Medium supplemented with 0.5×HA (Sigma, cat. #A9666)), and the volume adjusted appropriately with more Hybridoma Selection Medium, based on a final plating of $5 \times 10^6$ B cells total per 96-well plate and 200 μl per well. The cells were mixed gently and pipetted into 96-well plates and allowed to grow. On day 7 or 10, one-half the medium was removed, and the cells re-fed with Hybridoma Selection Medium.

Hybridomas were grown as routine in the selective medium. Exhaustive supernatants collected from the hybridomas that potentially produce anti-human uPAR antibodies were subjected to subsequent screening assays.

Example 3

Binding to Cell-Bound hu-uPAR

Binding of the antibodies to cell-bound uPAR was tested with the murine pre-B cell line B300.19 (ATCC) transfected to express human uPAR, and B300.19 parental cells as a control, using Fluorometric Microvolume Assay Technology (FMAT). 5,000 cells/well were employed for the assay. Mouse anti-human uPAR mAb (R& E Systems, MAB807) was used as positive control reagent, whereas, G2 KLH supernatant (1:10) was used as negative control reagent. The bound antibodies were detected using goat anti-human IgG Cy5 conjugate at 400 ng/ml (goat anti-mouse IgG Cy5 conjugate for mouse antibody control). The positive lines were confirmed by FACS analysis by detecting the bound antibodies with both goat anti-human κ-PE or goat anti-human γ-Cy5 conjugates, at 5 μg/ml and 2.5 μg/ml (both were purchased from Jackson Immune Research), respectively. For each dye stained, the ratio of the GeoMean values between positive and negative cells were tabulated. Ratios above 1.95 were considered as hits. The number of human γ and κ specific hits from each fusion are listed in Table 3.

TABLE 3

Number of Antibodies that bound to cell-bound hu-uPAR as confirmed by FACS analysis

| Fusions | No. specific γ/κ positive lines |
|---|---|
| 1 | 168 |
| 2 | 37 |
| 3 | 169 |
| 4 | 69 |
| Total | 443 |

Example 4

Competitive Binding

The ability of the antibodies to inhibit binding of human uPA to cell-bound uPAR was tested by FACS analysis in this assay. Briefly, murine fibroblast L929 cells (ATCC) were transfected to express human uPAR. Transfectants with 99% viability were incubated with 1:2 dilution of the supernatants at 4° C. overnight. After washing, the cells were incubated with 500 ng/ml FITC-labelled tc-uPA (purchased from Molecular Systems) for an hour. Bound FITC-uPA was detected using rabbit anti-FITC conjugated with biotin (2.5 μg/ml, purchased from Molecular Probes). To amplify the signal, a tertiary detection reagent, strapavidin-Cy5 conjugate (SA-Cy5, 2.5 μg/ml, purchased from Jackson Immune Research), was employed. Monoclonal anti-human uPAR antibody MAB807 (R&D Systems, neutralizing receptor-ligand binding) was used as positive control reagent.

A total of 433 supernatants from hybridoma lines (binders) were tested, and 50% of inhibition was considered as positive. The positive lines (neutralizers) from each fusion are summarized Table 4. Among the four fusions, there are 102 lines in total that were able to inhibit binding of uPA to uPAR.

TABLE 4

Number of Abs that inhibited uPA/uPAR binding

| Fusion | No. tested (binders) | No. neutralizers |
|---|---|---|
| 1 | 168 | 63 |
| 2 | 37 | 11 |
| 3 | 169 | 17 |
| 4 | 69 | 11 |
| Total | 443 | 102 |

Example 5

Cross-Reactivity to Non-Human Primates uPAR derived from cynomolgus monkey was cloned and expressed on the surface of CHOK1 cells. The binding of the antibodies to cell-bound cynomolgus uPAR (with parental cells as negative control) was tested by FACS analysis in this assay. A murine anti-human uPAR antibody MAB807 (R&D Systems) was employed as a positive control reagent. Briefly, CHOK1/cyno-uPAR transfectants with 99% viability were incubated with 1:2 dilution of the supernatants at 4° C. The bound human antibodies were detected using both goat anti-human γ chain Cy5 conjugate (5 μg/ml) and anti-human κ chain PE conjugate (2.5 μg/ml), both purchased from Jackson Immunology Research. For each dye stained, the ratio of the GeoMean values between positive and negative cells were found. The ratios above 1.95 were considered hits. Only the lines that demonstrated inhibitory activity to uPA/uPAR binding (neutralizers) were subjected to this assay. As summarized in Table 5, 90 out of 102 lines that were tested showed binding ability to cyno-uPAR expressed on the surface of CHOK1 cells. The cross-reactivity to cynomolgus monkey uPAR was confirmed after 30 candidates were cloned and purified, as shown in Example 12 below.

TABLE 5

Number of Abs that bound to cells expressing cynomolgus uPAR

| Fusion | No. tested (neutralizers) | No. of γ/κ positives (cyno reactive) |
|---|---|---|
| 1 | 63 | 59 |
| 2 | 11 | 8 |
| 3 | 17 | 14 |
| 4 | 11 | 9 |
| Totals: | 102 | 90 |

Example 6

Kinetic Assays

High Antigen (HA) Quantitation (ELISA)

ELISA plates were coated with a greater amount of uPAR in comparison with the Limited Antigen Quantitation assay described below (4.2 μg/nL). Sample containing antibody (Ab) was titrated on the uPAR-coated ELISA plates and was incubated overnight to allow Ab binding to approach equilibrium. Titration of Ab in sample covered a dilution range of 1:200 to 1:19,531. A standard curve of uPAR-specific antibody of known concentration was used to define the linear range of the assay. Data within the linear range were used to derive the relative concentration of uPAR-specific Ab in each titrated sample. The high uPAR concentration and the overnight incubation limited the effect of Ab affinity, allowing quantitation of the relative amount of uPAR-specific Ab present in each sample.

Limited Antigen (LA) Quantitation (ELISA)

ELISA plates were coated with a lower amount of uPAR in comparison with the High Antigen Quantitation assay described below (320, 160, 80, 40 and 20 ng/mL). Samples containing one concentration of antibody (Ab) (1:25 dilution) were incubated overnight to allow Ab binding to approach equilibrium. The low antigen concentration limited the effect of antibody concentration, allowing ranking of the antibodies based on their relative affinity.

102 lines that had the ability to inhibit uPA/uPAR binding (neutralizers), were tested by the HA/LA kinetics assay. The results were analyzed, in combination with the efficacy of uPA/uPAR binding inhibition and FACS-based binding. Table 6 summarizes the results for the 30 hybridoma lines that had the desired neutralizing activity and preferred binding kinetics.

Example 7

Specificity Study

The closest homologue to uPAR is human Ly6e (about 36% similarity). In this study, all antibodies that cross-reacted to Ly6e were identified and excluded.

Human Ly6e (Genbank Accession No. BC119709) was cloned and expressed in HEK293T cells according to standard protocols. Due to the lack of the appropriate detection antibody, the authenticity of the expression of Ly6e was confirmed by probing a myc tag fused on the molecule, as well as demonstrating the right molecular size of the expressed protein on a Western Blot using the same anti-myc antibody.

The reactivity of the antibodies to the HEK293T transfected to express Ly6e was determined by FACS analysis, using 1:2 hybridoma supernatants, and probed with goat anti-human γ chain conjugated with Cy5 (2.5 mg/ml, Jackson Immune Research). Binding of an anti-myc antibody (10 µg/ml, Invitrogen) to the transfectants served as a positive control, and binding of this antibody to the (Ly6e negative) parental cells served as the negative control. The GeoMean ratio to the positive vs negative at 1.95 was used as a threshold. Readings above 1.95 were considered as binders. As a result, among 102 neutralizers, only lines 4.67 and 4.50 were found to bind to Ly6e-expression cells. The others had no cross-reactivity to Ly6e. Table 6 summarizes properties of 30 lines selected for cloning.

uPA/uPAR binding, and kinetics ranking, as summarized in Table 6. Among them, two lines did not bind on cyno-uPAR on the cell surface. None of the antibodies reacted with murine uPAR and none of the selected lines reacted with Ly6e, the closest homologue of uPAR.

These 30 lines were cloned and further characterized as described below.

Example 8

Plasminogen Activation Assay

Human histocytic lymphoma cell line U937 (ATCC), which is known to express uPAR, was employed for this assay. Upon binding to the cell surface uPAR, single chain urokinase type plasminogen activator (scuPA) can be activated into uPA, and can cleave plasminogen to plasmin. The latter cleaves D-Val-Leu-Lys 7-Amido-4-methylcoumarin (VLK-AMC, Sigma catalog number V3138) and releases the fluorescent AMC dye. Hence, the intensity of Fluorescence Unit in the assay system indicates the quantity of bound uPA to cell surface uPAR. The neutralizing mAbs against uPAR were expected to inhibit binding of scuPA, and thus, suppress the fluorescence.

U937 cells were maintained and propagated in RPMI 1640 medium with 2 mM L-glutamine adjusted to contain 1.5 g/L sodium bicarbonate, 4.5 g/L glucose, 10 mM HEPES, 1.0 mM sodium pyruvate, and 10% FBS at 37° C. with 5% $CO_2$.

TABLE 6

Summary on the Selection of 30 Lines for Cellular Cloning

| | Line ID | Ab concentration AVG (ug/ml) | Affinity Ranking LA at 80 ng/ml | Affinity Ranking LA at 20 ng/ml | Efficacy uPA/uPAR binding Inhibition % | Cell-based Binding gCy5 Geo Mean Pos Cells | Cyno Cross Reactivity |
|---|---|---|---|---|---|---|---|
| 1 | 1.100 | 65.95 | 2.15 | 0.27 | 78 | 521 | Yes |
| 2 | 1.113 | 25.2 | 1.8 | 0.53 | 75 | 511 | Yes |
| 3 | 1.159 | 15.9 | 2.12 | 0.33 | 75 | 491 | Yes |
| 4 | 1.163 | 33.87 | 2.64 | 0.34 | 73 | 410 | Yes |
| 5 | 1.2 | 13.53 | 1.89 | 0.56 | 74 | 388 | Yes |
| 6 | 1.20 | 35.22 | 1.37 | 0.2 | 74 | 467 | Yes |
| 7 | 1.35 | 8.61 | 1.1 | 0.34 | 75 | 497 | Yes |
| 8 | 1.4 | 9.01 | 0.66 | 0.16 | 69 | 419 | Yes |
| 9 | 1.41 | 13.1 | 1.48 | 0.27 | 74 | 422 | Yes |
| 10 | 1.52 | 3.7 | 2 | 0.27 | 74 | 516 | Yes |
| 11 | 1.61 | 62.64 | 1.99 | 0.27 | 69 | 559 | Yes |
| 12 | 1.76 | 13.06 | 1.47 | 0.4 | 75 | 538 | Yes |
| 13 | 1.85 | 5.74 | 1.61 | 0.26 | 74 | 494 | Yes |
| 14 | 2.19 | 6.88 | 2.65 | 0.65 | 85 | 445 | Yes |
| 15 | 2.6 | 2.8 | 3.58 | 0.63 | 80 | 455 | Yes |
| 16 | 3.104 | 31.79 | 0.25 | 0.16 | 74 | 302 | Yes |
| 17 | 3.133 | 113.62 | 0.32 | 0.07 | 72 | 440 | No |
| 18 | 3.14 | 33.27 | 0.51 | 0.08 | 74 | 317 | Yes |
| 19 | 3.140 | 68.55 | 1.6 | 0.4 | 69 | 418 | Yes |
| 20 | 3.167 | 1230.59 | 0.28 | 0.09 | 74 | 336 | No |
| 21 | 3.176 | 22.09 | 0.96 | 0.22 | 76 | 392 | Yes |
| 22 | 3.179 | 13.95 | 0.09 | 0.07 | 72 | 371 | Yes |
| 23 | 3.8 | 19.2 | 2.57 | 0.67 | 70 | 451 | Yes |
| 24 | 4.12 | 48.62 | 0.21 | 0.06 | 71 | 317 | Yes |
| 25 | 4.13 | 89.59 | 0.24 | 0.09 | 78 | 28.2 | Yes |
| 26 | 4.18 | 2.44 | 2.06 | 0.27 | 75 | 251 | Yes |
| 27 | 4.19 | 4.24 | 1.03 | 0.16 | 77 | 412 | Yes |
| 28 | 4.50 | 1.08 | 0.64 | 0.21 | 67 | 402 | Yes |
| 29 | 4.65 | 0.46 | 0.13 | 0.06 | 80 | 431 | Yes |
| 30 | 4.68 | 33.33 | 0.11 | 0.07 | 78 | 208 | Yes |

Through the primary and secondary screening assays, a total of 30 hybridoma lines were identified based on their ability to bind to the cell-bound human uPAR, inhibition of To perform the assay, U937 cells were seeded at the density of 60,000 cells/well into a V-bottom plate, and were washed with cold reaction buffer (0.05 M Tris.HCl, 0.1 M NaCl, pH=7.4, with 2% BSA) by spinning cells down at 1,500 rpm for 3 min. After resuspension, the cells were treated with mAbs at indicated final concentrations for one hour on ice. The treated cell suspensions were spiked with scuPA at a final concentration of 3 nM. The cell suspensions were incubated on ice for one hour prior to being washed with cold reaction buffer. 50 µl of 1 µM Glu-plasminogen and 400 µM VLK-AMC substrate were added to the cell suspensions whose volumes were adjusted to 200 µl. The mixtures were transferred to a FMAT plate for fluorescence determination with a Tecan reader.

30 mAbs were initially tested in the plasminogen activation assay. 15 candidates with higher plasminogen activation inhibitory activity than others were then selected for further testing. The dose-response relationship curves for the 15 selected mAbs were generated by testing their inhibitory activities at various concentrations, as indicated in FIG. 1. Tests were run in triplicate for each mAb concentration. A quantitative index, IC50, for each mAb is included in Table 11.

It was noticed that there was an obvious gap between the curves for antibodies 4.19.1 and 1.41.1. The curves on the left of the gap (including 8 mAbs, namely, 4.18.1, 4.50.2, 4.13.2, 4.12.2, 2.6.1, 1.99.1, 2.19.2, and 4.19.1) had higher efficacy and potency. They inhibited plasminogen activation at greater than 90% at concentrations as low as 1 µg/ml. Therefore, these 8 mAbs were selected for further characterization.

Example 9

Adhesion Assay

A 96-well microtiter plate was coated with vitronectin (5 µg/ml) in sodium phosphate (pH 9) at 4° C. overnight. The plate was then blocked with 3% BSA in room temperature for at least an hour. U937 cells were acid-stripped using 2.5 ml of 50 mM glycine-HCl and 100 mM NaCl (pH 3.0) on ice for 3 min. The acidic cell suspension was then neutralized by 0.5 ml of 500 mM HEPES and 100 mM NaCl (pH 7.0).

The cells were then washed twice with pre-warmed serum-free medium, and twice again with HBBS containing 1% BSA and free of $Mn^{2+}$, before they were finally resuspended in HBBS at 180,000 cells/100 µL. The acid-stripped cells were then incubated with a pre-chosen mAb at 10 µg/ml for 1 hour at 4° C. The cells were subsequently spiked with 25 nM scuPA.

50 µl of cells and their pre-chosen mAb were added into each of the vitronectin-coated wells in the microtiter plate. The cells were allowed to adhere to the plate at 37° C. for 40 min. Unbound cells were washed off using warm HBSS. The bound cells were frozen by placing the plate in −80° C. for 1 hour. The cells were than thawed at room temperature. 100 ml of the CyQuant dye/lysis buffer were added to each well, and the fluorescence was read at 485 nm excitation and 530 nm emission.

Figure 2:
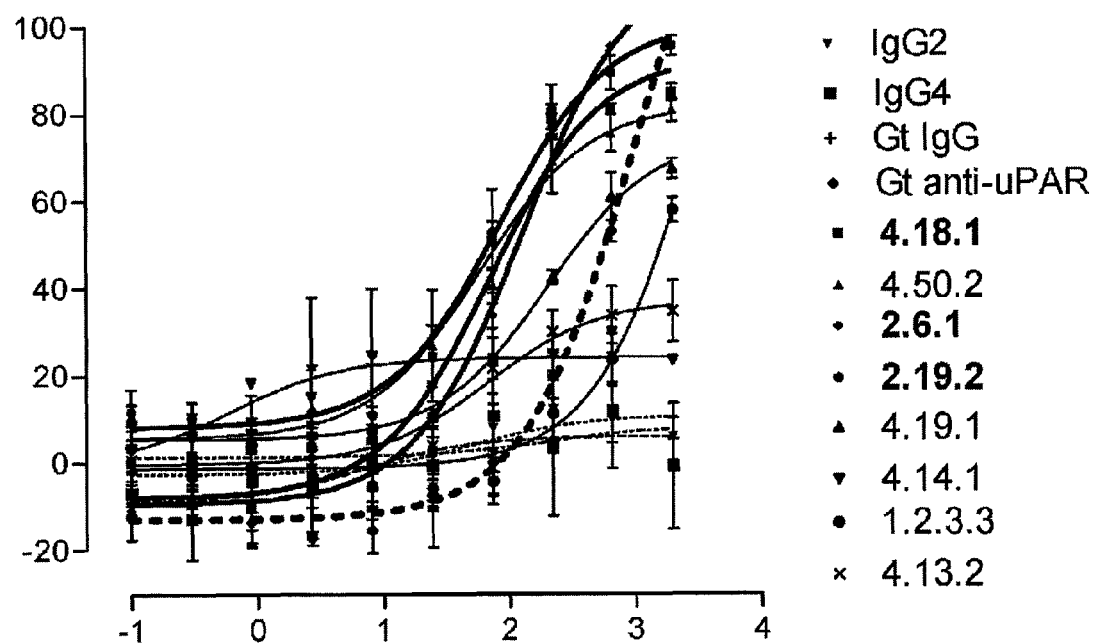
FIG. 2 is a line graph showing the ability of uPAR mAbs to inhibit adhesion of U937 cells to vitronectin. Shown are dose-response relationship curves for eight mAbs, as well as human and goat isotype negative controls and goat anti-uPAR positive control. Percent inhibition ("% Inhibition") is shown as a function of antibody concentration with units of Log [mAb] (ng/ml).

The 15 selected mAbs from Example 8 were subjected to the adhesion assay at 2 µg/ml initially. When 8 mAbs that inhibited adhesion were found, the dose-response relationship curves for them were obtained in triplicate, as illustrated in FIG. 2. The remaining 7 mAbs did not show an obvious inhibitory effect under the defined experimental conditions.

Neither human isotype IgGs nor goat IgG control inhibited adhesion of U937 to vitronectin. Similar to the goat anti-uPAR, which is a known neutralizer (black thick dot line, FIG. 2), these inhibitory 8 mAbs inhibited cell adhesion to vitronectin in a dose-dependent manner. The left-most group of the curves in the graph is composed of mAb 4.18.1, 2.6.1, 2.19.2, and 4.50.2. The maximum mAb concentration tested in the assay was 2 µg/ml. At this concentration, at least mAb 2.19.2 and 2.6.1 reach 90% of inhibition, and mAb 4.18.1 approaches 90% inhibition of uPAR-mediated cell adhesion to vitronectin. This experiment was repeated three times with similar results.

The correlation of the anti-adhesion activity to other features of the antibodies is summarized in Table 11.

Example 10

Invasion Assay

Matrigel™ (BD Biosciences Cat #356237 Lot #007024-7.7 mg/ml) was defrosted on ice in a 4° C. refrigerator overnight. 80 µl of the gel was added to each well in a BD 24-well Transwell Plate with pore size of 8 µm, and incubated at 37° C. for 90 min prior to cell attachment. HT-1080 cells were re-suspended using cell-dissociation solution (Sigma) at $1 \times 10^5$ cell/ml in DMEM (0.2% FCS) media. 100 µl ($1 \times 10^4$ cells) of the cell suspension was aliquoted to sterile eppendorf tubes and pre-incubated with the mAbs at final concentrations of 0.1, 1.0, and 10 µg/ml at 37° C. for 1 hour with occasional mixing. Untreated control samples were also pre-incubated at 37° C. for 1 hour with occasional mixing.

750 µl of DMEM (10% FCS) media supplemented with the mAbs at 0.1, 1.0, and 10 µg/ml was added to the appropriate wells of lower transwell chamber. 750 µl of DMEM (10% FCS) media was added to lower chamber of control samples. The upper chambers containing solidified Matrigel™ were inserted into lower transwell chambers, and 100 µl ($1 \times 10^4$ cells) of pre-incubated cell suspension was aliquoted to the upper chamber of appropriate wells, and the chambers were incubated at 37° C. for 3 days. The transwells were fixed by immersing in −20° C. methanol for 20 minutes at room temperature. The transwells were washed twice in PBS before being stained with Hoechst 33342 (Sigma catalog number B2261) (10 µM). After staining, the wells were washed twice with PBS. Using a 20× objective, optical images of cells on top of Matrigel™ and invaded cells at sequential 20 µm sections through the Matrigel™ were obtained. Image-ProPlus (Media Cybernetics, Bethesda, Md.) image analysis software package was employed to calculate cell number at each section. For each sample, data were presented as the percentage number of cells present in all sections that had invaded over a specified distance (60-200 µm).

Figure 3A:
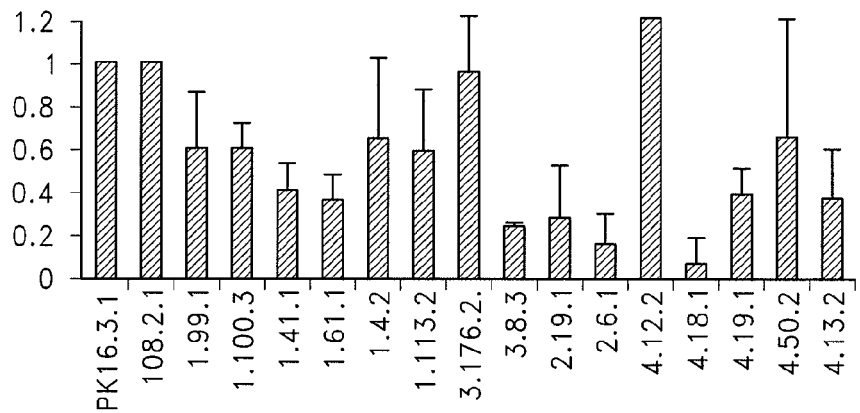
FIGS. 3A-C show the inhibitory effect of uPAR mAbs on HT-1080 invasion through Matrigel™ membrane preparation. The antibodies at concentrations of 0.1 μg/ml (3A), 1.0 μg/ml (3B), and 10 μg/ml (3C) were tested. The ratios of cell numbers that invade into the Matrigel™ beyond 60 micrometer (μm) with treatment versus isotype control are plotted.
Figure 3B:
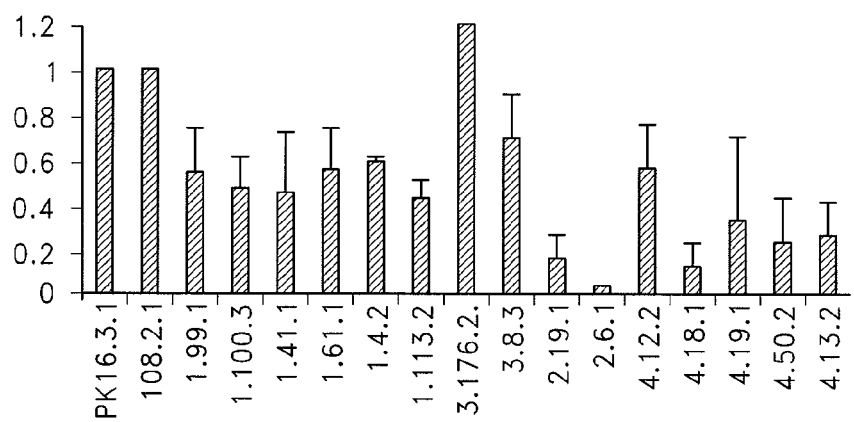
Figure 3C:
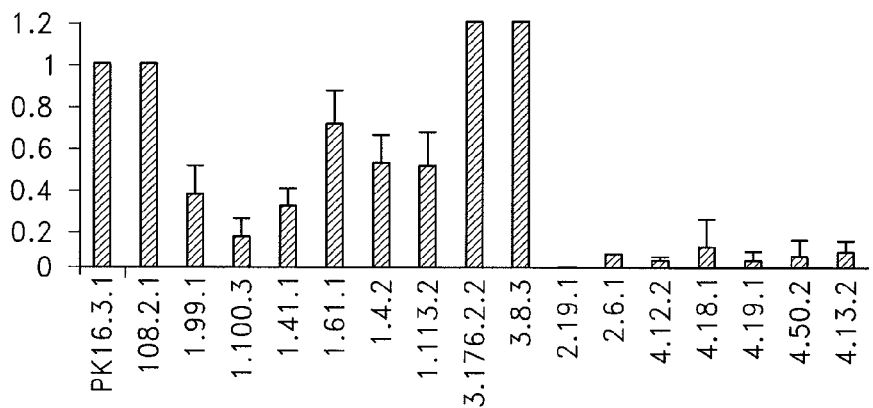
Figure 5:
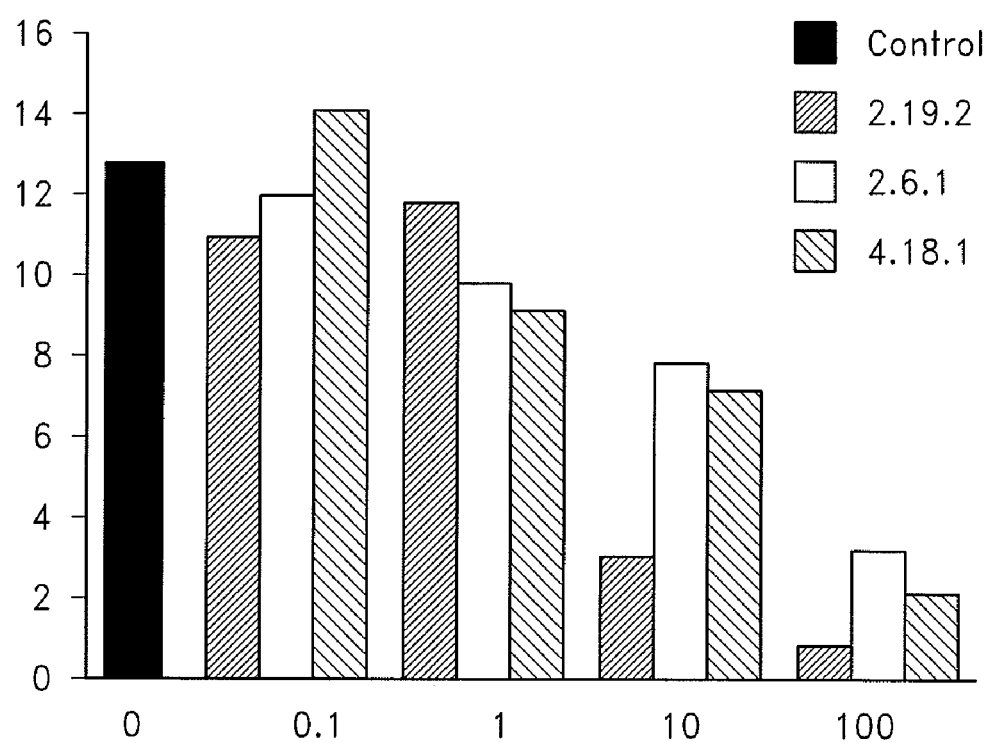
FIG. 5 is a bar graph showing the effect of anti-uPAR mAbs on tumor cell invasion. The percentage of HT-1080 cells invading through Matrigel™ beyond 80 micrometer (μM) is shown for each antibody at concentrations ranging from 0.1 to 100 ng/ml is shown.

The 15 mAbs from Example 8, together with isotype controls (PK16.3.1 for IgG2, 108.2.1 for IgG4), were tested in the assay at the mAb concentration of 0.1, 1.0, and 10 µg/ml. The number of cells invading beyond 60 µm in distance was normalized to the "fold change over IgG2 and IgG4 isotype control." The three panels in FIG. 3 represent the data collected with mAb concentration at 0.1, 1.0, and 10 µg/ml, respectively, from top to bottom. Most of the mAbs tested were found to inhibit cell invasion. Antibodies 2.19.1, 2.6.1 and 4.18.1 had the best efficacy and potency. At a concentration of 10 µg/ml, mAb 2.19.1 completely inhibited invasion beyond a 60 µm distance, and both mAbs 2.6.1 and 4.18.1 achieved 90% inhibition. Subsequently, analysis of 2.6.1, 2.19.2 and 4.18.1 was carried out over the concentration range 0.1-100 ng per ml and invasion was determined by the number of cells invading through Matrigel™ at a depth of 80 µM. As demonstrated in FIG. 5, mAbs 2.6.1, 2.19.2 and 4.18.1 at a concentration of 100 ng/ml were found to significantly (>70% inhibition) inhibit cell migration to 80 µm.

Example 11

Determination of Affinity Using Low and High Resolution Biacore™

Low Resolution Biacore™

For the low resolution Biacore™ tests, a selection of 31 hybridoma cell line products or hybridoma supernatants were tested for affinity determination. A high-density goat anti-human antibody surface over a CM5 Biacore™ chip was prepared using routine amine coupling. All mAbs were diluted to approximately 6 μg/mL in HBS-P running buffer (10 mM HEPES [pH 7.4], 150 nM NaCl, 0.005% surfactant P20) containing 100 μg/ml BSA. Each mAb was captured on a separate flow cell using a 30-second contact time at 10 μL/min followed by a 5-minute wash at a 100 μL/min flow rate for stabilization of the mAb baseline. Next, hu-uPAR (R&D Systems, Lot ALH01402A) was injected at 312 nM (23° C.) over all surfaces for 90 sec., followed by a 5-minute dissociation (100 μL/min flow rate). Four mAbs were re-analyzed with a 4-minute hu-uPAR injection (312 nM, 50 μL/min flow rate). All antigen samples were prepared in the running buffer. The surfaces were regenerated after every capture/injection cycle with one 15-second pulse of 146 mM phosphoric acid (pH 1.5).

The baseline drift of a buffer injection prior to each antigen injection was subtracted for each cycle.

Data were fit globally to a 1:1 interaction model using CLAMP (David G. Myszka and Thomas Morton (1998) "CLAMP©: a biosensor kinetic data analysis program," TIBS 23, 149-150) to determine the binding kinetics. A mass transport coefficient was used in fitting the data. The kinetic analysis results are listed in Table 7a. The mAb supernatants used in the analysis are also indicated. MAbs are ranked from high to low affinity.

TABLE 7a

Affinity Determination Results for the Hybridoma Lines Derived from Low Resolution Biacore ™

| Sample | Amt. Captured (RU) | $k_a$ (M$^{-1}$s$^{-1}$) | $k_d$ (s$^{-1}$) | $K_D$ (nM) |
|---|---|---|---|---|
| 2.19 | 299 | $1.4 \times 10^5$ | $4.3 \times 10^{-5}$ | 0.31 |
| 2.6 | 290 | $8.1 \times 10^4$ | $4.6 \times 10^{-5}$ | 0.57 |
| 3.29 | 249 | $2.7 \times 10^4$ | $3.1 \times 10^{-5}$ | 1.1 |
| 4.18 | 384 | $1.1 \times 10^5$ | $1.6 \times 10^{-4}$ | 1.5 |
| 4.50 | 298 | $1.2 \times 10^5$ | $2.6 \times 10^{-4}$ | 2.2 |
| 1.100 | 566 | $7.5 \times 10^4$ | $1.7 \times 10^{-4}$ | 2.3 |
| 4.65 | 291 | $1.1 \times 10^5$ | $2.5 \times 10^{-4}$ | 2.3 |
| 1.61 | 459 | $9.4 \times 10^4$ | $2.5 \times 10^{-4}$ | 2.7 |
| 4.19 | 227 | $1.2 \times 10^5$ | $3.2 \times 10^{-4}$ | 2.7 |
| 3.140 | 443 | $7.0 \times 10^4$ | $2.1 \times 10^{-4}$ | 3.0 |
| 3.8 | 427 | $2.2 \times 10^4$ | $6.8 \times 10^{-5}$ | 3.1 |
| 3.104 | 228 | $8.7 \times 10^4$ | $3.0 \times 10^{-4}$ | 3.4 |
| 1.99 | 509 | $1.2 \times 10^5$ | $4.2 \times 10^{-4}$ | 3.5 |
| 3.14 | 274 | $9.8 \times 10^4$ | $3.4 \times 10^{-4}$ | 3.5 |
| 1.35 | 546 | $3.8 \times 10^4$ | $1.5 \times 10^{-4}$ | 3.9 |
| 1.41 | 718 | $3.3 \times 10^4$ | $1.3 \times 10^{-4}$ | 3.9 |
| 3.176 (supe) | 239 | $5.3 \times 10^4$ | $2.3 \times 10^{-4}$ | 4.3 |
| 3.117 (supe) | 459 | $9.8 \times 10^4$ | $4.3 \times 10^{-4}$ | 4.4 |
| 1.113 | 694 | $2.8 \times 10^4$ | $1.3 \times 10^{-4}$ | 4.6 |
| 1.85 | 434 | $3.0 \times 10^4$ | $1.4 \times 10^{-4}$ | 4.7 |
| 4.68 | 209 | $5.3 \times 10^4$ | $2.9 \times 10^{-4}$ | 5.5 |
| 1.20 | 224 | $7.7 \times 10^4$ | $4.5 \times 10^{-4}$ | 5.8 |
| 1.163 | 662 | $7.4 \times 10^3$ | $4.6 \times 10^{-5}$ | 6.2 |
| 1.2 (supe) | 464 | $1.7 \times 10^4$ | $1.3 \times 10^{-4}$ | 7.6 |
| 1.4 | 321 | $1.1 \times 10^5$ | $9.6 \times 10^{-4}$ | 8.7 |
| 1.159 | 975 | $1.6 \times 10^4$ | $1.4 \times 10^{-4}$ | 8.7 |
| 4.13 | 161 | $9.5 \times 10^4$ | $1.2 \times 10^{-3}$ | 12.6 |
| 4.12 | 154 | $6.3 \times 10^4$ | $1.3 \times 10^{-3}$ | 20.6 |
| 3.133 | 324 | $9.5 \times 10^4$ | $3.6 \times 10^{-3}$ | 37.9 |
| 3.179 | 308 | $5.4 \times 10^4$ | $2.2 \times 10^{-3}$ | 40.7 |
| 3.167 | 414 | $6.6 \times 10^4$ | $3.9 \times 10^{-3}$ | 59.1 |

Most Abs fit a 1:1 model very well. The off-rate data for mAbs 3.133 and 3.167 showed some complexity, but the kinetic parameters are acceptable estimates. The longer 4-minute injection time in the analysis of mAb 1.163 still did not produce significant curvature in the on-rate data because the association rate was slow (on the order of $10^3$ M$^{-1}$s$^{-1}$).

High Resolution Biacore™

Considering that most mAbs fit a 1:1 model very well, the affinity ranking derived from the line product low resolution Biacore™ was believed to be reliable. The $K_d$ determination using high resolution Biacore™ with three (3) cloned and purified mAbs was conducted in separate experiments.

Each of three purified mAbs (2.19.2, 2.6.1 and 4.18.1) were amine coupled on a different flow cell surface of a CM5 Biacore™ chip and tested for their binding affinity to human uPAR. All mAbs were diluted into 10 mM sodium acetate, pH 4.0 for immobilization. The running buffer and sample preparation buffer for all experiments were degassed HBS-P (10 mM HEPES [pH 7.4], 150 nM NaCl, 0.005% surfactant P20) containing 100 μg/mL BSA. All experiments were run at 23° C. with a flow rate of 100 μL/min. Serially diluted (2-fold) uPAR samples were randomly injected in triplicate for 90 seconds with several buffer injections interspersed for double referencing. A Biacore™ 2000 biosensor instrument was used for all high resolution experiments. Data were fit globally to a 1:1 interaction model with a term for mass transport included. The resulting $K_D$ values are summarized in Table 7b.

TABLE 7b

Affinity Determination Results for Cloned and Purified mAbs Derived from High Resolution Biacore ™

| mAb | $K_D$ (pM) |
|---|---|
| 2.19.2 | 175 |
| 2.6.1 | 249 |
| 4.18.1 | 446 |

The Kd values for antibodies 2.19.2, 2.6.1, and 4.18.1 were 175 pM, 249 pM, and 446 pM, respectively. The $K_d$ ranking of each antibody with high resolution Biacore™ was consistent with that obtained via low resolution Biacore™.

Example 12

Cross-Reactivity to Mouse and Monkey uPAR

For determination of the mouse cross-reactivity, the mAb's binding to human uPAR expressed on the surface of U937 cells was detected in a competition assay using excess soluble mouse uPAR. In the assay, excess amounts of the recombinant mouse uPAR were preincubated with the mAbs before the mAbs were exposed to the cells expressing uPAR. If a mAb cross-reacted with the mouse uPAR, the preincubation would mask the mAb, thus, it would not bind to human uPAR.

A mouse uPAR/human IgG Fc chimera (uPARHuIgG) (R&D Systems, catalog number 531-PA-100) was used for the mouse uPAR. 50 µl of each mAb at 1 µg/nL was mixed with equal volume of the mouse uPARHuIgG 40 µg/mL. The final concentrations of the mAbs and mouse uPAR were 500 ng/mL and 20 µg/mL, respectively (Approx. M, W. of Mo-uPARHuIg is 66-90 Kd). The mixture was in FACS buffer (PBS supplemented with 1% BSA and 0.05% NaN$_3$), and was incubated for 30 min. Subsequently, 20,000 U397 cells were added into the mixture for an additional 30 minute incubation on ice. At the end of incubation, unbound mAbs were intensively eliminated by washing five times using FACS buffer. The bound mAbs were detected with Cy5 (Cy5-bis-OSU, N,N'-biscarboxypentyl-5,5'-disulfonatoindodicarbocyanine, Amersham Life Science, catalog No. PA15000)-labeled goat anti-Hu IgG Fc (5.0 µg/nL) and 7AAD (5.0 µg/nL) using a FACSCalibur flow cytometer (BD Biosciences, San Jose, Calif.).

The results showed that the excess amounts of soluble recombinant mouse uPAR did not block the binding of any mAb to cell-bound human uPAR (data not shown), indicating that none of the mAbs cross-reacted to the mouse uPAR. To make the mouse cross-reactivity results conclusive, direct binding of the mAbs to cell-bound mouse uPAR was measured using FACS analysis. The mouse cell line derived from the connective tissue, NCTC L929, was employed for FACS analysis. The harvested cells were resuspended at 50,000 cells/well using FACS buffer into a V-bottom plate which was put on ice. The uPAR mAbs at the final concentration of 6.25 µg/ml were added into the wells, and incubated for 1 hour on ice. After washing, Cy5-labeled goat anti-human IgG Fc at 5 µg/ml and 7AAD at 5 µg/ml was added. The mixtures were incubated for 15 min on ice, washed and resuspended in cold FACS buffer for FACS analysis.

Table 8 summarizes the FACS results. The rat anti-uPAR, which cross-reacts with mouse antigen, generated a great shift with GeoMean of 248.07. In contrast, the GeoMean values for the mouse anti-uPAR mAb (lacks reactivity to mouse antigen), isotype controls from the rat, mouse, and human, together with the secondary antibodies for detection, ranged between 3.14 and 13.07. All the fully human uPAR mAbs showed a GeoMean between 9 and 12, comparable to the background seen in the above negative controls. It was therefore concluded that none of the mAbs bound to the cell surface mouse uPAR.

TABLE 8

Summary of the FACS Analysis Results.

| Sample | Sample ID | X Geo Mean | Controls | X Geo mean |
|---|---|---|---|---|
| 1 | 1.100.1 | 9.89 | rat anti-uPAR | 248.07 |
| 2 | 1.99.1 | 11.65 | Mo anti-uPAR | 3.14 |
| 4 | 4.19.1 | 9.59 | Hu IgG2 isotype | 8.88 |
| 5 | 4.50.2 | 8.92 | Hu IgG4 isotype | 8.5 |
| 6 | 4.12.2 | 8.97 | Hu 2' | 7.63 |
| 7 | 4.18.1 | 8.18 | rat isotype | 12.31 |
| 12 | 2.19.2 | 9.55 | rat 2' | 13.07 |
| 13 | 2.6.1 | 12.95 | Mo isotype | 3.31 |
| 14 | 1.61.1 | 9.7 | Mo 2' | 3.22 |
| 15 | 4.13.2 | 11.24 | | |
| 17 | 1.4.2 | 12.38 | | |
| 24 | 1.113.2 | 10.19 | | |
| 26 | 1.41.1 | 9.59 | | |
| 29 | 1.2.3.3 | 9.89 | | |
| 30 | 3.176.2.2 | 8.36 | | |

Prior to the cloning, two out of the 30 selected hybridoma lines (3.133 and 3.167) were shown to lack cross-reactivity to the monkey uPAR. After cloning, the cross-reactivity to the monkey uPAR expressed recombinantly on the surface of 293T cells was confirmed using FACS analysis. The FACS analysis results are summarized in FIG. 4.

Figure 4:
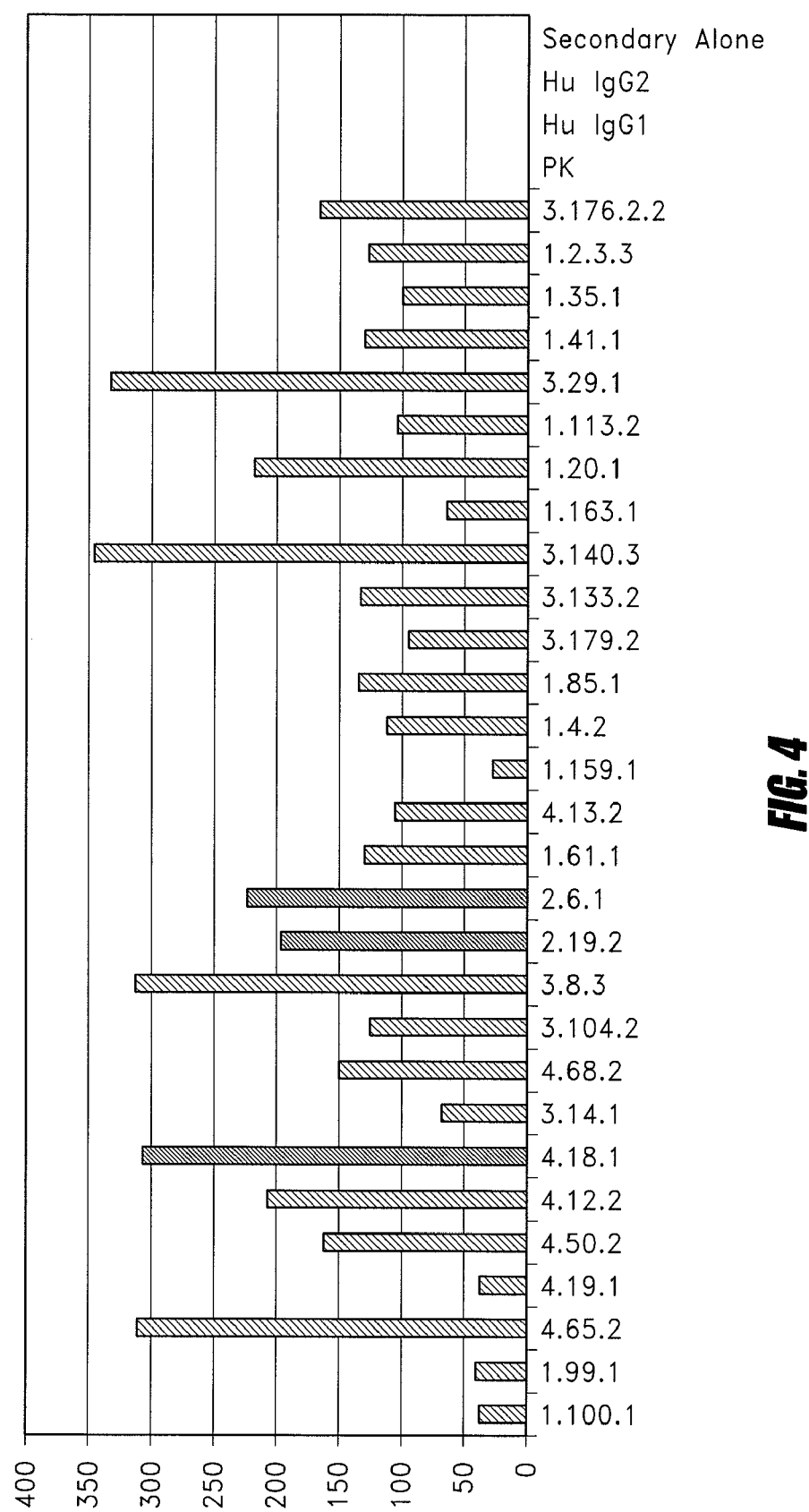
FIG. 4 is a bar graph showing binding of anti-uPAR monoclonal antibodies to monkey (cynomolgus) uPAR expressed on the surface of 293T cells. The GeoMean values derived from the FACS analysis of the histograph peak shift are plotted.

In comparison to the negative control antibodies, all the anti-uPAR mAbs bound to the cell-bound monkey uPAR, although the GeoMean values varied widely. Weak binders included mAbs 1.159.1, 1.163.1, 3.14.1 and mAb 1.100.1. Mabs 2.19.2, 2.6.1, and 4.18.1 were found to cross-react to the monkey antigen very strongly (FIG. 4).

Example 13

Cynomolgus Affinity

Kinetic measurements of several of the antibodies were evaluated using the KinExA® method. This method involves solution-based determination of formal affinity measurements at equilibrium. Recombinant human uPAR (amino acids 1-303) purchased from R&D systems was coupled to NHS-Sepharose beads. The remaining active groups on the beads were blocked with 10 mg/ml BSA in 1 M Tris and stored in the blocking solution as recommended by the manufacturer. KinExA experiments were performed using an automated flow immunoassay system, KinExA 3000, in which beads coupled with human uPAR served as the solid phase.

The nucleotide sequence shown as SEQ ID NO: 81 encodes the extracellular domain (ECD) of the cynomolgus protein with an in-frame His tag at the C-terminus (SEQ ID NO: 82). The cynomolgus uPAR was produced by transient transfection of an expression vector containing this nucleotide sequence in HEK293 cells using the Freestyle expression system (Invitrogen) of protein production as per manufacturer's recommendations. The conditioned media from this transient transfection was used for the affinity determination as described above.

Briefly, a constant amount of 2.6.1 or 2.19.2 anti-uPAR antibody (5 nM or 500 µM) was incubated with titrating concentrations of conditioned media containing recombinant cynomolgus uPAR ECD starting at approximately 625 nM. Antigen/antibody complexes were incubated at room temperature for 48 hrs to 168 hrs to allow equilibrium to be reached. The mixture was drawn through the human uPAR-coupled beads to accumulate unbound antibody. The captured antibody was detected using solutions containing a Cy5-conjugated goat anti-human IgG heavy and light chain specific secondary antibody in sample buffer. The bound signals were converted into relative values as a proportion of control in the absence of hIL-13. Three replicates of each sample were measured for all equilibrium experiments. The results are summarized in Table 9 below. The equilibrium dissociation constant ($K_D$) was obtained from nonlinear regression analysis of the data using a one-site homogeneous binding model with an unknown ligand concentration contained within the KinExA software. The software calculates the $K_D$ and determines the 95% confidence interval by fitting the data points to a theoretical $K_D$ curve. The 95% confidence interval is given as $K_D$ low and $K_D$ high.

TABLE 9

Summary of KinExA Results for Cynomolgus Binding Activity

| Antibody | $K_D$ | $K_D$ low | $K_D$ high |
|---|---|---|---|
| 2.6.1 | 1.09 nM | 478 pM | 2.46 nM |
| 2.19.2 | 346 pM | 234 pM | 508 pM |

Example 14

Internalization Assay

Eight of the mAbs from Example 8 were tested for the ability to induce uPAR internalization using U937 cells. A cell suspension containing 100,000 cells was pipetted into each well of a V-bottom plates in duplicate. Two V-bottom plates were prepared, one to be kept at 37° C. during internalization with antibody complex, and the other to be incubated at 4° C. Each of the eight uPAR mAbs was incubated with U937 cells at 5 μg/ml on ice for 15 min. Incubation on ice was necessary to prevent internalization of the primary mAbs. The cells were then washed with cold FACS buffer. Cells were subsequently incubated on ice in 100 μl of 5 μg/ml alexa647-labelled goat anti-humanF(ab) (Invitrogen catalogue number A21249) in cold FACS buffer for 15 min. This allowed the goat FAB bind to the bound uPAR mAbs without permitting any internalization. After a 15 minute incubation on ice, one plate was kept on ice, while the other plate was incubated at 37° C. for 1 hour.

Following the 1 hr incubation with the mAb-FAB complex, the cells were washed twice with cold 5% FACS buffer, and 200 μl of Tris(2-carboxyethyl)phosphine HCl (TCEP) was added to each well as a stripping agent. The plates were both incubated with TCEP on ice for 1 hour, followed by washing and resuspending with FACS buffer. 4 μl of 7-Amino-Actinomycin D (7AAD) was added to each well, followed by 10 min incubation on ice before FACS analysis was conducted.

The percentage of internalization was calculated using the following equation:

[(37 strip−4 strip)/(4 no strip−4 strip)]×100 where

'37 strip' is the geo mean at 37° C. with TCEP;

'4 strip' is the geo mean on ice with TCEP;

'4 no strip' is the geo mean on ice without TCEP (see Table 10).

TABLE 10

Summary of the Internalization Assay

| Antibody | geo mean cold + TCEP | geo mean cold − TCEP | geo mean 37° C. + TCEP | % Internalized |
|---|---|---|---|---|
| 2.19.2 | 2 | 42.67 | 3.54 | 3.7 |
| 4.50.2 | 2.01 | 42.12 | 3.2 | 2.9 |
| 4.12.2 | 2 | 33.35 | 3.02 | 3.2 |
| 1.99.1 | 1.95 | 42.49 | 2.69 | 1.8 |
| 2.6.1 | 2.07 | 44.34 | 3.02 | 2.2 |
| 4.13.2 | 1.95 | 37.42 | 2.95 | 2.8 |
| 4.19.1 | 2.34 | 45.95 | 5.31 | 6.8 |
| 4.18.1 | 2.05 | 41.2 | 3.25 | 3.0 |

As summarized in Table 10, very little, if any internalization was detected after 1 hour incubation at 37° C. The experiment was repeated twice with similar results.

Table 11 summarizes the results of the in vitro characterization for the candidates from Example 8.

TABLE 11

Summary of the in vitro Characterization Assay Results for Fifteen uPAR mAbs.

| Antibody (Clone no.) | Ab to cell bound Ag (line material, FACS) | Human uPAR/uPA binding inhibition (%, line material) | Plasminogen activation inhibition (IC50, ug/ml) | Cyno X-reactivity | Murine X-reactivity | Low Resolution Affinity (KD, nM) | High Resolution Affinity (Kd, nM) | Vitronectin adhesion | Invasion inhibition (Potency Ranking) |
|---|---|---|---|---|---|---|---|---|---|
| 2.19.2 | 445 | 85(1) | 0.053(1) | Y | N | 0.31(1) | 0.175(1) | +(1) | Y(1) |
| 2.6.1 | 455 | 80(1) | 0.073(4) | Y | N | 0.57(2) | 0.249(2) | +(4) | Y(2) |
| 4.18.1 | 251 | 75(7) | 0.067(3) | Y | N | 1.5(3) | 0.446(3) | +(3) | Y(3) |
| 1.99.1 | 514 | 78(3) | 0.066(2) | Y | N | 3.5 | ND | − | Y |
| 4.13.2 | 28.2 | 78(4) | 0.077(5) | Y | N | 12.6 | ND | + | Y |
| 4.50.2 | 402 | 67 | 0.104 | Y | N | 2.2 | ND | +(2) | Y |
| 4.12.2 | 317 | 71 | 0.067 | Y | N | 20.6 | ND | − | Y |
| 4.19.1 | 412 | 77 | 0.056 | Y | N | 2.7 | ND | + | Y |
| 1.41.1 | 422 | 74 | 0.181 | Y | N | 3.9 | ND | + | Y |
| 3.8.3 | 451 | 70 | 0.328 | Y | N | 3.1 | ND | − | Y |
| 1.4.2 | 419 | 69 | 0.075 | Y | N | 8.7 | ND | − | Y |
| 1.61.1 | 559 | 69 | 0.119 | Y | N | 2.7 | ND | − | Y |
| 1.100.1 | 521 | 78 | 0.061 | Y | N | 2.3 | ND | − | Y |
| 3.176.2 | 392 | 76 | 0.270 | Y | N | 4.3 | ND | − | N |
| 1.113.2 | 511 | 75 | 0.775 | Y | N | 4.6 | ND | − | N |

*The numbers in the parentheses indicate ranking order for each category.

Example 15

Structural Analysis of uPAR Antibodies

The variable heavy chains and the variable light chains of the antibodies were sequenced to determine their DNA sequences. The complete sequence information for the anti-uPAR antibodies is provided in the sequence listing with nucleotide and amino acid sequences for each gamma and kappa chain combination. The variable heavy sequences were analyzed to determine the VH family, the D-region sequence and the J-region sequence. The sequences were then translated to determine the primary amino acid sequence and compared to the germline VH, D and J-region sequences to assess somatic hypermutations.

Table 18 is a table comparing the antibody heavy chain regions to their cognate germ line heavy chain region. Table 19 is a table comparing the antibody kappa light chain regions to their cognate germ line light chain region.

The variable (V) regions of immunoglobulin chains are encoded by multiple germ line DNA segments, which are joined into functional variable regions ($V_H DJ_H$ or $V_K J_K$) during B-cell ontogeny. The molecular and genetic diversity of the antibody response to uPAR was studied in detail. These assays revealed several points specific to anti-uPAR antibodies.

It should be appreciated that amino acid sequences among the sister clones collected from each hybridoma are identical. As an example, the heavy chain and light chain sequences for mAb 2.19.3 would be identical to the sequences for mAbs 2.19 and 2.19.1.

According the sequencing data, the primary structure of the heavy chains of 2.6.1 and 4.18.1 are similar, but not identical. 2.19.2 is structurally different from the other two.

It should also be appreciated that where a particular antibody differs from its respective germline sequence at the amino acid level, the antibody sequence can be mutated back to the germline sequence. Such corrective mutations can occur at one, two, three or more positions, or a combination of any of the mutated positions, using standard molecular biological techniques. By way of non-limiting example, Table 19 shows that the light chain sequence of mAb 4.18.1 (SEQ ID NO.: 52) differs from the corresponding germline sequence (SEQ ID NO.:66) through a Ser to Phe mutation (mutation 1) in the FR1 region, a Val to Met mutation (mutation 2) in the FR1 region, a Lys to Thr mutation (mutation 3) in the FR2 region, a Ile to Phe mutation (mutation 4) in the FR3 region and a Ser to Ile mutation (mutation 5) in the FR3 region. Thus, the amino acid or nucleotide sequence encoding the light chain of mAb 4.18.1 can be modified to change mutation 1 to yield the germline sequence at the site of mutation 1. Further, the amino acid or nucleotide sequence encoding the light chain of mAb 4.18.1 can be modified to change mutation 2 or mutation 3 to yield the germline sequence at the site of mutation 2 or mutation 3. Still further, the amino acid or nucleotide sequence encoding the light chain of mAb 4.18.1 can be modified to change both mutation 1 and mutation 2, or any other combination of two or more mutations to yield the germline sequence at those particular sites. Tables 12-17 below illustrate the position of such variations from the germline for mAb 2.19.2, 2.6.1 and 4.18.1. Each row represents a unique combination of germline and non-germline residues at the position indicated by bold type.

TABLE 12

Exemplary Mutations of mAb 2.19.2 Light Chain (SEQ ID NO: 32) to Germline at the Indicated Residue Number.

| 12 | 32 | 36 | 38 | 100 | 101 | 103 |
|---|---|---|---|---|---|---|
| A | S | K | Y | DELETED | T | P |
| A | S | K | Y | DELETED | T | W |
| A | S | K | Y | DELETED | F | P |
| A | S | K | Y | DELETED | F | W |
| A | S | K | Y | I | T | P |
| A | S | K | Y | I | T | W |
| A | S | K | Y | I | F | P |
| A | S | K | Y | I | F | W |
| A | S | K | S | DELETED | T | P |
| A | S | K | S | DELETED | T | W |
| A | S | K | S | DELETED | F | P |
| A | S | K | S | DELETED | F | W |
| A | S | K | S | I | T | P |
| A | S | K | S | I | T | W |
| A | S | K | S | I | F | P |
| A | S | K | S | I | F | W |
| A | S | R | Y | DELETED | T | P |
| A | S | R | Y | DELETED | T | W |
| A | S | R | Y | DELETED | F | P |
| A | S | R | Y | DELETED | F | W |
| A | S | R | Y | I | T | P |
| A | S | R | Y | I | T | W |
| A | S | R | Y | I | F | P |
| A | S | R | Y | I | F | W |
| A | S | R | S | DELETED | T | P |
| A | S | R | S | DELETED | T | W |
| A | S | R | S | DELETED | F | P |
| A | S | R | S | DELETED | F | W |
| A | S | R | S | I | T | P |
| A | S | R | S | I | T | W |
| A | S | R | S | I | F | P |
| A | S | R | S | I | F | W |
| A | G | K | Y | DELETED | T | P |
| A | G | K | Y | DELETED | T | W |
| A | G | K | Y | DELETED | F | P |
| A | G | K | Y | DELETED | F | W |
| A | G | K | Y | I | T | P |
| A | G | K | Y | I | T | W |
| A | G | K | Y | I | F | P |
| A | G | K | Y | I | F | W |
| A | G | K | S | DELETED | T | P |
| A | G | K | S | DELETED | T | W |
| A | G | K | S | DELETED | F | P |
| A | G | K | S | DELETED | F | W |
| A | G | K | S | I | T | P |
| A | G | K | S | I | T | W |
| A | G | K | S | I | F | P |
| A | G | K | S | I | F | W |
| A | G | R | Y | DELETED | T | P |
| A | G | R | Y | DELETED | T | W |
| A | G | R | Y | DELETED | F | P |
| A | G | R | Y | DELETED | F | W |
| A | G | R | Y | I | T | P |
| A | G | R | Y | I | T | W |
| A | G | R | Y | I | F | P |
| A | G | R | Y | I | F | W |
| A | G | R | S | DELETED | T | P |
| A | G | R | S | DELETED | T | W |
| A | G | R | S | DELETED | F | P |
| A | G | R | S | DELETED | F | W |
| A | G | R | S | I | T | P |
| A | G | R | S | I | T | W |
| A | G | R | S | I | F | P |
| A | G | R | S | I | F | W |
| S | S | K | Y | DELETED | T | P |
| S | S | K | Y | DELETED | T | W |
| S | S | K | Y | DELETED | F | P |
| S | S | K | Y | DELETED | F | W |
| S | S | K | Y | I | T | P |
| S | S | K | Y | I | T | W |
| S | S | K | Y | I | F | P |
| S | S | K | Y | I | F | W |
| S | S | K | S | DELETED | T | P |
| S | S | K | S | DELETED | T | W |
| S | S | K | S | DELETED | F | P |
| S | S | K | S | DELETED | F | W |
| S | S | K | S | I | T | P |
| S | S | K | S | I | T | W |
| S | S | K | S | I | F | P |
| S | S | K | S | I | F | W |
| S | S | R | Y | DELETED | T | P |
| S | S | R | Y | DELETED | T | W |
| S | S | R | Y | DELETED | F | P |
| S | S | R | Y | DELETED | F | W |
| S | S | R | Y | I | T | P |
| S | S | R | Y | I | T | W |
| S | S | R | Y | I | F | P |
| S | S | R | Y | I | F | W |
| S | S | R | S | DELETED | T | P |
| S | S | R | S | DELETED | T | W |
| S | S | R | S | DELETED | F | P |
| S | S | R | S | DELETED | F | W |
| S | S | R | S | I | T | P |
| S | S | R | S | I | T | W |
| S | S | R | S | I | F | P |
| S | S | R | S | I | F | W |

TABLE 12-continued

Exemplary Mutations of mAb 2.19.2 Light Chain (SEQ ID NO: 32) to Germline at the Indicated Residue Number.

| 12 | 32 | 36 | 38 | 100 | 101 | 103 |
|----|----|----|----|-----|-----|-----|
| S | G | K | Y | DELETED | T | P |
| S | G | K | Y | DELETED | T | W |
| S | G | K | Y | DELETED | F | P |
| S | G | K | Y | DELETED | F | W |
| S | G | K | Y | I | T | P |
| S | G | K | Y | I | T | W |
| S | G | K | Y | I | F | P |
| S | G | K | Y | I | F | W |
| S | G | K | S | DELETED | T | P |
| S | G | K | S | DELETED | T | W |
| S | G | K | S | DELETED | F | P |
| S | G | K | S | DELETED | F | W |
| S | G | K | S | I | T | P |
| S | G | K | S | I | T | W |
| S | G | K | S | I | F | P |
| S | G | K | S | I | F | W |
| S | G | R | Y | DELETED | T | P |
| S | G | R | Y | DELETED | T | W |
| S | G | R | Y | DELETED | F | P |
| S | G | R | Y | DELETED | F | W |
| S | G | R | Y | I | T | P |
| S | G | R | Y | I | T | W |
| S | G | R | Y | I | F | P |
| S | G | R | Y | I | F | W |
| S | G | R | S | DELETED | T | P |
| S | G | R | S | DELETED | T | W |
| S | G | R | S | DELETED | F | P |
| S | G | R | S | DELETED | F | W |
| S | G | R | S | I | T | P |
| S | G | R | S | I | T | W |
| S | G | R | S | I | F | P |
| S | G | R | S | I | F | W |

TABLE 13

Exemplary Mutations of mAb 2.19.2 Heavy Chain (SEQ ID NO: 30) to Germline at the Indicated Residue Number.

| 99-100 |
|--------|
| DQ |
| DELETED |

TABLE 14

Exemplary Mutations of mAb 2.6.1 Light Chain (SEQ ID NO: 28) to Germline at the Indicated Residue Number.

| 95-96 | 103 |
|-------|-----|
| PL | K |
| PL | R |
| DELETED | K |
| DELETED | R |

TABLE 15

Exemplary Mutations of mAb 2.6.1 Heavy Chain (SEQ ID NO: 26) to Germline at the Indicated Residue Number.

| 30 | 31 | 35 | 50 | 53 | 58 | 69 | 81 | 87 | 98 |
|----|----|----|----|----|----|----|----|----|----|
| S | S | S | V | S | Y | I | Q | A | DELETED |
| S | S | S | V | S | Y | I | Q | A | E |
| S | S | S | V | S | Y | I | Q | V | DELETED |
| S | S | S | V | S | Y | I | Q | V | E |
| S | S | S | V | S | Y | I | H | A | DELETED |
| S | S | S | V | S | Y | I | H | A | E |

TABLE 15-continued

Exemplary Mutations of mAb 2.6.1 Heavy Chain (SEQ ID NO: 26) to Germline at the Indicated Residue Number.

| 30 | 31 | 35 | 50 | 53 | 58 | 69 | 81 | 87 | 98 |
|----|----|----|----|----|----|----|----|----|----|
| S | S | S | V | S | Y | I | H | V | DELETED |
| S | S | S | V | S | Y | I | H | V | E |
| S | S | S | V | S | Y | V | Q | A | DELETED |
| S | S | S | V | S | Y | V | Q | A | E |
| S | S | S | V | S | Y | V | Q | V | DELETED |
| S | S | S | V | S | Y | V | Q | V | E |
| S | S | S | V | S | Y | V | H | A | DELETED |
| S | S | S | V | S | Y | V | H | A | E |
| S | S | S | V | S | Y | V | H | V | DELETED |
| S | S | S | V | S | Y | V | H | V | E |
| S | S | S | V | S | S | I | Q | A | DELETED |
| S | S | S | V | S | S | I | Q | A | E |
| S | S | S | V | S | S | I | Q | V | DELETED |
| S | S | S | V | S | S | I | Q | V | E |
| S | S | S | V | S | S | I | H | A | DELETED |
| S | S | S | V | S | S | I | H | A | E |
| S | S | S | V | S | S | I | H | V | DELETED |
| S | S | S | V | S | S | I | H | V | E |
| S | S | S | V | S | S | V | Q | A | DELETED |
| S | S | S | V | S | S | V | Q | A | E |
| S | S | S | V | S | S | V | Q | V | DELETED |
| S | S | S | V | S | S | V | Q | V | E |
| S | S | S | V | S | S | V | H | A | DELETED |
| S | S | S | V | S | S | V | H | A | E |
| S | S | S | V | S | S | V | H | V | DELETED |
| S | S | S | V | S | S | V | H | V | E |
| S | S | S | V | T | Y | I | Q | A | DELETED |
| S | S | S | V | T | Y | I | Q | A | E |
| S | S | S | V | T | Y | I | Q | V | DELETED |
| S | S | S | V | T | Y | I | Q | V | E |
| S | S | S | V | T | Y | I | H | A | DELETED |
| S | S | S | V | T | Y | I | H | A | E |
| S | S | S | V | T | Y | I | H | V | DELETED |
| S | S | S | V | T | Y | I | H | V | E |
| S | S | S | V | T | Y | V | Q | A | DELETED |
| S | S | S | V | T | Y | V | Q | A | E |
| S | S | S | V | T | Y | V | Q | V | DELETED |
| S | S | S | V | T | Y | V | Q | V | E |
| S | S | S | V | T | Y | V | H | A | DELETED |
| S | S | S | V | T | Y | V | H | A | E |
| S | S | S | V | T | Y | V | H | V | DELETED |
| S | S | S | V | T | Y | V | H | V | E |
| S | S | S | V | T | S | I | Q | A | DELETED |
| S | S | S | V | T | S | I | Q | A | E |
| S | S | S | V | T | S | I | Q | V | DELETED |
| S | S | S | V | T | S | I | Q | V | E |
| S | S | S | V | T | S | I | H | A | DELETED |
| S | S | S | V | T | S | I | H | A | E |
| S | S | S | V | T | S | I | H | V | DELETED |
| S | S | S | V | T | S | I | H | V | E |
| S | S | S | V | T | S | V | Q | A | DELETED |
| S | S | S | V | T | S | V | Q | A | E |
| S | S | S | V | T | S | V | Q | V | DELETED |
| S | S | S | V | T | S | V | Q | V | E |
| S | S | S | V | T | S | V | H | A | DELETED |
| S | S | S | V | T | S | V | H | A | E |
| S | S | S | V | T | S | V | H | V | DELETED |
| S | S | S | V | T | S | V | H | V | E |
| S | S | S | I | S | Y | I | Q | A | DELETED |
| S | S | S | I | S | Y | I | Q | A | E |
| S | S | S | I | S | Y | I | Q | V | DELETED |
| S | S | S | I | S | Y | I | Q | V | E |
| S | S | S | I | S | Y | I | H | A | DELETED |
| S | S | S | I | S | Y | I | H | A | E |
| S | S | S | I | S | Y | I | H | V | DELETED |
| S | S | S | I | S | Y | I | H | V | E |
| S | S | S | I | S | Y | V | Q | A | DELETED |
| S | S | S | I | S | Y | V | Q | A | E |
| S | S | S | I | S | Y | V | Q | V | DELETED |
| S | S | S | I | S | Y | V | Q | V | E |
| S | S | S | I | S | Y | V | H | A | DELETED |
| S | S | S | I | S | Y | V | H | A | E |
| S | S | S | I | S | Y | V | H | V | DELETED |
| S | S | S | I | S | Y | V | H | V | E |
| S | S | S | I | S | S | I | Q | A | DELETED |

TABLE 15-continued

Exemplary Mutations of mAb 2.6.1 Heavy Chain (SEQ ID NO: 26) to Germline at the Indicated Residue Number.

| 30 | 31 | 35 | 50 | 53 | 58 | 69 | 81 | 87 | 98 |
|---|---|---|---|---|---|---|---|---|---|
| S | S | S | I | S | S | I | Q | A | E |
| S | S | S | I | S | S | I | Q | V | DELETED |
| S | S | S | I | S | S | I | Q | V | E |
| S | S | S | I | S | S | I | H | A | DELETED |
| S | S | S | I | S | S | I | H | A | E |
| S | S | S | I | S | S | I | H | V | DELETED |
| S | S | S | I | S | S | I | H | V | E |
| S | S | S | I | S | S | V | Q | A | DELETED |
| S | S | S | I | S | S | V | Q | A | E |
| S | S | S | I | S | S | V | Q | V | DELETED |
| S | S | S | I | S | S | V | Q | V | E |
| S | S | S | I | S | S | V | H | A | DELETED |
| S | S | S | I | S | S | V | H | A | E |
| S | S | S | I | S | S | V | H | V | DELETED |
| S | S | S | I | S | S | V | H | V | E |
| S | S | S | I | T | Y | I | Q | A | DELETED |
| S | S | S | I | T | Y | I | Q | A | E |
| S | S | S | I | T | Y | I | Q | V | DELETED |
| S | S | S | I | T | Y | I | Q | V | E |
| S | S | S | I | T | Y | I | H | A | DELETED |
| S | S | S | I | T | Y | I | H | A | E |
| S | S | S | I | T | Y | I | H | V | DELETED |
| S | S | S | I | T | Y | I | H | V | E |
| S | S | S | I | T | Y | V | Q | A | DELETED |
| S | S | S | I | T | Y | V | Q | A | E |
| S | S | S | I | T | Y | V | Q | V | DELETED |
| S | S | S | I | T | Y | V | Q | V | E |
| S | S | S | I | T | Y | V | H | A | DELETED |
| S | S | S | I | T | Y | V | H | A | E |
| S | S | S | I | T | Y | V | H | V | DELETED |
| S | S | S | I | T | Y | V | H | V | E |
| S | S | S | I | T | S | I | Q | A | DELETED |
| S | S | S | I | T | S | I | Q | A | E |
| S | S | S | I | T | S | I | Q | V | DELETED |
| S | S | S | I | T | S | I | Q | V | E |
| S | S | S | I | T | S | I | H | A | DELETED |
| S | S | S | I | T | S | I | H | A | E |
| S | S | S | I | T | S | I | H | V | DELETED |
| S | S | S | I | T | S | I | H | V | E |
| S | S | S | I | T | S | V | Q | A | DELETED |
| S | S | S | I | T | S | V | Q | A | E |
| S | S | S | I | T | S | V | Q | V | DELETED |
| S | S | S | I | T | S | V | Q | V | E |
| S | S | S | I | T | S | V | H | A | DELETED |
| S | S | S | I | T | S | V | H | A | E |
| S | S | S | I | T | S | V | H | V | DELETED |
| S | S | S | I | T | S | V | H | V | E |
| S | S | N | V | S | Y | I | Q | A | DELETED |
| S | S | N | V | S | Y | I | Q | A | E |
| S | S | N | V | S | Y | I | Q | V | DELETED |
| S | S | N | V | S | Y | I | Q | V | E |
| S | S | N | V | S | Y | I | H | A | DELETED |
| S | S | N | V | S | Y | I | H | A | E |
| S | S | N | V | S | Y | I | H | V | DELETED |
| S | S | N | V | S | Y | I | H | V | E |
| S | S | N | V | S | Y | V | Q | A | DELETED |
| S | S | N | V | S | Y | V | Q | A | E |
| S | S | N | V | S | Y | V | Q | V | DELETED |
| S | S | N | V | S | Y | V | Q | V | E |
| S | S | N | V | S | Y | V | H | A | DELETED |
| S | S | N | V | S | Y | V | H | A | E |
| S | S | N | V | S | Y | V | H | V | DELETED |
| S | S | N | V | S | Y | V | H | V | E |
| S | S | N | V | S | S | I | Q | A | DELETED |
| S | S | N | V | S | S | I | Q | A | E |
| S | S | N | V | S | S | I | Q | V | DELETED |
| S | S | N | V | S | S | I | Q | V | E |
| S | S | N | V | S | S | I | H | A | DELETED |
| S | S | N | V | S | S | I | H | A | E |
| S | S | N | V | S | S | I | H | V | DELETED |
| S | S | N | V | S | S | I | H | V | E |
| S | S | N | V | S | S | V | Q | A | DELETED |
| S | S | N | V | S | S | V | Q | A | E |
| S | S | N | V | S | S | V | Q | V | DELETED |
| S | S | N | V | S | S | V | Q | V | E |
| S | S | N | V | S | S | V | H | A | DELETED |
| S | S | N | V | S | S | V | H | A | E |
| S | S | N | V | S | S | V | H | V | DELETED |
| S | S | N | V | S | S | V | H | V | E |
| S | S | N | V | T | Y | I | Q | A | DELETED |
| S | S | N | V | T | Y | I | Q | A | E |
| S | S | N | V | T | Y | I | Q | V | DELETED |
| S | S | N | V | T | Y | I | Q | V | E |
| S | S | N | V | T | Y | I | H | A | DELETED |
| S | S | N | V | T | Y | I | H | A | E |
| S | S | N | V | T | Y | I | H | V | DELETED |
| S | S | N | V | T | Y | V | Q | A | DELETED |
| S | S | N | V | T | Y | V | Q | A | E |
| S | S | N | V | T | Y | V | Q | V | DELETED |
| S | S | N | V | T | Y | V | Q | V | E |
| S | S | N | V | T | Y | V | H | A | DELETED |
| S | S | N | V | T | Y | V | H | A | E |
| S | S | N | V | T | Y | V | H | V | DELETED |
| S | S | N | V | T | Y | V | H | V | E |
| S | S | N | V | T | S | I | Q | A | DELETED |
| S | S | N | V | T | S | I | Q | A | E |
| S | S | N | V | T | S | I | Q | V | DELETED |
| S | S | N | V | T | S | I | Q | V | E |
| S | S | N | V | T | S | I | H | A | DELETED |
| S | S | N | V | T | S | I | H | A | E |
| S | S | N | V | T | S | I | H | V | DELETED |
| S | S | N | V | T | S | I | H | V | E |
| S | S | N | V | T | S | V | Q | A | DELETED |
| S | S | N | V | T | S | V | Q | A | E |
| S | S | N | V | T | S | V | Q | V | DELETED |
| S | S | N | V | T | S | V | Q | V | E |
| S | S | N | V | T | S | V | H | A | DELETED |
| S | S | N | V | T | S | V | H | A | E |
| S | S | N | V | T | S | V | H | V | DELETED |
| S | S | N | V | T | S | V | H | V | E |
| S | S | N | I | S | Y | I | Q | A | DELETED |
| S | S | N | I | S | Y | I | Q | A | E |
| S | S | N | I | S | Y | I | Q | V | DELETED |
| S | S | N | I | S | Y | I | Q | V | E |
| S | S | N | I | S | Y | I | H | A | DELETED |
| S | S | N | I | S | Y | I | H | A | E |
| S | S | N | I | S | Y | I | H | V | DELETED |
| S | S | N | I | S | Y | I | H | V | E |
| S | S | N | I | S | Y | V | Q | A | DELETED |
| S | S | N | I | S | Y | V | Q | A | E |
| S | S | N | I | S | Y | V | Q | V | DELETED |
| S | S | N | I | S | Y | V | Q | V | E |
| S | S | N | I | S | Y | V | H | A | DELETED |
| S | S | N | I | S | Y | V | H | A | E |
| S | S | N | I | S | Y | V | H | V | DELETED |
| S | S | N | I | S | Y | V | H | V | E |
| S | S | N | I | S | S | I | Q | A | DELETED |
| S | S | N | I | S | S | I | Q | A | E |
| S | S | N | I | S | S | I | Q | V | DELETED |
| S | S | N | I | S | S | I | Q | V | E |
| S | S | N | I | S | S | I | H | A | DELETED |
| S | S | N | I | S | S | I | H | A | E |
| S | S | N | I | S | S | I | H | V | DELETED |
| S | S | N | I | S | S | I | H | V | E |
| S | S | N | I | S | S | V | Q | A | DELETED |
| S | S | N | I | S | S | V | Q | A | E |
| S | S | N | I | S | S | V | Q | V | DELETED |
| S | S | N | I | S | S | V | Q | V | E |
| S | S | N | I | S | S | V | H | A | DELETED |
| S | S | N | I | S | S | V | H | A | E |
| S | S | N | I | S | S | V | H | V | DELETED |
| S | S | N | I | T | Y | I | Q | A | DELETED |
| S | S | N | I | T | Y | I | Q | V | DELETED |
| S | S | N | I | T | Y | I | Q | V | E |
| S | S | N | I | T | Y | I | H | A | DELETED |
| S | S | N | I | T | Y | I | H | A | E |
| S | S | N | I | T | Y | I | H | V | DELETED |

TABLE 15-continued

Exemplary Mutations of mAb 2.6.1 Heavy Chain (SEQ ID NO: 26) to Germline at the Indicated Residue Number.

| 30 | 31 | 35 | 50 | 53 | 58 | 69 | 81 | 87 | 98 |
|---|---|---|---|---|---|---|---|---|---|
| S | S | N | I | T | Y | I | H | V | E |
| S | S | N | I | T | Y | V | Q | A | DELETED |
| S | S | N | I | T | Y | V | Q | A | E |
| S | S | N | I | T | Y | V | Q | V | DELETED |
| S | S | N | I | T | Y | V | Q | V | E |
| S | S | N | I | T | Y | V | H | A | DELETED |
| S | S | N | I | T | Y | V | H | A | E |
| S | S | N | I | T | Y | V | H | V | DELETED |
| S | S | N | I | T | Y | V | H | V | E |
| S | S | N | I | T | S | I | Q | A | DELETED |
| S | S | N | I | T | S | I | Q | A | E |
| S | S | N | I | T | S | I | Q | V | DELETED |
| S | S | N | I | T | S | I | Q | V | E |
| S | S | N | I | T | S | I | H | A | DELETED |
| S | S | N | I | T | S | I | H | A | E |
| S | S | N | I | T | S | I | H | V | DELETED |
| S | S | N | I | T | S | I | H | V | E |
| S | S | N | I | T | S | V | Q | A | DELETED |
| S | S | N | I | T | S | V | Q | A | E |
| S | S | N | I | T | S | V | Q | V | DELETED |
| S | S | N | I | T | S | V | Q | V | E |
| S | S | N | I | T | S | V | H | A | DELETED |
| S | S | N | I | T | S | V | H | A | E |
| S | S | N | I | T | S | V | H | V | DELETED |
| S | S | N | I | T | S | V | H | V | E |
| S | T | S | V | S | Y | I | Q | A | DELETED |
| S | T | S | V | S | Y | I | Q | A | E |
| S | T | S | V | S | Y | I | Q | V | DELETED |
| S | T | S | V | S | Y | I | Q | V | E |
| S | T | S | V | S | Y | I | H | A | DELETED |
| S | T | S | V | S | Y | I | H | A | E |
| S | T | S | V | S | Y | I | H | V | DELETED |
| S | T | S | V | S | Y | V | Q | A | DELETED |
| S | T | S | V | S | Y | V | Q | A | E |
| S | T | S | V | S | Y | V | Q | V | DELETED |
| S | T | S | V | S | Y | V | Q | V | E |
| S | T | S | V | S | Y | V | H | A | DELETED |
| S | T | S | V | S | Y | V | H | A | E |
| S | T | S | V | S | Y | V | H | V | DELETED |
| S | T | S | V | S | Y | V | H | V | E |
| S | T | S | V | S | S | I | Q | A | DELETED |
| S | T | S | V | S | S | I | Q | A | E |
| S | T | S | V | S | S | I | Q | V | DELETED |
| S | T | S | V | S | S | I | Q | V | E |
| S | T | S | V | S | S | I | H | A | DELETED |
| S | T | S | V | S | S | I | H | A | E |
| S | T | S | V | S | S | I | H | V | DELETED |
| S | T | S | V | S | S | I | H | V | E |
| S | T | S | V | S | S | V | Q | A | DELETED |
| S | T | S | V | S | S | V | Q | A | E |
| S | T | S | V | S | S | V | Q | V | DELETED |
| S | T | S | V | S | S | V | Q | V | E |
| S | T | S | V | S | S | V | H | A | DELETED |
| S | T | S | V | S | S | V | H | A | E |
| S | T | S | V | S | S | V | H | V | DELETED |
| S | T | S | V | S | S | V | H | V | E |
| S | T | S | V | T | Y | I | Q | A | DELETED |
| S | T | S | V | T | Y | I | Q | A | E |
| S | T | S | V | T | Y | I | Q | V | DELETED |
| S | T | S | V | T | Y | I | Q | V | E |
| S | T | S | V | T | Y | I | H | A | DELETED |
| S | T | S | V | T | Y | I | H | A | E |
| S | T | S | V | T | Y | I | H | V | DELETED |
| S | T | S | V | T | Y | I | H | V | E |
| S | T | S | V | T | Y | V | Q | A | DELETED |
| S | T | S | V | T | Y | V | Q | V | DELETED |
| S | T | S | V | T | Y | V | Q | V | E |
| S | T | S | V | T | Y | V | H | A | DELETED |
| S | T | S | V | T | Y | V | H | A | E |
| S | T | S | V | T | Y | V | H | V | DELETED |
| S | T | S | V | T | Y | V | H | V | E |
| S | T | S | V | T | S | I | Q | A | DELETED |
| S | T | S | V | T | S | I | Q | A | E |
| S | T | S | V | T | S | I | Q | V | DELETED |
| S | T | S | V | T | S | I | Q | V | E |
| S | T | S | V | T | S | I | H | A | DELETED |
| S | T | S | V | T | S | I | H | A | E |
| S | T | S | V | T | S | I | H | V | DELETED |
| S | T | S | V | T | S | I | H | V | E |
| S | T | S | V | T | S | V | Q | A | DELETED |
| S | T | S | V | T | S | V | Q | A | E |
| S | T | S | V | T | S | V | Q | V | DELETED |
| S | T | S | V | T | S | V | Q | V | E |
| S | T | S | V | T | S | V | H | A | DELETED |
| S | T | S | I | S | Y | I | Q | A | DELETED |
| S | T | S | I | S | Y | I | Q | A | E |
| S | T | S | I | S | Y | I | Q | V | DELETED |
| S | T | S | I | S | Y | I | Q | V | E |
| S | T | S | I | S | Y | I | H | A | DELETED |
| S | T | S | I | S | Y | I | H | A | E |
| S | T | S | I | S | Y | I | H | V | DELETED |
| S | T | S | I | S | Y | I | H | V | E |
| S | T | S | I | S | Y | V | Q | A | DELETED |
| S | T | S | I | S | Y | V | Q | A | E |
| S | T | S | I | S | Y | V | Q | V | DELETED |
| S | T | S | I | S | Y | V | Q | V | E |
| S | T | S | I | S | Y | V | H | A | DELETED |
| S | T | S | I | S | Y | V | H | A | E |
| S | T | S | I | S | Y | V | H | V | DELETED |
| S | T | S | I | S | Y | V | H | V | E |
| S | T | S | I | S | S | I | Q | A | DELETED |
| S | T | S | I | S | S | I | Q | A | E |
| S | T | S | I | S | S | I | Q | V | DELETED |
| S | T | S | I | S | S | I | Q | V | E |
| S | T | S | I | S | S | I | H | A | DELETED |
| S | T | S | I | S | S | I | H | A | E |
| S | T | S | I | S | S | I | H | V | DELETED |
| S | T | S | I | S | S | I | H | V | E |
| S | T | S | I | S | S | V | Q | A | DELETED |
| S | T | S | I | S | S | V | Q | A | E |
| S | T | S | I | S | S | V | Q | V | DELETED |
| S | T | S | I | S | S | V | Q | V | E |
| S | T | S | I | S | S | V | H | A | DELETED |
| S | T | S | I | S | S | V | H | A | E |
| S | T | S | I | S | S | V | H | V | DELETED |
| S | T | S | I | S | S | V | H | V | E |
| S | T | S | I | T | Y | I | Q | A | DELETED |
| S | T | S | I | T | Y | I | Q | A | E |
| S | T | S | I | T | Y | I | Q | V | DELETED |
| S | T | S | I | T | Y | I | Q | V | E |
| S | T | S | I | T | Y | I | H | A | DELETED |
| S | T | S | I | T | Y | I | H | A | E |
| S | T | S | I | T | Y | I | H | V | DELETED |
| S | T | S | I | T | Y | I | H | V | E |
| S | T | S | I | T | Y | V | Q | A | DELETED |
| S | T | S | I | T | Y | V | Q | A | E |
| S | T | S | I | T | Y | V | Q | V | DELETED |
| S | T | S | I | T | Y | V | Q | V | E |
| S | T | S | I | T | Y | V | H | A | DELETED |
| S | T | S | I | T | Y | V | H | A | E |
| S | T | S | I | T | Y | V | H | V | DELETED |
| S | T | S | I | T | Y | V | H | V | E |
| S | T | S | I | T | S | I | Q | A | DELETED |
| S | T | S | I | T | S | I | Q | A | E |
| S | T | S | I | T | S | I | Q | V | DELETED |
| S | T | S | I | T | S | I | Q | V | E |
| S | T | S | I | T | S | I | H | A | DELETED |
| S | T | S | I | T | S | I | H | A | E |
| S | T | S | I | T | S | I | H | V | DELETED |
| S | T | S | I | T | S | V | Q | A | E |
| S | T | S | I | T | S | V | Q | V | DELETED |
| S | T | S | I | T | S | V | Q | V | E |
| S | T | S | I | T | S | V | H | A | DELETED |

TABLE 15-continued

Exemplary Mutations of mAb 2.6.1 Heavy Chain (SEQ ID NO: 26) to Germline at the Indicated Residue Number.

| 30 | 31 | 35 | 50 | 53 | 58 | 69 | 81 | 87 | 98 |
|---|---|---|---|---|---|---|---|---|---|
| S | T | S | I | T | S | V | H | A | E |
| S | T | S | I | T | S | V | H | V | DELETED |
| S | T | S | I | T | S | V | H | V | E |
| S | T | N | V | S | Y | I | Q | A | DELETED |
| S | T | N | V | S | Y | I | Q | A | E |
| S | T | N | V | S | Y | I | Q | V | DELETED |
| S | T | N | V | S | Y | I | Q | V | E |
| S | T | N | V | S | Y | I | H | A | DELETED |
| S | T | N | V | S | Y | I | H | A | E |
| S | T | N | V | S | Y | I | H | V | DELETED |
| S | T | N | V | S | Y | I | H | V | E |
| S | T | N | V | S | Y | V | Q | A | DELETED |
| S | T | N | V | S | Y | V | Q | A | E |
| S | T | N | V | S | Y | V | Q | V | DELETED |
| S | T | N | V | S | Y | V | Q | V | E |
| S | T | N | V | S | Y | V | H | A | DELETED |
| S | T | N | V | S | Y | V | H | A | E |
| S | T | N | V | S | Y | V | H | V | DELETED |
| S | T | N | V | S | Y | V | H | V | E |
| S | T | N | V | S | S | I | Q | A | DELETED |
| S | T | N | V | S | S | I | Q | A | E |
| S | T | N | V | S | S | I | Q | V | DELETED |
| S | T | N | V | S | S | I | Q | V | E |
| S | T | N | V | S | S | I | H | A | DELETED |
| S | T | N | V | S | S | I | H | A | E |
| S | T | N | V | S | S | I | H | V | DELETED |
| S | T | N | V | S | S | I | H | V | E |
| S | T | N | V | S | S | V | Q | A | DELETED |
| S | T | N | V | S | S | V | Q | A | E |
| S | T | N | V | S | S | V | Q | V | DELETED |
| S | T | N | V | S | S | V | Q | V | E |
| S | T | N | V | S | S | V | H | A | DELETED |
| S | T | N | V | S | S | V | H | A | E |
| S | T | N | V | S | S | V | H | V | DELETED |
| S | T | N | V | T | Y | I | Q | A | DELETED |
| S | T | N | V | T | Y | I | Q | A | E |
| S | T | N | V | T | Y | I | Q | V | DELETED |
| S | T | N | V | T | Y | I | Q | V | E |
| S | T | N | V | T | Y | I | H | A | DELETED |
| S | T | N | V | T | Y | I | H | A | E |
| S | T | N | V | T | Y | I | H | V | DELETED |
| S | T | N | V | T | Y | I | H | V | E |
| S | T | N | V | T | Y | V | Q | A | DELETED |
| S | T | N | V | T | Y | V | Q | A | E |
| S | T | N | V | T | Y | V | Q | V | DELETED |
| S | T | N | V | T | Y | V | Q | V | E |
| S | T | N | V | T | Y | V | H | A | DELETED |
| S | T | N | V | T | Y | V | H | A | E |
| S | T | N | V | T | Y | V | H | V | DELETED |
| S | T | N | V | T | Y | V | H | V | E |
| S | T | N | V | T | S | I | Q | A | DELETED |
| S | T | N | V | T | S | I | Q | A | E |
| S | T | N | V | T | S | I | Q | V | DELETED |
| S | T | N | V | T | S | I | Q | V | E |
| S | T | N | V | T | S | I | H | A | DELETED |
| S | T | N | V | T | S | I | H | A | E |
| S | T | N | V | T | S | I | H | V | DELETED |
| S | T | N | V | T | S | I | H | V | E |
| S | T | N | V | T | S | V | Q | A | DELETED |
| S | T | N | V | T | S | V | Q | A | E |
| S | T | N | V | T | S | V | Q | V | DELETED |
| S | T | N | V | T | S | V | Q | V | E |
| S | T | N | V | T | S | V | H | A | DELETED |
| S | T | N | V | T | S | V | H | A | E |
| S | T | N | V | T | S | V | H | V | DELETED |
| S | T | N | V | T | S | V | H | V | E |
| S | T | N | I | S | Y | I | Q | A | DELETED |
| S | T | N | I | S | Y | I | Q | A | E |
| S | T | N | I | S | Y | I | Q | V | DELETED |
| S | T | N | I | S | Y | I | Q | V | E |
| S | T | N | I | S | Y | I | H | A | DELETED |
| S | T | N | I | S | Y | I | H | A | E |
| S | T | N | I | S | Y | I | H | V | DELETED |
| S | T | N | I | S | Y | I | H | V | E |
| S | T | N | I | S | Y | V | Q | A | DELETED |
| S | T | N | I | S | Y | V | Q | A | E |
| S | T | N | I | S | Y | V | Q | V | DELETED |
| S | T | N | I | S | Y | V | Q | V | E |
| S | T | N | I | S | Y | V | H | A | DELETED |
| S | T | N | I | S | Y | V | H | A | E |
| S | T | N | I | S | Y | V | H | V | DELETED |
| S | T | N | I | S | Y | V | H | V | E |
| S | T | N | I | S | S | I | Q | A | DELETED |
| S | T | N | I | S | S | I | Q | A | E |
| S | T | N | I | S | S | I | Q | V | DELETED |
| S | T | N | I | S | S | I | Q | V | E |
| S | T | N | I | S | S | I | H | A | DELETED |
| S | T | N | I | S | S | I | H | A | E |
| S | T | N | I | S | S | I | H | V | DELETED |
| S | T | N | I | S | S | I | H | V | E |
| S | T | N | I | S | S | V | Q | A | DELETED |
| S | T | N | I | S | S | V | Q | A | E |
| S | T | N | I | S | S | V | Q | V | DELETED |
| S | T | N | I | S | S | V | Q | V | E |
| S | T | N | I | S | S | V | H | A | DELETED |
| S | T | N | I | S | S | V | H | A | E |
| S | T | N | I | S | S | V | H | V | DELETED |
| S | T | N | I | S | S | V | H | V | E |
| S | T | N | I | T | Y | I | Q | A | DELETED |
| S | T | N | I | T | Y | I | Q | A | E |
| S | T | N | I | T | Y | I | Q | V | DELETED |
| S | T | N | I | T | Y | I | Q | V | E |
| S | T | N | I | T | Y | I | H | A | DELETED |
| S | T | N | I | T | Y | I | H | A | E |
| S | T | N | I | T | Y | I | H | V | DELETED |
| S | T | N | I | T | Y | I | H | V | E |
| S | T | N | I | T | Y | V | Q | A | DELETED |
| S | T | N | I | T | Y | V | Q | A | E |
| S | T | N | I | T | Y | V | Q | V | DELETED |
| S | T | N | I | T | Y | V | Q | V | E |
| S | T | N | I | T | Y | V | H | A | DELETED |
| S | T | N | I | T | Y | V | H | A | E |
| S | T | N | I | T | Y | V | H | V | DELETED |
| S | T | N | I | T | Y | V | H | V | E |
| S | T | N | I | T | S | I | Q | A | DELETED |
| S | T | N | I | T | S | I | Q | A | E |
| S | T | N | I | T | S | I | Q | V | DELETED |
| S | T | N | I | T | S | I | Q | V | E |
| S | T | N | I | T | S | I | H | A | DELETED |
| S | T | N | I | T | S | I | H | A | E |
| S | T | N | I | T | S | I | H | V | DELETED |
| S | T | N | I | T | S | I | H | V | E |
| S | T | N | I | T | S | V | Q | A | DELETED |
| S | T | N | I | T | S | V | Q | A | E |
| S | T | N | I | T | S | V | Q | V | DELETED |
| S | T | N | I | T | S | V | Q | V | E |
| S | T | N | I | T | S | V | H | A | DELETED |
| S | T | N | I | T | S | V | H | A | E |
| S | T | N | I | T | S | V | H | V | DELETED |
| S | T | N | I | T | S | V | H | V | E |
| I | S | S | V | S | Y | I | Q | A | DELETED |
| I | S | S | V | S | Y | I | Q | A | E |
| I | S | S | V | S | Y | I | Q | V | DELETED |
| I | S | S | V | S | Y | I | Q | V | E |
| I | S | S | V | S | Y | I | H | A | DELETED |
| I | S | S | V | S | Y | I | H | A | E |
| I | S | S | V | S | Y | I | H | V | DELETED |
| I | S | S | V | S | Y | I | H | V | E |
| I | S | S | V | S | Y | V | Q | A | DELETED |
| I | S | S | V | S | Y | V | Q | A | E |
| I | S | S | V | S | Y | V | Q | V | DELETED |
| I | S | S | V | S | Y | V | Q | V | E |
| I | S | S | V | S | Y | V | H | A | DELETED |
| I | S | S | V | S | Y | V | H | A | E |
| I | S | S | V | S | Y | V | H | V | DELETED |
| I | S | S | V | S | Y | V | H | V | E |
| I | S | S | V | S | S | I | Q | A | DELETED |
| I | S | S | V | S | S | I | Q | A | E |
| I | S | S | V | S | S | I | Q | V | DELETED |

TABLE 15-continued

Exemplary Mutations of mAb 2.6.1 Heavy Chain (SEQ ID NO: 26) to Germline at the Indicated Residue Number.

| 30 | 31 | 35 | 50 | 53 | 58 | 69 | 81 | 87 | 98 |
|---|---|---|---|---|---|---|---|---|---|
| I | S | S | V | S | S | I | Q | V | E |
| I | S | S | V | S | S | I | H | A | DELETED |
| I | S | S | V | S | S | I | H | A | E |
| I | S | S | V | S | S | I | H | V | DELETED |
| I | S | S | V | S | S | I | H | V | E |
| I | S | S | V | S | S | V | Q | A | DELETED |
| I | S | S | V | S | S | V | Q | A | E |
| I | S | S | V | S | S | V | Q | V | DELETED |
| I | S | S | V | S | S | V | Q | V | E |
| I | S | S | V | S | S | V | H | A | DELETED |
| I | S | S | V | S | S | V | H | A | E |
| I | S | S | V | S | S | V | H | V | DELETED |
| I | S | S | V | S | S | V | H | V | E |
| I | S | S | V | T | Y | I | Q | A | DELETED |
| I | S | S | V | T | Y | I | Q | A | E |
| I | S | S | V | T | Y | I | Q | V | DELETED |
| I | S | S | V | T | Y | I | Q | V | E |
| I | S | S | V | T | Y | I | H | A | DELETED |
| I | S | S | V | T | Y | I | H | A | E |
| I | S | S | V | T | Y | I | H | V | DELETED |
| I | S | S | V | T | Y | I | H | V | E |
| I | S | S | V | T | Y | V | Q | A | DELETED |
| I | S | S | V | T | Y | V | Q | A | E |
| I | S | S | V | T | Y | V | Q | V | DELETED |
| I | S | S | V | T | Y | V | Q | V | E |
| I | S | S | V | T | Y | V | H | A | DELETED |
| I | S | S | V | T | Y | V | H | A | E |
| I | S | S | V | T | Y | V | H | V | DELETED |
| I | S | S | V | T | Y | V | H | V | E |
| I | S | S | V | T | S | I | Q | A | DELETED |
| I | S | S | V | T | S | I | Q | A | E |
| I | S | S | V | T | S | I | Q | V | DELETED |
| I | S | S | V | T | S | I | Q | V | E |
| I | S | S | V | T | S | I | H | A | DELETED |
| I | S | S | V | T | S | I | H | A | E |
| I | S | S | V | T | S | I | H | V | DELETED |
| I | S | S | V | T | S | I | H | V | E |
| I | S | S | V | T | S | V | Q | A | DELETED |
| I | S | S | V | T | S | V | Q | A | E |
| I | S | S | V | T | S | V | Q | V | DELETED |
| I | S | S | V | T | S | V | Q | V | E |
| I | S | S | V | T | S | V | H | A | DELETED |
| I | S | S | V | T | S | V | H | A | E |
| I | S | S | V | T | S | V | H | V | DELETED |
| I | S | S | V | T | S | V | H | V | E |
| I | S | S | I | S | Y | I | Q | A | DELETED |
| I | S | S | I | S | Y | I | Q | A | E |
| I | S | S | I | S | Y | I | Q | V | DELETED |
| I | S | S | I | S | Y | I | Q | V | E |
| I | S | S | I | S | Y | I | H | A | DELETED |
| I | S | S | I | S | Y | I | H | A | E |
| I | S | S | I | S | Y | I | H | V | DELETED |
| I | S | S | I | S | Y | I | H | V | E |
| I | S | S | I | S | Y | V | Q | A | DELETED |
| I | S | S | I | S | Y | V | Q | A | E |
| I | S | S | I | S | Y | V | Q | V | DELETED |
| I | S | S | I | S | Y | V | Q | V | E |
| I | S | S | I | S | Y | V | H | A | DELETED |
| I | S | S | I | S | Y | V | H | A | E |
| I | S | S | I | S | Y | V | H | V | DELETED |
| I | S | S | I | S | Y | V | H | V | E |
| I | S | S | I | S | S | I | Q | A | DELETED |
| I | S | S | I | S | S | I | Q | A | E |
| I | S | S | I | S | S | I | Q | V | DELETED |
| I | S | S | I | S | S | I | Q | V | E |
| I | S | S | I | S | S | I | H | A | DELETED |
| I | S | S | I | S | S | I | H | A | E |
| I | S | S | I | S | S | I | H | V | DELETED |
| I | S | S | I | S | S | I | H | V | E |
| I | S | S | I | S | S | V | Q | A | DELETED |
| I | S | S | I | S | S | V | Q | A | E |
| I | S | S | I | S | S | V | Q | V | DELETED |
| I | S | S | I | S | S | V | Q | V | E |
| I | S | S | I | S | S | V | H | A | DELETED |
| I | S | S | I | S | S | V | H | A | E |
| I | S | S | I | S | S | V | H | V | DELETED |
| I | S | S | I | S | S | V | H | V | E |
| I | S | S | I | T | Y | I | Q | A | DELETED |
| I | S | S | I | T | Y | I | Q | A | E |
| I | S | S | I | T | Y | I | Q | V | DELETED |
| I | S | S | I | T | Y | I | Q | V | E |
| I | S | S | I | T | Y | I | H | A | DELETED |
| I | S | S | I | T | Y | I | H | A | E |
| I | S | S | I | T | Y | I | H | V | DELETED |
| I | S | S | I | T | Y | I | H | V | E |
| I | S | S | I | T | Y | V | Q | A | DELETED |
| I | S | S | I | T | Y | V | Q | A | E |
| I | S | S | I | T | Y | V | Q | V | DELETED |
| I | S | S | I | T | Y | V | Q | V | E |
| I | S | S | I | T | Y | V | H | A | DELETED |
| I | S | S | I | T | Y | V | H | A | E |
| I | S | S | I | T | Y | V | H | V | DELETED |
| I | S | S | I | T | Y | V | H | V | E |
| I | S | S | I | T | S | I | Q | A | DELETED |
| I | S | S | I | T | S | I | Q | A | E |
| I | S | S | I | T | S | I | Q | V | DELETED |
| I | S | S | I | T | S | I | Q | V | E |
| I | S | S | I | T | S | I | H | A | DELETED |
| I | S | S | I | T | S | I | H | A | E |
| I | S | S | I | T | S | I | H | V | DELETED |
| I | S | S | I | T | S | I | H | V | E |
| I | S | S | I | T | S | V | Q | A | DELETED |
| I | S | S | I | T | S | V | Q | A | E |
| I | S | S | I | T | S | V | Q | V | DELETED |
| I | S | S | I | T | S | V | Q | V | E |
| I | S | S | I | T | S | V | H | A | DELETED |
| I | S | S | I | T | S | V | H | A | E |
| I | S | S | I | T | S | V | H | V | DELETED |
| I | S | S | I | T | S | V | H | V | E |
| I | S | N | V | S | Y | I | Q | A | DELETED |
| I | S | N | V | S | Y | I | Q | A | E |
| I | S | N | V | S | Y | I | Q | V | DELETED |
| I | S | N | V | S | Y | I | Q | V | E |
| I | S | N | V | S | Y | I | H | A | DELETED |
| I | S | N | V | S | Y | I | H | A | E |
| I | S | N | V | S | Y | I | H | V | DELETED |
| I | S | N | V | S | Y | I | H | V | E |
| I | S | N | V | S | Y | V | Q | A | DELETED |
| I | S | N | V | S | Y | V | Q | A | E |
| I | S | N | V | S | Y | V | Q | V | DELETED |
| I | S | N | V | S | Y | V | Q | V | E |
| I | S | N | V | S | Y | V | H | A | DELETED |
| I | S | N | V | S | Y | V | H | A | E |
| I | S | N | V | S | Y | V | H | V | DELETED |
| I | S | N | V | S | Y | V | H | V | E |
| I | S | N | V | S | S | I | Q | A | DELETED |
| I | S | N | V | S | S | I | Q | A | E |
| I | S | N | V | S | S | I | Q | V | DELETED |
| I | S | N | V | S | S | I | Q | V | E |
| I | S | N | V | S | S | I | H | A | DELETED |
| I | S | N | V | S | S | I | H | A | E |
| I | S | N | V | S | S | I | H | V | DELETED |
| I | S | N | V | S | S | I | H | V | E |
| I | S | N | V | S | S | V | Q | A | DELETED |
| I | S | N | V | S | S | V | Q | A | E |
| I | S | N | V | S | S | V | Q | V | DELETED |
| I | S | N | V | S | S | V | Q | V | E |
| I | S | N | V | S | S | V | H | A | DELETED |
| I | S | N | V | S | S | V | H | A | E |
| I | S | N | V | S | S | V | H | V | DELETED |
| I | S | N | V | S | S | V | H | V | E |
| I | S | N | V | T | Y | I | Q | A | DELETED |
| I | S | N | V | T | Y | I | Q | A | E |
| I | S | N | V | T | Y | I | Q | V | DELETED |
| I | S | N | V | T | Y | I | Q | V | E |
| I | S | N | V | T | Y | I | H | A | DELETED |
| I | S | N | V | T | Y | I | H | A | E |
| I | S | N | V | T | Y | I | H | V | DELETED |
| I | S | N | V | T | Y | I | H | V | E |
| I | S | N | V | T | Y | V | Q | A | DELETED |

TABLE 15-continued

Exemplary Mutations of mAb 2.6.1 Heavy Chain (SEQ ID NO: 26) to Germline at the Indicated Residue Number.

| 30 | 31 | 35 | 50 | 53 | 58 | 69 | 81 | 87 | 98 |
|---|---|---|---|---|---|---|---|---|---|
| I | S | N | V | T | Y | V | Q | A | E |
| I | S | N | V | T | Y | V | Q | V | DELETED |
| I | S | N | V | T | Y | V | Q | V | E |
| I | S | N | V | T | Y | V | H | A | DELETED |
| I | S | N | V | T | Y | V | H | A | E |
| I | S | N | V | T | Y | V | H | V | DELETED |
| I | S | N | V | T | Y | V | H | V | E |
| I | S | N | V | T | S | I | Q | A | DELETED |
| I | S | N | V | T | S | I | Q | A | E |
| I | S | N | V | T | S | I | Q | V | DELETED |
| I | S | N | V | T | S | I | Q | V | E |
| I | S | N | V | T | S | I | H | A | DELETED |
| I | S | N | V | T | S | I | H | A | E |
| I | S | N | V | T | S | I | H | V | DELETED |
| I | S | N | V | T | S | I | H | V | E |
| I | S | N | V | T | S | V | Q | A | DELETED |
| I | S | N | V | T | S | V | Q | A | E |
| I | S | N | V | T | S | V | Q | V | DELETED |
| I | S | N | V | T | S | V | Q | V | E |
| I | S | N | V | T | S | V | H | A | DELETED |
| I | S | N | V | T | S | V | H | A | E |
| I | S | N | V | T | S | V | H | V | DELETED |
| I | S | N | V | T | S | V | H | V | E |
| I | S | N | I | S | Y | I | Q | A | DELETED |
| I | S | N | I | S | Y | I | Q | A | E |
| I | S | N | I | S | Y | I | Q | V | DELETED |
| I | S | N | I | S | Y | I | Q | V | E |
| I | S | N | I | S | Y | I | H | A | DELETED |
| I | S | N | I | S | Y | I | H | A | E |
| I | S | N | I | S | Y | I | H | V | DELETED |
| I | S | N | I | S | Y | I | H | V | E |
| I | S | N | I | S | Y | V | Q | A | DELETED |
| I | S | N | I | S | Y | V | Q | A | E |
| I | S | N | I | S | Y | V | Q | V | DELETED |
| I | S | N | I | S | Y | V | Q | V | E |
| I | S | N | I | S | Y | V | H | A | DELETED |
| I | S | N | I | S | Y | V | H | A | E |
| I | S | N | I | S | Y | V | H | V | DELETED |
| I | S | N | I | S | Y | V | H | V | E |
| I | S | N | I | S | S | I | Q | A | DELETED |
| I | S | N | I | S | S | I | Q | A | E |
| I | S | N | I | S | S | I | Q | V | DELETED |
| I | S | N | I | S | S | I | Q | V | E |
| I | S | N | I | S | S | I | H | A | DELETED |
| I | S | N | I | S | S | I | H | A | E |
| I | S | N | I | S | S | I | H | V | DELETED |
| I | S | N | I | S | S | I | H | V | E |
| I | S | N | I | S | S | V | Q | A | DELETED |
| I | S | N | I | S | S | V | Q | A | E |
| I | S | N | I | S | S | V | Q | V | DELETED |
| I | S | N | I | S | S | V | Q | V | E |
| I | S | N | I | S | S | V | H | A | DELETED |
| I | S | N | I | S | S | V | H | A | E |
| I | S | N | I | S | S | V | H | V | DELETED |
| I | S | N | I | S | S | V | H | V | E |
| I | S | N | I | T | Y | I | Q | A | DELETED |
| I | S | N | I | T | Y | I | Q | A | E |
| I | S | N | I | T | Y | I | Q | V | DELETED |
| I | S | N | I | T | Y | I | Q | V | E |
| I | S | N | I | T | Y | I | H | A | DELETED |
| I | S | N | I | T | Y | I | H | A | E |
| I | S | N | I | T | Y | I | H | V | DELETED |
| I | S | N | I | T | Y | I | H | V | E |
| I | S | N | I | T | Y | V | Q | A | DELETED |
| I | S | N | I | T | Y | V | Q | A | E |
| I | S | N | I | T | Y | V | Q | V | DELETED |
| I | S | N | I | T | Y | V | Q | V | E |
| I | S | N | I | T | Y | V | H | A | DELETED |
| I | S | N | I | T | Y | V | H | A | E |
| I | S | N | I | T | Y | V | H | V | DELETED |
| I | S | N | I | T | Y | V | H | V | E |
| I | S | N | I | T | S | I | Q | A | DELETED |
| I | S | N | I | T | S | I | Q | A | E |
| I | S | N | I | T | S | I | Q | V | DELETED |
| I | S | N | I | T | S | I | Q | V | E |
| I | S | N | I | T | S | I | H | A | DELETED |
| I | S | N | I | T | S | I | H | A | E |
| I | S | N | I | T | S | I | H | V | DELETED |
| I | S | N | I | T | S | I | H | V | E |
| I | S | N | I | T | S | V | Q | A | DELETED |
| I | S | N | I | T | S | V | Q | A | E |
| I | S | N | I | T | S | V | Q | V | DELETED |
| I | S | N | I | T | S | V | Q | V | E |
| I | S | N | I | T | S | V | H | A | DELETED |
| I | S | N | I | T | S | V | H | A | E |
| I | S | N | I | T | S | V | H | V | DELETED |
| I | T | S | V | S | Y | I | Q | A | DELETED |
| I | T | S | V | S | Y | I | Q | A | E |

TABLE 15-continued

Exemplary Mutations of mAb 2.6.1 Heavy Chain (SEQ ID NO: 26) to Germline at the Indicated Residue Number.

| 30 | 31 | 35 | 50 | 53 | 58 | 69 | 81 | 87 | 98 |
|---|---|---|---|---|---|---|---|---|---|
| I | T | S | V | T | S | V | H | V | E |
| I | T | S | I | S | Y | I | Q | A | DELETED |
| I | T | S | I | S | Y | I | Q | A | E |
| I | T | S | I | S | Y | I | Q | V | DELETED |
| I | T | S | I | S | Y | I | Q | V | E |
| I | T | S | I | S | Y | I | H | A | DELETED |
| I | T | S | I | S | Y | I | H | A | E |
| I | T | S | I | S | Y | I | H | V | DELETED |
| I | T | S | I | S | Y | I | H | V | E |
| I | T | S | I | S | Y | V | Q | A | DELETED |
| I | T | S | I | S | Y | V | Q | A | E |
| I | T | S | I | S | Y | V | Q | V | DELETED |
| I | T | S | I | S | Y | V | Q | V | E |
| I | T | S | I | S | Y | V | H | A | DELETED |
| I | T | S | I | S | Y | V | H | A | E |
| I | T | S | I | S | Y | V | H | V | DELETED |
| I | T | S | I | S | Y | V | H | V | E |
| I | T | S | I | S | S | I | Q | A | DELETED |
| I | T | S | I | S | S | I | Q | A | E |
| I | T | S | I | S | S | I | Q | V | DELETED |
| I | T | S | I | S | S | I | Q | V | E |
| I | T | S | I | S | S | I | H | A | DELETED |
| I | T | S | I | S | S | I | H | A | E |
| I | T | S | I | S | S | I | H | V | DELETED |
| I | T | S | I | S | S | I | H | V | E |
| I | T | S | I | S | S | V | Q | A | DELETED |
| I | T | S | I | S | S | V | Q | A | E |
| I | T | S | I | S | S | V | Q | V | DELETED |
| I | T | S | I | S | S | V | Q | V | E |
| I | T | S | I | S | S | V | H | A | DELETED |
| I | T | S | I | S | S | V | H | A | E |
| I | T | S | I | S | S | V | H | V | DELETED |
| I | T | S | I | S | S | V | H | V | E |
| I | T | S | I | T | Y | I | Q | A | DELETED |
| I | T | S | I | T | Y | I | Q | A | E |
| I | T | S | I | T | Y | I | Q | V | DELETED |
| I | T | S | I | T | Y | I | Q | V | E |
| I | T | S | I | T | Y | I | H | A | DELETED |
| I | T | S | I | T | Y | I | H | A | E |
| I | T | S | I | T | Y | I | H | V | DELETED |
| I | T | S | I | T | Y | I | H | V | E |
| I | T | S | I | T | Y | V | Q | A | DELETED |
| I | T | S | I | T | Y | V | Q | A | E |
| I | T | S | I | T | Y | V | Q | V | DELETED |
| I | T | S | I | T | Y | V | Q | V | E |
| I | T | S | I | T | Y | V | H | A | DELETED |
| I | T | S | I | T | Y | V | H | A | E |
| I | T | S | I | T | Y | V | H | V | DELETED |
| I | T | S | I | T | Y | V | H | V | E |
| I | T | S | I | T | S | I | Q | A | DELETED |
| I | T | S | I | T | S | I | Q | A | E |
| I | T | S | I | T | S | I | Q | V | DELETED |
| I | T | S | I | T | S | I | Q | V | E |
| I | T | S | I | T | S | I | H | A | DELETED |
| I | T | S | I | T | S | I | H | A | E |
| I | T | S | I | T | S | I | H | V | DELETED |
| I | T | S | I | T | S | I | H | V | E |
| I | T | S | I | T | S | V | Q | A | DELETED |
| I | T | S | I | T | S | V | Q | A | E |
| I | T | S | I | T | S | V | Q | V | DELETED |
| I | T | S | I | T | S | V | Q | V | E |
| I | T | S | I | T | S | V | H | A | DELETED |
| I | T | S | I | T | S | V | H | A | E |
| I | T | S | I | T | S | V | H | V | DELETED |
| I | T | S | I | T | S | V | H | V | E |
| I | T | N | V | S | Y | I | Q | A | DELETED |
| I | T | N | V | S | Y | I | Q | A | E |
| I | T | N | V | S | Y | I | Q | V | DELETED |
| I | T | N | V | S | Y | I | Q | V | E |
| I | T | N | V | S | Y | I | H | A | DELETED |
| I | T | N | V | S | Y | I | H | A | E |
| I | T | N | V | S | Y | I | H | V | DELETED |
| I | T | N | V | S | Y | I | H | V | E |
| I | T | N | V | S | Y | V | Q | A | DELETED |
| I | T | N | V | S | Y | V | Q | A | E |
| I | T | N | V | S | Y | V | Q | V | DELETED |
| I | T | N | V | S | Y | V | Q | V | E |
| I | T | N | V | S | Y | V | H | A | DELETED |
| I | T | N | V | S | Y | V | H | A | E |
| I | T | N | V | S | Y | V | H | V | DELETED |
| I | T | N | V | S | Y | V | H | V | E |
| I | T | N | V | S | S | I | Q | A | DELETED |
| I | T | N | V | S | S | I | Q | A | E |
| I | T | N | V | S | S | I | Q | V | DELETED |
| I | T | N | V | S | S | I | Q | V | E |
| I | T | N | V | S | S | I | H | A | DELETED |
| I | T | N | V | S | S | I | H | A | E |
| I | T | N | V | S | S | I | H | V | DELETED |
| I | T | N | V | S | S | I | H | V | E |
| I | T | N | V | S | S | V | Q | A | DELETED |
| I | T | N | V | S | S | V | Q | A | E |
| I | T | N | V | S | S | V | Q | V | DELETED |
| I | T | N | V | S | S | V | Q | V | E |
| I | T | N | V | S | S | V | H | A | DELETED |
| I | T | N | V | S | S | V | H | A | E |
| I | T | N | V | S | S | V | H | V | DELETED |
| I | T | N | V | S | S | V | H | V | E |
| I | T | N | V | T | Y | I | Q | A | DELETED |
| I | T | N | V | T | Y | I | Q | A | E |
| I | T | N | V | T | Y | I | Q | V | DELETED |
| I | T | N | V | T | Y | I | Q | V | E |
| I | T | N | V | T | Y | I | H | A | DELETED |
| I | T | N | V | T | Y | I | H | A | E |
| I | T | N | V | T | Y | I | H | V | DELETED |
| I | T | N | V | T | Y | I | H | V | E |
| I | T | N | V | T | Y | V | Q | A | DELETED |
| I | T | N | V | T | Y | V | Q | A | E |
| I | T | N | V | T | Y | V | Q | V | DELETED |
| I | T | N | V | T | Y | V | Q | V | E |
| I | T | N | V | T | Y | V | H | A | DELETED |
| I | T | N | V | T | Y | V | H | A | E |
| I | T | N | V | T | Y | V | H | V | DELETED |
| I | T | N | V | T | Y | V | H | V | E |
| I | T | N | V | T | S | I | Q | A | DELETED |
| I | T | N | V | T | S | I | Q | A | E |
| I | T | N | V | T | S | I | Q | V | DELETED |
| I | T | N | V | T | S | I | Q | V | E |
| I | T | N | V | T | S | I | H | A | DELETED |
| I | T | N | V | T | S | I | H | A | E |
| I | T | N | V | T | S | I | H | V | DELETED |
| I | T | N | V | T | S | I | H | V | E |
| I | T | N | V | T | S | V | Q | A | DELETED |
| I | T | N | V | T | S | V | Q | A | E |
| I | T | N | V | T | S | V | Q | V | DELETED |
| I | T | N | V | T | S | V | Q | V | E |
| I | T | N | V | T | S | V | H | A | DELETED |
| I | T | N | V | T | S | V | H | A | E |
| I | T | N | V | T | S | V | H | V | DELETED |
| I | T | N | V | T | S | V | H | V | E |
| I | T | N | I | S | Y | I | Q | A | DELETED |
| I | T | N | I | S | Y | I | Q | A | E |
| I | T | N | I | S | Y | I | Q | V | DELETED |
| I | T | N | I | S | Y | I | Q | V | E |
| I | T | N | I | S | Y | I | H | A | DELETED |
| I | T | N | I | S | Y | I | H | A | E |
| I | T | N | I | S | Y | I | H | V | DELETED |
| I | T | N | I | S | Y | I | H | V | E |
| I | T | N | I | S | Y | V | Q | A | DELETED |
| I | T | N | I | S | Y | V | Q | A | E |
| I | T | N | I | S | Y | V | Q | V | DELETED |
| I | T | N | I | S | Y | V | Q | V | E |
| I | T | N | I | S | Y | V | H | A | DELETED |
| I | T | N | I | S | Y | V | H | A | E |
| I | T | N | I | S | S | I | Q | A | DELETED |
| I | T | N | I | S | S | I | Q | A | E |
| I | T | N | I | S | S | I | Q | V | DELETED |
| I | T | N | I | S | S | I | Q | V | E |
| I | T | N | I | S | S | I | H | A | DELETED |

TABLE 15-continued

Exemplary Mutations of mAb 2.6.1 Heavy Chain (SEQ ID NO: 26) to Germline at the Indicated Residue Number.

| 30 | 31 | 35 | 50 | 53 | 58 | 69 | 81 | 87 | 98 |
|----|----|----|----|----|----|----|----|----|----|
| I | T | N | I | S | S | I | H | A | E |
| I | T | N | I | S | S | I | H | V | DELETED |
| I | T | N | I | S | S | I | H | V | E |
| I | T | N | I | S | S | V | Q | A | DELETED |
| I | T | N | I | S | S | V | Q | A | E |
| I | T | N | I | S | S | V | Q | V | DELETED |
| I | T | N | I | S | S | V | Q | V | E |
| I | T | N | I | S | S | V | H | A | DELETED |
| I | T | N | I | S | S | V | H | A | E |
| I | T | N | I | S | S | V | H | V | DELETED |
| I | T | N | I | S | S | V | H | V | E |
| I | T | N | I | T | Y | I | Q | A | DELETED |
| I | T | N | I | T | Y | I | Q | A | E |
| I | T | N | I | T | Y | I | Q | V | DELETED |
| I | T | N | I | T | Y | I | Q | V | E |
| I | T | N | I | T | Y | I | H | A | DELETED |
| I | T | N | I | T | Y | I | H | A | E |
| I | T | N | I | T | Y | I | H | V | DELETED |
| I | T | N | I | T | Y | I | H | V | E |
| I | T | N | I | T | Y | V | Q | A | DELETED |
| I | T | N | I | T | Y | V | Q | A | E |
| I | T | N | I | T | Y | V | Q | V | DELETED |
| I | T | N | I | T | Y | V | Q | V | E |
| I | T | N | I | T | Y | V | H | A | DELETED |
| I | T | N | I | T | Y | V | H | A | E |
| I | T | N | I | T | Y | V | H | V | DELETED |
| I | T | N | I | T | Y | V | H | V | E |
| I | T | N | I | T | S | I | Q | A | DELETED |
| I | T | N | I | T | S | I | Q | A | E |
| I | T | N | I | T | S | I | Q | V | DELETED |
| I | T | N | I | T | S | I | Q | V | E |
| I | T | N | I | T | S | I | H | A | DELETED |
| I | T | N | I | T | S | I | H | A | E |
| I | T | N | I | T | S | I | H | V | DELETED |
| I | T | N | I | T | S | I | H | V | E |
| I | T | N | I | T | S | V | Q | A | DELETED |
| I | T | N | I | T | S | V | Q | A | E |
| I | T | N | I | T | S | V | Q | V | DELETED |
| I | T | N | I | T | S | V | Q | V | E |
| I | T | N | I | T | S | V | H | A | DELETED |
| I | T | N | I | T | S | V | H | A | E |
| I | T | N | I | T | S | V | H | V | DELETED |
| I | T | N | I | T | S | V | H | V | E |

TABLE 16

Exemplary Mutations of mAb 4.18.1 Light Chain (SEQ ID NO: 52) to Germline at the Indicated Residue Number.

| 7 | 13 | 32 | 39 | 55 | 58 | 65 | 92 |
|---|----|----|----|----|----|----|----|
| S | V | N | K | A | I | S | N |
| S | V | N | K | A | I | S | G |
| S | V | N | K | A | I | I | N |
| S | V | N | K | A | I | I | G |
| S | V | N | K | A | F | S | N |
| S | V | N | K | A | F | S | G |
| S | V | N | K | A | F | I | N |
| S | V | N | K | A | F | I | G |
| S | V | N | K | S | I | S | N |
| S | V | N | K | S | I | S | G |
| S | V | N | K | S | I | I | N |
| S | V | N | K | S | I | I | G |
| S | V | N | K | S | F | S | N |
| S | V | N | K | S | F | S | G |
| S | V | N | K | S | F | I | N |
| S | V | N | K | S | F | I | G |
| S | V | N | T | A | I | S | N |
| S | V | N | T | A | I | S | G |
| S | V | N | T | A | I | I | N |
| S | V | N | T | A | I | I | G |
| S | V | N | T | A | F | S | N |
| S | V | N | T | A | F | S | G |
| S | V | N | T | A | F | I | N |
| S | V | N | T | A | F | I | G |
| S | V | N | T | S | I | S | N |
| S | V | N | T | S | I | S | G |
| S | V | N | T | S | I | I | N |
| S | V | N | T | S | I | I | G |
| S | V | N | T | S | F | S | N |
| S | V | N | T | S | F | S | G |
| S | V | N | T | S | F | I | N |
| S | V | N | T | S | F | I | G |
| S | V | S | K | A | I | S | N |
| S | V | S | K | A | I | S | G |
| S | V | S | K | A | I | I | N |
| S | V | S | K | A | I | I | G |
| S | V | S | K | A | F | S | N |
| S | V | S | K | A | F | S | G |
| S | V | S | K | A | F | I | N |
| S | V | S | K | A | F | I | G |
| S | V | S | K | S | I | S | N |
| S | V | S | K | S | I | S | G |
| S | V | S | K | S | I | I | N |
| S | V | S | K | S | I | I | G |
| S | V | S | K | S | F | S | N |
| S | V | S | K | S | F | S | G |
| S | V | S | K | S | F | I | N |
| S | V | S | K | S | F | I | G |
| S | V | S | T | A | I | S | N |
| S | V | S | T | A | I | S | G |
| S | V | S | T | A | I | I | N |
| S | V | S | T | A | I | I | G |
| S | V | S | T | A | F | S | N |
| S | V | S | T | A | F | S | G |
| S | V | S | T | A | F | I | N |
| S | V | S | T | A | F | I | G |
| S | V | S | T | S | I | S | N |
| S | V | S | T | S | I | S | G |
| S | V | S | T | S | I | I | N |
| S | V | S | T | S | I | I | G |
| S | V | S | T | S | F | S | N |
| S | V | S | T | S | F | S | G |
| S | V | S | T | S | F | I | N |
| S | V | S | T | S | F | I | G |
| S | M | N | K | A | I | S | N |
| S | M | N | K | A | I | S | G |
| S | M | N | K | A | I | I | N |
| S | M | N | K | A | I | I | G |
| S | M | N | K | A | F | S | N |
| S | M | N | K | A | F | S | G |
| S | M | N | K | A | F | I | N |
| S | M | N | K | A | F | I | G |
| S | M | N | K | S | I | S | N |
| S | M | N | K | S | I | S | G |
| S | M | N | K | S | I | I | N |
| S | M | N | K | S | I | I | G |
| S | M | N | K | S | F | S | N |
| S | M | N | K | S | F | S | G |
| S | M | N | K | S | F | I | N |
| S | M | N | K | S | F | I | G |
| S | M | N | T | A | I | S | N |
| S | M | N | T | A | I | S | G |
| S | M | N | T | A | I | I | N |
| S | M | N | T | A | I | I | G |
| S | M | N | T | A | F | S | N |
| S | M | N | T | A | F | S | G |
| S | M | N | T | A | F | I | N |
| S | M | N | T | A | F | I | G |
| S | M | N | T | S | I | S | N |
| S | M | N | T | S | I | S | G |
| S | M | N | T | S | I | I | N |
| S | M | N | T | S | I | I | G |
| S | M | N | T | S | F | S | N |
| S | M | N | T | S | F | S | G |
| S | M | N | T | S | F | I | N |
| S | M | N | T | S | F | I | G |

TABLE 16-continued

Exemplary Mutations of mAb 4.18.1 Light Chain (SEQ ID NO: 52) to Germline at the Indicated Residue Number.

| 7 | 13 | 32 | 39 | 55 | 58 | 65 | 92 |
|---|---|---|---|---|---|---|---|
| S | M | S | K | A | I | S | N |
| S | M | S | K | A | I | S | G |
| S | M | S | K | A | I | I | N |
| S | M | S | K | A | I | I | G |
| S | M | S | K | A | F | S | N |
| S | M | S | K | A | F | S | G |
| S | M | S | K | A | F | I | N |
| S | M | S | K | A | F | I | G |
| S | M | S | K | S | I | S | N |
| S | M | S | K | S | I | S | G |
| S | M | S | K | S | I | I | N |
| S | M | S | K | S | I | I | G |
| S | M | S | K | S | F | S | N |
| S | M | S | K | S | F | S | G |
| S | M | S | K | S | F | I | N |
| S | M | S | K | S | F | I | G |
| S | M | S | T | A | I | S | N |
| S | M | S | T | A | I | S | G |
| S | M | S | T | A | I | I | N |
| S | M | S | T | A | I | I | G |
| S | M | S | T | A | F | S | N |
| S | M | S | T | A | F | S | G |
| S | M | S | T | A | F | I | N |
| S | M | S | T | A | F | I | G |
| S | M | S | T | S | I | S | N |
| S | M | S | T | S | I | S | G |
| S | M | S | T | S | I | I | N |
| S | M | S | T | S | I | I | G |
| S | M | S | T | S | F | S | N |
| S | M | S | T | S | F | S | G |
| S | M | S | T | S | F | I | N |
| S | M | S | T | S | F | I | G |
| F | V | N | K | A | I | S | N |
| F | V | N | K | A | I | S | G |
| F | V | N | K | A | I | I | N |
| F | V | N | K | A | I | I | G |
| F | V | N | K | A | F | S | N |
| F | V | N | K | A | F | S | G |
| F | V | N | K | A | F | I | N |
| F | V | N | K | A | F | I | G |
| F | V | N | K | S | I | S | N |
| F | V | N | K | S | I | S | G |
| F | V | N | K | S | I | I | N |
| F | V | N | K | S | I | I | G |
| F | V | N | K | S | F | S | N |
| F | V | N | K | S | F | S | G |
| F | V | N | K | S | F | I | N |
| F | V | N | K | S | F | I | G |
| F | V | N | T | A | I | S | N |
| F | V | N | T | A | I | S | G |
| F | V | N | T | A | I | I | N |
| F | V | N | T | A | I | I | G |
| F | V | N | T | A | F | S | N |
| F | V | N | T | A | F | S | G |
| F | V | N | T | A | F | I | N |
| F | V | N | T | A | F | I | G |
| F | V | N | T | S | I | S | N |
| F | V | N | T | S | I | S | G |
| F | V | N | T | S | I | I | N |
| F | V | N | T | S | I | I | G |
| F | V | N | T | S | F | S | N |
| F | V | N | T | S | F | S | G |
| F | V | N | T | S | F | I | N |
| F | V | N | T | S | F | I | G |
| F | V | S | K | A | I | S | N |
| F | V | S | K | A | I | S | G |
| F | V | S | K | A | I | I | N |
| F | V | S | K | A | I | I | G |
| F | V | S | K | A | F | S | N |
| F | V | S | K | A | F | S | G |
| F | V | S | K | A | F | I | N |
| F | V | S | K | A | F | I | G |
| F | V | S | K | S | I | S | N |
| F | V | S | K | S | I | S | G |
| F | V | S | K | S | I | I | N |
| F | V | S | K | S | I | I | G |
| F | V | S | K | S | F | S | N |
| F | V | S | K | S | F | S | G |
| F | V | S | K | S | F | I | N |
| F | V | S | K | S | F | I | G |
| F | V | S | T | A | I | S | N |
| F | V | S | T | A | I | S | G |
| F | V | S | T | A | I | I | N |
| F | V | S | T | A | I | I | G |
| F | V | S | T | A | F | S | N |
| F | V | S | T | A | F | S | G |
| F | V | S | T | A | F | I | N |
| F | V | S | T | A | F | I | G |
| F | V | S | T | S | I | S | N |
| F | V | S | T | S | I | S | G |
| F | V | S | T | S | I | I | N |
| F | V | S | T | S | I | I | G |
| F | V | S | T | S | F | S | N |
| F | V | S | T | S | F | S | G |
| F | V | S | T | S | F | I | N |
| F | V | S | T | S | F | I | G |
| F | M | N | K | A | I | S | N |
| F | M | N | K | A | I | S | G |
| F | M | N | K | A | I | I | N |
| F | M | N | K | A | I | I | G |
| F | M | N | K | A | F | S | N |
| F | M | N | K | A | F | S | G |
| F | M | N | K | A | F | I | N |
| F | M | N | K | A | F | I | G |
| F | M | N | K | S | I | S | N |
| F | M | N | K | S | I | S | G |
| F | M | N | K | S | I | I | N |
| F | M | N | K | S | I | I | G |
| F | M | N | K | S | F | S | N |
| F | M | N | K | S | F | S | G |
| F | M | N | K | S | F | I | N |
| F | M | N | K | S | F | I | G |
| F | M | N | T | A | I | S | N |
| F | M | N | T | A | I | S | G |
| F | M | N | T | A | I | I | N |
| F | M | N | T | A | I | I | G |
| F | M | N | T | A | F | S | N |
| F | M | N | T | A | F | S | G |
| F | M | N | T | A | F | I | N |
| F | M | N | T | A | F | I | G |
| F | M | N | T | S | I | S | N |
| F | M | N | T | S | I | S | G |
| F | M | N | T | S | I | I | N |
| F | M | N | T | S | I | I | G |
| F | M | N | T | S | F | S | N |
| F | M | N | T | S | F | S | G |
| F | M | N | T | S | F | I | N |
| F | M | N | T | S | F | I | G |
| F | M | S | K | A | I | S | N |
| F | M | S | K | A | I | S | G |
| F | M | S | K | A | I | I | N |
| F | M | S | K | A | I | I | G |
| F | M | S | K | A | F | S | N |
| F | M | S | K | A | F | S | G |
| F | M | S | K | A | F | I | N |
| F | M | S | K | A | F | I | G |
| F | M | S | K | S | I | S | N |
| F | M | S | K | S | I | S | G |
| F | M | S | K | S | I | I | N |
| F | M | S | K | S | I | I | G |
| F | M | S | K | S | F | S | N |
| F | M | S | K | S | F | S | G |
| F | M | S | K | S | F | I | N |
| F | M | S | K | S | F | I | G |
| F | M | S | T | A | I | S | N |
| F | M | S | T | A | I | S | G |
| F | M | S | T | A | I | I | N |
| F | M | S | T | A | I | I | G |
| F | M | S | T | A | F | S | N |
| F | M | S | T | A | F | S | G |

TABLE 16-continued

Exemplary Mutations of mAb 4.18.1 Light Chain (SEQ ID NO: 52) to Germline at the Indicated Residue Number.

| 7 | 13 | 32 | 39 | 55 | 58 | 65 | 92 |
|---|---|---|---|---|---|---|---|
| F | M | S | T | A | F | I | N |
| F | M | S | T | A | F | I | G |
| F | M | S | T | S | I | S | N |
| F | M | S | T | S | I | S | G |
| F | M | S | T | S | I | I | N |
| F | M | S | T | S | I | I | G |
| F | M | S | T | S | F | S | N |
| F | M | S | T | S | F | S | G |
| F | M | S | T | S | F | I | N |
| F | M | S | T | S | F | I | G |

TABLE 17

Exemplary Mutations of mAb 4.18.1 Heavy Chain (SEQ ID NO: 50) to Germline at the Indicated Residue Number.

| 30 | 31 | 35 | 53 | 75 | 98-99 | 103 | 117 |
|---|---|---|---|---|---|---|---|
| S | S | S | S | K | EG | G | S |
| S | S | S | S | K | EG | G | L |
| S | S | S | S | K | EG | DELETED | S |
| S | S | S | S | K | EG | DELETED | L |
| S | S | S | S | K | DELETED | G | S |
| S | S | S | S | K | DELETED | G | L |
| S | S | S | S | K | DELETED | DELETED | S |
| S | S | S | S | K | DELETED | DELETED | L |
| S | S | S | S | R | EG | G | S |
| S | S | S | S | R | EG | G | L |
| S | S | S | S | R | EG | DELETED | S |
| S | S | S | S | R | EG | DELETED | L |
| S | S | S | S | R | DELETED | G | S |
| S | S | S | S | R | DELETED | G | L |
| S | S | S | S | R | DELETED | DELETED | S |
| S | S | S | S | R | DELETED | DELETED | L |
| S | S | S | T | K | EG | G | S |
| S | S | S | T | K | EG | G | L |
| S | S | S | T | K | EG | DELETED | S |
| S | S | S | T | K | EG | DELETED | L |
| S | S | S | T | K | DELETED | G | S |
| S | S | S | T | K | DELETED | G | L |
| S | S | S | T | K | DELETED | DELETED | S |
| S | S | S | T | K | DELETED | DELETED | L |
| S | S | S | T | R | EG | G | S |
| S | S | S | T | R | EG | G | L |
| S | S | S | T | R | EG | DELETED | S |
| S | S | S | T | R | EG | DELETED | L |
| S | S | S | T | R | DELETED | G | S |
| S | S | S | T | R | DELETED | G | L |
| S | S | S | T | R | DELETED | DELETED | S |
| S | S | S | T | R | DELETED | DELETED | L |
| S | S | N | S | K | EG | G | S |
| S | S | N | S | K | EG | G | L |
| S | S | N | S | K | EG | DELETED | S |
| S | S | N | S | K | EG | DELETED | L |
| S | S | N | S | K | DELETED | G | S |
| S | S | N | S | K | DELETED | G | L |
| S | S | N | S | K | DELETED | DELETED | S |
| S | S | N | S | K | DELETED | DELETED | L |
| S | S | N | S | R | EG | G | S |
| S | S | N | S | R | EG | G | L |
| S | S | N | S | R | EG | DELETED | S |
| S | S | N | S | R | EG | DELETED | L |
| S | S | N | S | R | DELETED | G | S |
| S | S | N | S | R | DELETED | G | L |
| S | S | N | S | R | DELETED | DELETED | S |
| S | S | N | S | R | DELETED | DELETED | L |
| S | S | N | T | K | EG | G | S |
| S | S | N | T | K | EG | G | L |
| S | S | N | T | K | EG | DELETED | S |
| S | S | N | T | K | EG | DELETED | L |
| S | S | N | T | K | DELETED | G | S |
| S | S | N | T | K | DELETED | G | L |
| S | S | N | T | K | DELETED | DELETED | S |
| S | S | N | T | K | DELETED | DELETED | L |
| S | S | N | T | R | EG | G | S |
| S | S | N | T | R | EG | G | L |
| S | S | N | T | R | EG | DELETED | S |
| S | S | N | T | R | EG | DELETED | L |
| S | S | N | T | R | DELETED | G | S |
| S | S | N | T | R | DELETED | G | L |
| S | S | N | T | R | DELETED | DELETED | S |
| S | S | N | T | R | DELETED | DELETED | L |
| S | N | S | S | K | EG | G | S |
| S | N | S | S | K | EG | G | L |
| S | N | S | S | K | EG | DELETED | S |
| S | N | S | S | K | EG | DELETED | L |
| S | N | S | S | K | DELETED | G | S |
| S | N | S | S | K | DELETED | G | L |
| S | N | S | S | K | DELETED | DELETED | S |
| S | N | S | S | K | DELETED | DELETED | L |
| S | N | S | S | R | EG | G | S |
| S | N | S | S | R | EG | G | L |
| S | N | S | S | R | EG | DELETED | S |
| S | N | S | S | R | EG | DELETED | L |
| S | N | S | S | R | DELETED | G | S |
| S | N | S | S | R | DELETED | G | L |
| S | N | S | S | R | DELETED | DELETED | S |
| S | N | S | S | R | DELETED | DELETED | L |
| S | N | S | T | K | EG | G | S |
| S | N | S | T | K | EG | G | L |
| S | N | S | T | K | EG | DELETED | S |
| S | N | S | T | K | EG | DELETED | L |
| S | N | S | T | K | DELETED | G | S |
| S | N | S | T | K | DELETED | G | L |
| S | N | S | T | K | DELETED | DELETED | S |
| S | N | S | T | K | DELETED | DELETED | L |
| S | N | S | T | R | EG | G | S |
| S | N | S | T | R | EG | G | L |
| S | N | S | T | R | EG | DELETED | S |
| S | N | S | T | R | EG | DELETED | L |
| S | N | S | T | R | DELETED | G | S |
| S | N | S | T | R | DELETED | G | L |
| S | N | S | T | R | DELETED | DELETED | S |
| S | N | S | T | R | DELETED | DELETED | L |
| S | N | N | S | K | EG | G | S |
| S | N | N | S | K | EG | G | L |
| S | N | N | S | K | EG | DELETED | S |
| S | N | N | S | K | EG | DELETED | L |
| S | N | N | S | K | DELETED | G | S |
| S | N | N | S | K | DELETED | G | L |
| S | N | N | S | K | DELETED | DELETED | S |
| S | N | N | S | K | DELETED | DELETED | L |
| S | N | N | S | R | EG | G | S |
| S | N | N | S | R | EG | G | L |
| S | N | N | S | R | EG | DELETED | S |
| S | N | N | S | R | EG | DELETED | L |
| S | N | N | S | R | DELETED | G | S |
| S | N | N | S | R | DELETED | G | L |
| S | N | N | S | R | DELETED | DELETED | S |
| S | N | N | S | R | DELETED | DELETED | L |
| S | N | N | T | K | EG | G | S |
| S | N | N | T | K | EG | G | L |
| S | N | N | T | K | EG | DELETED | S |
| S | N | N | T | K | EG | DELETED | L |
| S | N | N | T | K | DELETED | G | S |
| S | N | N | T | K | DELETED | G | L |
| S | N | N | T | K | DELETED | DELETED | S |
| S | N | N | T | K | DELETED | DELETED | L |
| S | N | N | T | R | EG | G | S |
| S | N | N | T | R | EG | G | L |
| S | N | N | T | R | EG | DELETED | S |
| S | N | N | T | R | EG | DELETED | L |
| S | N | N | T | R | DELETED | G | S |
| S | N | N | T | R | DELETED | G | L |
| S | N | N | T | R | DELETED | DELETED | S |
| S | N | N | T | R | DELETED | DELETED | L |
| R | S | S | S | K | EG | G | S |

TABLE 17-continued

Exemplary Mutations of mAb 4.18.1 Heavy Chain (SEQ ID NO: 50) to Germline at the Indicated Residue Number.

| 30 | 31 | 35 | 53 | 75 | 98-99 | 103 | 117 |
|----|----|----|----|----|-------|-----|-----|
| R | S | S | S | K | EG | G | L |
| R | S | S | S | K | EG | DELETED | S |
| R | S | S | S | K | EG | DELETED | L |
| R | S | S | S | K | DELETED | G | S |
| R | S | S | S | K | DELETED | G | L |
| R | S | S | S | K | DELETED | DELETED | S |
| R | S | S | S | K | DELETED | DELETED | L |
| R | S | S | S | R | EG | G | S |
| R | S | S | S | R | EG | G | L |
| R | S | S | S | R | EG | DELETED | S |
| R | S | S | S | R | EG | DELETED | L |
| R | S | S | S | R | DELETED | G | S |
| R | S | S | S | R | DELETED | G | L |
| R | S | S | S | R | DELETED | DELETED | S |
| R | S | S | S | R | DELETED | DELETED | L |
| R | S | S | T | K | EG | G | S |
| R | S | S | T | K | EG | G | L |
| R | S | S | T | K | EG | DELETED | S |
| R | S | S | T | K | EG | DELETED | L |
| R | S | S | T | K | DELETED | G | S |
| R | S | S | T | K | DELETED | G | L |
| R | S | S | T | K | DELETED | DELETED | S |
| R | S | S | T | K | DELETED | DELETED | L |
| R | S | S | T | R | EG | G | S |
| R | S | S | T | R | EG | G | L |
| R | S | S | T | R | EG | DELETED | S |
| R | S | S | T | R | EG | DELETED | L |
| R | S | S | T | R | DELETED | G | S |
| R | S | S | T | R | DELETED | G | L |
| R | S | S | T | R | DELETED | DELETED | S |
| R | S | S | T | R | DELETED | DELETED | L |
| R | S | N | S | K | EG | G | S |
| R | S | N | S | K | EG | G | L |
| R | S | N | S | K | EG | DELETED | S |
| R | S | N | S | K | EG | DELETED | L |
| R | S | N | S | K | DELETED | G | S |
| R | S | N | S | K | DELETED | G | L |
| R | S | N | S | K | DELETED | DELETED | S |
| R | S | N | S | K | DELETED | DELETED | L |
| R | S | N | S | R | EG | G | S |
| R | S | N | S | R | EG | G | L |
| R | S | N | S | R | EG | DELETED | S |
| R | S | N | S | R | EG | DELETED | L |
| R | S | N | S | R | DELETED | G | S |
| R | S | N | S | R | DELETED | G | L |
| R | S | N | S | R | DELETED | DELETED | S |
| R | S | N | S | R | DELETED | DELETED | L |
| R | S | N | T | K | EG | G | S |
| R | S | N | T | K | EG | G | L |
| R | S | N | T | K | EG | DELETED | S |
| R | S | N | T | K | EG | DELETED | L |
| R | S | N | T | K | DELETED | G | S |
| R | S | N | T | K | DELETED | G | L |
| R | S | N | T | K | DELETED | DELETED | S |
| R | S | N | T | K | DELETED | DELETED | L |
| R | S | N | T | R | EG | G | S |
| R | S | N | T | R | EG | G | L |
| R | S | N | T | R | EG | DELETED | S |
| R | S | N | T | R | EG | DELETED | L |
| R | S | N | T | R | DELETED | G | S |
| R | S | N | T | R | DELETED | G | L |
| R | S | N | T | R | DELETED | DELETED | S |
| R | S | N | T | R | DELETED | DELETED | L |
| R | N | S | S | K | EG | G | S |
| R | N | S | S | K | EG | G | L |
| R | N | S | S | K | EG | DELETED | S |
| R | N | S | S | K | EG | DELETED | L |
| R | N | S | S | K | DELETED | G | S |
| R | N | S | S | K | DELETED | G | L |
| R | N | S | S | K | DELETED | DELETED | S |
| R | N | S | S | K | DELETED | DELETED | L |
| R | N | S | S | R | EG | G | S |
| R | N | S | S | R | EG | G | L |
| R | N | S | S | R | EG | DELETED | S |
| R | N | S | S | R | EG | DELETED | L |
| R | N | S | S | R | DELETED | G | S |
| R | N | S | S | R | DELETED | G | L |
| R | N | S | S | R | DELETED | DELETED | S |
| R | N | S | S | R | DELETED | DELETED | L |
| R | N | S | T | K | EG | G | S |
| R | N | S | T | K | EG | G | L |
| R | N | S | T | K | EG | DELETED | S |
| R | N | S | T | K | EG | DELETED | L |
| R | N | S | T | K | DELETED | G | S |
| R | N | S | T | K | DELETED | G | L |
| R | N | S | T | K | DELETED | DELETED | S |
| R | N | S | T | K | DELETED | DELETED | L |
| R | N | S | T | R | EG | G | S |
| R | N | S | T | R | EG | G | L |
| R | N | S | T | R | EG | DELETED | S |
| R | N | S | T | R | EG | DELETED | L |
| R | N | S | T | R | DELETED | G | S |
| R | N | S | T | R | DELETED | G | L |
| R | N | S | T | R | DELETED | DELETED | S |
| R | N | S | T | R | DELETED | DELETED | L |
| R | N | N | S | K | EG | G | S |
| R | N | N | S | K | EG | G | L |
| R | N | N | S | K | EG | DELETED | S |
| R | N | N | S | K | EG | DELETED | L |
| R | N | N | S | K | DELETED | G | S |
| R | N | N | S | K | DELETED | G | L |
| R | N | N | S | K | DELETED | DELETED | S |
| R | N | N | S | K | DELETED | DELETED | L |
| R | N | N | S | R | EG | G | S |
| R | N | N | S | R | EG | G | L |
| R | N | N | S | R | EG | DELETED | S |
| R | N | N | S | R | EG | DELETED | L |
| R | N | N | S | R | DELETED | G | S |
| R | N | N | S | R | DELETED | G | L |
| R | N | N | S | R | DELETED | DELETED | S |
| R | N | N | S | R | DELETED | DELETED | L |
| R | N | N | T | K | EG | G | S |
| R | N | N | T | K | EG | G | L |
| R | N | N | T | K | EG | DELETED | S |
| R | N | N | T | K | EG | DELETED | L |
| R | N | N | T | K | DELETED | G | S |
| R | N | N | T | K | DELETED | G | L |
| R | N | N | T | K | DELETED | DELETED | S |
| R | N | N | T | K | DELETED | DELETED | L |
| R | N | N | T | R | EG | G | S |
| R | N | N | T | R | EG | G | L |
| R | N | N | T | R | EG | DELETED | S |
| R | N | N | T | R | EG | DELETED | L |
| R | N | N | T | R | DELETED | G | S |
| R | N | N | T | R | DELETED | G | L |
| R | N | N | T | R | DELETED | DELETED | S |
| R | N | N | T | R | DELETED | DELETED | L |

TABLE 18

Heavy chain analysis

| Chain Name | SEQ ID NO: | V | D | J | FR1 | CDR1 | FR2 | CDR2 | FR3 | CDR3 | FR4 |
|---|---|---|---|---|---|---|---|---|---|---|---|
| | 70 | Germline | | | EVQLVESGGGLVQ PGGSLRLSCAASG FTFS | SYDMH | WVRQATG KGLEWVS | AIGTAGDT YYPGSVKG | RFTISRENAKNSLYLQ MNSLRAGDTAVYYCAR | DYSNYTMVRG VYGMDV | WGQGTT VTVSS |
| 1.4.2g2 | 2 | VH3-13 | D3-10 | JH6B | EVQLVESGGGLVQ PGGSLRLSCAASG FTFS | SYDMH | WVRQATG KGLEWVS | AIGTAGDT YYPGSVKG | RFTISRENAKNSLYLQ MNSLRAGDTAVYYCAR | EGDYSNYFTM VRGVTYGMDV | WGQGTT VTVSS |
| 1.61.1 g2 | 10 | VH3-13 | D3-10 | JH6B | EVQLVESGGGLVQ PGGSLRLSCAASG FTFS | SYDMH | WVRQATG KGLEWVS | AIGTAGDT YYPGSVKG | RFTISRENAKNSLYLQ MNSLRAGDTAVYYCAR | EGDYSNYFTR VRGVTYGMDV | WGQGTT VTVSS |
| | 71 | Germline | | | EVQLLESGGGLVQ PGGSLRLSCAASG FTFS | SYAMS | WVRQAPG KGLEWVS | AISGSGGS TYYADSVK G | RFTISRDNSKNTLYLQ MNSLRAEDTAVYYCAK | YGDYWYFDL | WGRGTL VTVSS |
| 4.13.1 g4 | 46 | VH3-23 | D4-17 | JH2 | EVQLLESGGGVLQ PGGSLRLSCAASG FTFS | SYAMS | WVRQAPG KGLEWVL | GISGSGGS TYYADSVK G | RFTISRDNSKNTLYLQ MNSLRAEDTAVYYCAK | DGYDGYVGWY FKL | WGRGTL VTVSS |
| | 72 | Germline | | | QVQLVESGGGVVQ PGRSLRLSCAASG FTFS | SYGMH | WVRQAPG KGLEWVA | VIWYDGSN KYYADSVK G | RFTISRDNSKNTLYLQ MNSLRAEDTAVYYCAR | DMIVVITAF DI | WGQGTM VTVSS |
| 4.50.1 g4 | 58 | VH3-33 | D3-22 | JH3B | QVQLVESGGGVVQ PGRSLRLSCAASG FTFS | SYGMH | WVRQAPG KGLEWVA | VIWYDGSN KDYADSVK G | RFTISRDNSKNTLYLQ MNSLRAEDTAVYYCAR | DMIVVITYA FDI | WGQGTM VTVSS |
| | 73 | Germline | | | QVQLVESGGGVVQ PGRSLRLSCAASG FTFS | SYGMH | WVRQAPG KGLEWVA | VIWYDGSN KYYADSVK G | RFTISRDNSKNTLYLQ MNSLRAEDTAVYYCAR | YYYYYGMDV | WGQGTT VTVSS |
| 1.41.1 g2 | 6 | VH3-33 | D6-6 | JH6B | QVQLVESGGGVVQ PGRSLRLSCAAPG FTFS | SYGMH | WVRQAPG KGLEWVA | VIWYDGSQ KYYADSVK G | RFTISRDNSKNTLYQ MNSLRAEDTAVYYCAR | GMTYYYYGM DV | WGQGTT VTVSS |
| 1.113. 2g2 | 22 | VH3-33 | D6-6 | JH6B | QVQLVESGGGVVQ PGRSLRLSCAASG FTFS | SYGMH | WVRQAPG KGLEWVA | VIWYDGSN KYYADSVK G | RFTISRDNSKNTLYLQ MNSLRAEDTAVYYCAR | DLAALYYYYG MHV | WGQGTT VTVSS |
| | 74 | Germline | | | EVQLVESGGGLIQ PGGSLRLSCAASG FTVS | SNYMS | WVRQAPG KGLEWVS | VIYSGGST YYADSVKG | RFTISRDNSKNTLYLQ MNSLRAEDTAVYYCAR | AVAFDY | WGQGTL VTVSS |
| 1.99.1 g2 | 14 | VH3-53 | D6-19 | JH4B | EVQLVESGGGLIQ PGGSLRLSCAASG FTVR | SNYMS | WVRQAPG KGLEWIS | VIYTGGST YYADSVKG | RFSISRDNSKNTLYLQ MNSLRAEDTAVYYCAR | EGAVAGFDY | WGQGTL VTVSS |
| 4.18.1 g4 | 50 | VH3-53 | D6-19 | JH4B | EVQLVESGGGLIQ PGGSLRLSCAASG FTVR | NNYMN | WVRQAPG KGLEWVS | VIYTGGST YYADSVKG | RFTISRDNSRNTLYLQ MNSLRAEDTAVYYCAR | EGAVAGFDY | WGQGTL VTVSL |
| | 75 | Germline | | | EVQLVESGGGLIQ PGGSLRLSCAASG FTVS | SNYMS | WVRQAPG KGLEWVS | VIYSGGST YYADSVKG | RFTISRDNSKNTLYLQ MNSLRAEDTAVYYCAR | YYYYYGMDV | WGQGTT VTVSS |
| 1.100. 1g2 | 18 | VH3-53 | | JH6B | EVQLVESGGGLLQ PGGSLRLSCAASG FTVR | NNYMN | WVRQAPG KGLEWVS | VIYTGGST YYADSVKG | RFTISRDNSKNTLYLQ MNSLRAEDTAVYYCAR | EGKLAGMDV | WGQGTT VTVSS |
| 4.19.1 g4 | 54 | VH3-53 | | JH6B | EVQLVESGGGLIQ PGGSLRLSCAASG FSVS | SNYMN | WVRQAPG KGLEWVS | VIYTGGST YYADSVKG | RFTISRDNSKNTLYLQ MNSLRAEDTAVYYCAR | DTYLYGMDV | WGQGTT VTVSS |
| | 76 | Germline | | | EVQLVESGGGLVQ PGGSLRLSCAASG FTFS | SYWMS | WVRQAPG KGLEWVA | NIKQDGSE SYYVDSVK MNSLRAEDTAVYYCAR G | RFTISRDNAKNSLYLQ | GWYWYFDL | WGRGTL VTVSS |
| 4.12.1 g4 | 42 | VH3-7 | D6-19 | JH2 | EVQLVESGGGLVQ PGGSLRLSCAASG FTFS | SYWMS | WVRQAPG TGLDWVA | NINQDGSE RYYVDSVK G | RFTISRDNAKNSPHLQ MNSLRAEDTAVYYCAR | EGSGGRYGGW YFDL | WGRGTL VTVSS |

TABLE 18-continued

Heavy chain analysis

| Chain Name | SEQ ID NO: | V | D | J | FR1 | CDR1 | FR2 | CDR2 | FR3 | CDR3 | FR4 |
|---|---|---|---|---|---|---|---|---|---|---|---|
| | 77 | Germline | | | QVQLVESGGGVVQ PGRSLRLSCAASG FTFS | SYGMH | WVRQAPG KGLEWVA | VIWYDGSN KYYADSVK G | RFTISRDNSKNTLYLQ MNSLRAEDTAVYYCAR | HIVVVTAILD Y | WGQGTL VTVSS |
| 2.19.2 g2 | 30 | VH3-33 | D2-21 | JH4B | QVQLVESGGGVVQ PGRSLRLSCAASG FTFS | SYGMH | WVRQAPG KGLEWVA | VIWYDGSN KYYADSVK G | RFTISRDNSKNTLYLQ MNSLRAEDTAVYYCAR | DQHIVVVTAI LDY | WGQGTL VTVSS |
| | 78 | Germline | | | EVQLVESGGGLIQ PGGSLRLSCAASG FTVS | SNYMS | WVRQAPG KGLEWVS | VIYSGGST YYADSVKG | RFTISRDNSKNTLYLQ MNSLRAEDTAVYYCAR | IAVAGYYGMD V | WGQGTT VTVS |
| 2.6.1g 2 | 26 | VH3-53 | D6-19 | JH6B | EVQLVESGGGLIQ PGGSLRLSCAASG FTVI | TNYMN | WVRQAPG KGLEWVS | IIYTGGST SYADSVKG | RFTVSRDNSKNTLYLH MNSLRVEDTAVYYCAR | EIAVAGYYGM DV | WGQGTT VTVS |
| | 79 | Germline | | | EVQLVESGGGLVQ PGGSLRLSCAASG FTFS | SYWMS | WVRQAPG DGLEWVA | NIKQDGSE KYYVDSVK G | RFTISRDNAKNSLYLQ MNSLRAEDTAVYYCAR | YYYDSSGYYW YFDL | WGRGTL VTVSS |
| 3.8.3g 2 | 34 | VH3-7 | D3-22 | JH2 | EVQLVESGGGLVQ PGGSLRLSCAASG FTFS | SYMNS | WVRQAPG KGLEWVA | NIKQHGSE DYYVDSVK G | RFTISRDNAKNSLYLQ MNSLRAEDTAVYYCAR | EEAYYYDNSG YYWYFDL | WARGTL VTVSS |
| | 80 | Germline | | | QVQLQESGPGLVK PSQTLSLTCTVSG GSIS | SGGYY WS | WIRQHPG KGLEWIG | YIYYSGST YYNPSLKS | RVTISVDTSKNQFSLK LSSVTAADTAVYYCAR | YYYYYGMDV | WGQGTT VTVSS |
| 3.176. 2g2 | 38 | VH4-31 | D2-21 | JH6B | QVQLQESGPGLVK PSQTLSLTCTVSG GSIS | SGGHY WS | WIRQHPG KGLEWIG | YIYYSGRT YYNPSLKS | RVTISVDTSKNQFSLK LSSVTAADTAVYYCAR | DGTGDYYYYG MDV | WGQGTT VTVSS |

TABLE 19

Light chain analysis

| Chain Name | SEQ ID NO: | V | J | FR1 | CDR1 | FR2 | CDR2 | FR3 | CDR3 | FR4 |
|---|---|---|---|---|---|---|---|---|---|---|
| | 61 | Germline | | DIVMTQSPD- SLA VSLGERATINC | KSSQSVLYS SNNKNYLA | WYQQKPGQ PPKLLIY | WAST RES | GVPDRFSGSGSGTDFT LTISSLQAEDVAVYYC | QQYYSFGQGTK TPPT | VEIK |
| 4.13.1k | 48 | B3 | JK1 | DIVMTQSPD- SLA VSLGERATINC | KSSQSVLYS SNNKNFLA | WYQQKPGQ PPKLLIY | WAST RES | GVPDRFSGSGSGTDFT LTISNLQAEDVAVYYC | QQFYSFGQGTK TPPT | VEIR |
| 4.50.1k | 60 | B3 | JK1 | DIVMTQSPD- SLA VSLGERATINC | KSSQSVLYS SNNKNYLA | WYQQKSGQ PPKLLIY | WAST RES | GVPDRFSGSGSGTDFT LTISSLQAEDVAVYYC | QQYYRFGQGTR TPPT | VEIK |
| 2.19.2k | 32 | B3 | JK1 | DIVMTQSPD- SLS VSLGERATINC | KSSQSVLYG SNNRNSLA | WYQQKPGQ PPKLLIY | WAST RES | GVPDRFSGSGSGTDFT LTISSLQAEDVAVYYC | QQYYSFGQGTK IFPWTVEIK | |
| | 62 | Germline | | DIVMTQSPD- SLA VSLGERATINC | KSSQSVLYS SNNKNYLA | WYQQKPGQ PPKLLIY | WAST RES | GVPDRFSGSGSGTDFT LTISSLQAEDVAVYYC | QQYYSFGQGTR TPPITLEIK | |
| 4.12.1k | 44 | B3 | JK5 | DIVMTQSPD- SLA VSLGERATINC | KSSQSVLYS SNNKNFLA | WYQQKPGQ PPKLLIY | WAST RES | GVPDRFSGSGSGTDFT LTISSLQAEDVAVYYC | QQYYSFGQGTR TPPITLEIK | |
| | 63 | Germline | | DIQMTQSPSSLS ASVGDRVTITC | RASQGISNY LA | WFQQKPGK APKSLIY | AASS LQS | GVPSRFSGSGSGTDFT LTISSLQPEDFATYYC | QQYNSFGGGTK YPLT | VEIK |
| 1.4.2k | 4 | L1 | JK4 | DIQLTQSPSSLS ASVGDRITITC | RASQGISKY LA | WFQQKPGK APKSLIY | GASS LQS | GVPAKFSGSGSGTDFT LTISSLQPEDFATYYC | QQYNSFGGGTK YPLT | VEIK |
| 1.61.1k | 12 | L1 | JK4 | DIQMTQSPSSLS ASVGDRVTITC | RASQGISKY LA | WFQQKPGK APKSLIY | GASS LQS | GVPSKFSGSGSGTDFT LTISSLQPEDFATYYC | QQYNSFGGGTK YPLT | VEIK |

TABLE 19-continued

Light chain analysis

| Chain Name | SEQ ID NO: | V | J | FR1 | CDR1 | FR2 | CDR2 | FR3 | CDR3 | FR4 |
|---|---|---|---|---|---|---|---|---|---|---|
|  | 64 | Germline |  | EIVMTQS-PATLS VSPGERATLSC | RASQSVSSN LA | WYQQKPGQ APRLLIY | GAST RAT | GIPARFSGSGSGTEFT LTISSLQSEDFAVYYC | QQYNNFGQGTK WPRT | VEIK |
| 1.113.2k | 24 | L2 | JK1 | EIVMTQS-PATLS VSPGERATLSC | RASQSFSSN LA | WYQQKPGQ APRLLIY | GAST RAT | GIPARFSGSGSGTEFT LTISSLQSEDFAVYYC | QQNNNFGQGTK WPRT | VEIK |
| 1.41.1k | 8 | L2 | JK1 | EIVMTQS-PAILS VSPGERATLSC | RASQSVSSK LD | WYQQKPGQ APRLLIY | GAST RAT | GIPARFSGSGSGTEFT LTISSLQSEDFAVYYC | QQYNNFGQGTK WPRT | VEIK |
|  | 65 | Germline |  | EIVMTQS-PATLS VSPGERATLSC | RASQSVSSN LA | WYQQKPGQ APRLLIY | GAST RAT | GIPARFSGSGSGTEFT LTISSLQSEDFAVYYC | QQYNNFGGGTK WPLT | VEIK |
| 1.99.1k | 16 | L2 | JK4 | EIVMTQS-PATLS VSPGERATLSC | RASQSISSN LA | WYQQKPGQ APRLLIY | GAST RAT | GIPARFSGSGSGTEFT LTISSLQSEDFAVYYC | QQYTNFGGGTK WPLT | VEIK |
| 4.19.1k | 56 | L2 | JK4 | EIVMTQS-PATLS VSPGESATLSC | RTSQSVSSN LA | WYQQKPGQ TPRLLIY | GASA RAT | GVPARFSGSGSGTEFT LTISSLQSEDFAVYYC | QQYYNFGGGTK WPLT | VEIK |
| 1.100.1k | 20 | L2 | JK4 | ETVMTQS-PATLS VSPGERATLSC | RASQSVSSN LA | WYQQKPGQ APRLLIY | GAST RAT | GIPARFSGSGSGTEFT LTISSLQSEEFAVYYC | QQYNNFGGGTK WPLT | VEIK |
|  | 66 | Germline |  | EIVMTQS-PATLS VSPGERATLSC | RASQSVSSN LA | WYQQKPGQ APRLLIY | GAST RAT | GIPARFSGSGSGTEFT LTISSLQSEDFAVYYC | QQYNNFGQGTR WPLT | LEIK |
| 4.18.1k | 52 | L2 | JK5 | EIVMTQF-PATLS MSPGERATLSC | RASQSVSSS LA | WYQQTPGQ APRLLIY | GAST RST | GFPARFSGIGSGTEFT LTISSLQSEDFAVYYC | QQYGNFGQGTR WPLT | LEIK |
|  | 67 | Germline |  | DIQMTQSPSSL-ASVGDRVTITC | SRASQGIRND LG | WYQQKPGK APKRLIY | AASS LQS | GVPSRFSGSGSGTEFT LTISSLQPEDFATYYC | LQHNSFGGGTK YT | VEIK |
| 2.6.1k | 28 | A30 | JK4 | DIQMTQSPSSL-ASVGDRVTITC | SRASQGIRND LG | WYQQKPGK APKRLIY | AASS LQS | GVPSRFSGSGSGTEFT LTISSLQPEDFATYYC | LQHNSFGGGTK YPLT | VEIK |
|  | 68 | Germline |  | DIVMTQSPD-SLA VSLGERATINC | KSSQSVLYS SNNKNYLA | WYQQKPGQ PPKLLIY | WAST RES | GVPDRFSGSGSGTDFT LTISSLQAEDVAVYYC | QQYYSFGGGTK TT | VEIK |
| 3.176.2k | 40 | B3 | JK4 | DIVMTQSPTSL-VSLGERATINC | TKSSQSVLYS SNNRNFLA | WYQQKPRQ PPKLLIY | WAST RES | GVPDRFSGSGSGTDFT LTISSLQAEDVAVYYC | QQYYTFGGGTK TPLT | VEIK |
|  | 69 | Germline |  | DIQMTQSPSSV-ASVGDRVTITC | SRASQGISSW LA | WYQQKPGK APKLLIY | AASS LQS | GVPSRFSGSGSGTDFT LTISSLQPEDFATYYC | QQANSFGQGTK FPWT | VEIK |
| 3.8.3k | 36 | L5 | JK1 | DIQMTQSPSSV-ASIGDRVTITC | SRASQGISSW LA | WYQQKPGK TPKLLIY | AASS LQS | GVPSRFSGSGSGTDFT LTISSLQPEDFATYYC | QQADSFGQGTK FPWT | VEIK |

Example 16

Identification of uPAR Binding Epitopes

Figure 6:
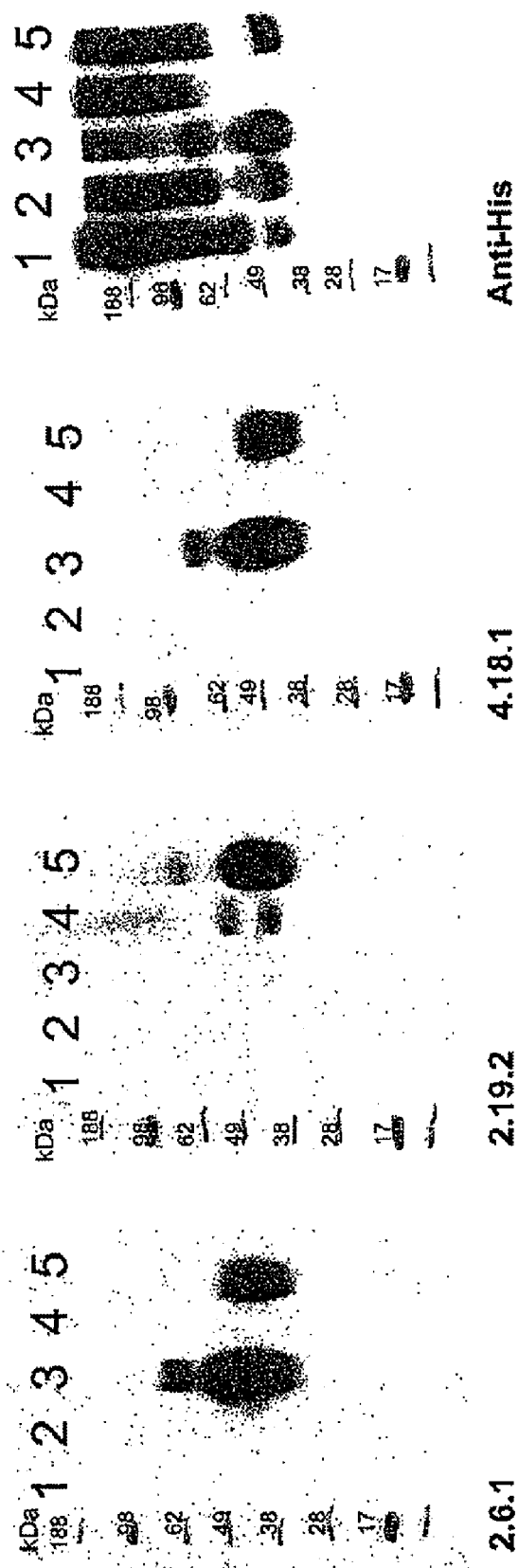
FIG. 6 shows the results of epitope binding analysis of anti-human uPAR mAbs by Western Blotting. Human-murine uPAR chimeras (His-tagged) were expressed in BEK293T cells and uPAR expression was detected using the anti-human uPAR mAbs as indicated. Lane 1—murine DI/DIII—human DII; lane 2—murine DI/DII—human DIII; lane 3—murine DI—human DII/DIII; lane 4—human DI/DII—murine DIII; lane 5—human uPAR.

As the anti-uPAR antibodies failed to cross-react with mouse uPAR, we generated a number of mouse uPAR-human uPAR chimeric proteins to identify the domains involved in antibody binding. Chimeric human-murine uPAR comprising murine D1/humanD2D3; murine D1/human D2/MuD3; and human D1D2/murineD3uPAR each with a C-terminal His tag were expressed as secreted proteins in HEK293T cells. Binding sites for 2.6.1, 2.19.2, and 4.18.1 were determined by Western blotting of culture supernatants; expression of the appropriate recombinant proteins was demonstrated by detection using anti-His mAb. The binding epitope for 2.19.2 lies in Domain I, and 2.6.1 interacts primarily with an epitope within Domain II/III and 4.18.1 with an epitope in Domain II (see FIG. 6).

The nucleotide sequences encoding the proteins used for the epitope binning and the translated amino acid sequence are set forth in Table 20 below.

TABLE 20

| Nucleotide and Amino Acid Sequences Used for Epitope Binning | | |
|---|---|---|
| uPAR ECD Chimera | Sequence | SEQ ID NO: |
| Murine D1/Human D2D3 | Nucleotide Sequence | SEQ ID NO: 83 |
|  | Amino Acid Sequence | SEQ ID NO: 84 |

TABLE 20-continued

Nucleotide and Amino Acid Sequences Used for Epitope Binning

| uPAR ECD Chimera | Sequence | SEQ ID NO: |
|---|---|---|
| Human D1D2/Murine D3 | Nucleotide Sequence | SEQ ID NO: 85 |
| | Amino Acid Sequence | SEQ ID NO: 86 |
| Murine D1/Human D2/Murine D3 | Nucleotide Sequence | SEQ ID NO: 87 |
| | Amino Acid Sequence | SEQ ID NO: 88 |
| Murine D1D2/Human D3 | Nucleotide Sequence | SEQ ID NO: 89 |
| | Amino Acid Sequence | SEQ ID NO: 90 |

Example 17

Inhibition of Tumor Growth and Metastasis In Vivo

Figure 7:
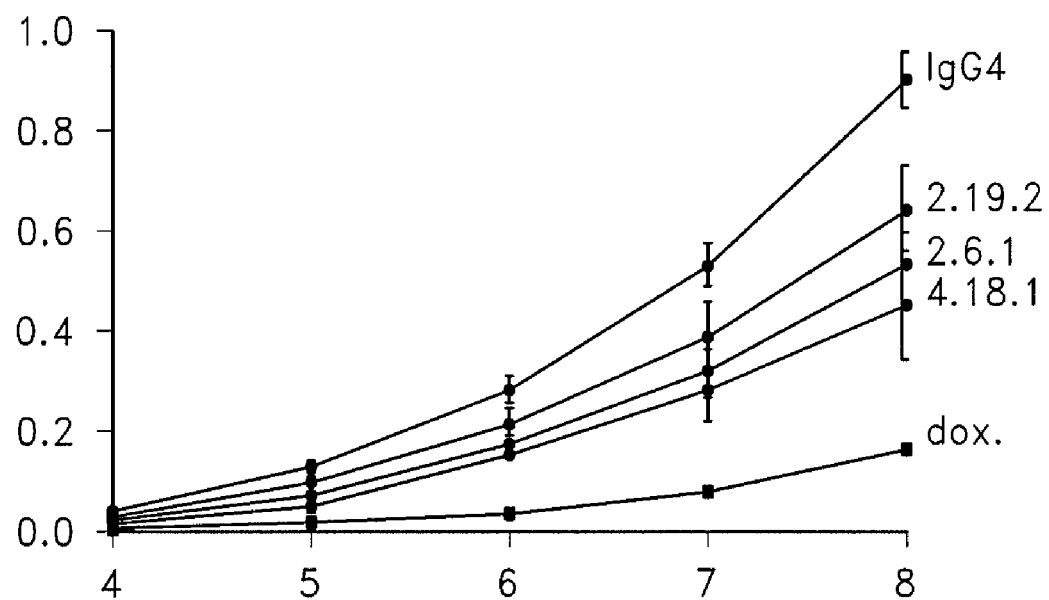
FIG. 7 is a line graph showing the effect of anti-uPAR mAbs on solid tumor growth of MDA-MB231-GFP orthotopic xenografts. Mean tumor volume (in $cm^3$) at time points post transplantation (weeks post implant) are shown for each antibody tested, and for IgG4 isotype and doxorubicin controls. Untreated control tumor growth (not shown) was not significantly different to IgG4 isotype controls.

MDA MB231 cells stably expressing GFP (MDA MB231-GFP cells) were grown in culture and harvested at 85% confluence. A total of $5 \times 10^5$ tumor cells were inocculated in saline/20% Matrigel™ into the mammary fat pad of female Balb/c nu/nu mice. Three days post transplantation mice received the following; control non-specific isotype matrched IgG4; doxorubicin Rx, 5 mg per kg i.p. once per week for two weeks; control or anti-human uPAR mAbs 0.5 mg per mouse i.p. once per week for the duration of the experiment. Tumor growth was measured once per week using calipers and tumor volumes calculated according to formula $(a \times b^2/2)$, where a—is length of the long diameter, b—width of the perpendicular small diameter (FIG. 7). Untreated control tumor growth (not shown in FIG. 7) was not significantly different compared to IgG4 isotype controls.

At the end of the study, primary tumors were fixed, and lung, liver and spleen from control and experimental animals were removed for further analysis. Tissue sections were stained for the following proteins using standard immunohistochemical techniques: Ki67; CD31; MAPK; phospho-MAPK; FAK; phospho-FAK. Staining intensity was measured using BioQuant image analysis software and data was rercorded from 6 animals per treatment group (FIG. 8).

Figure 9B:
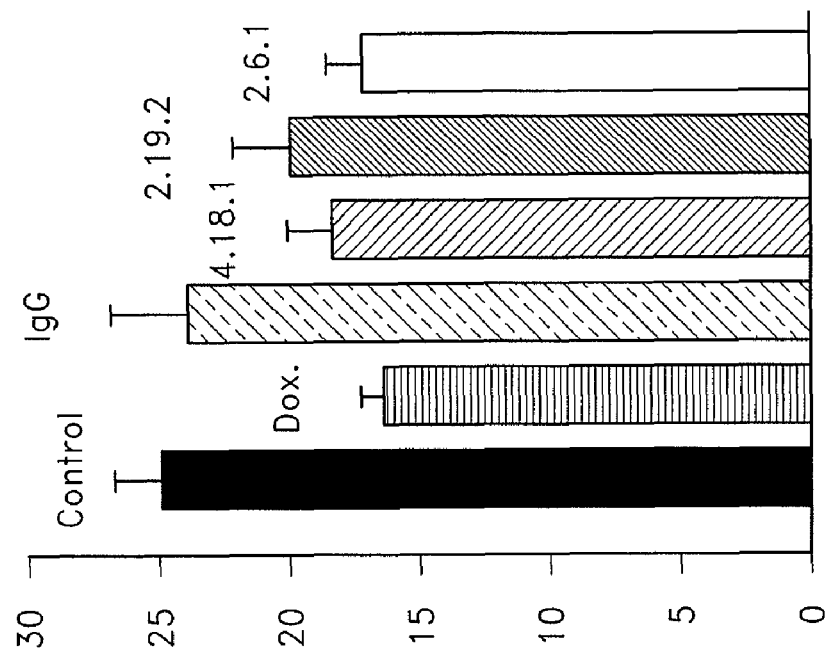
FIGS. 9A-B are bar graphs representing the activity of anti-uPAR mAbs to inhibit metastasis in mice with MDA-MB231-GFP orthotopic xenografts. The data represents the mean+/−standard deviation of the number of tumor foci in 10 fields of view in tissue sections from lung (FIG. 9A) or liver (FIG. 9B) from six animals per treatment group as indicated.
Figure 9A:
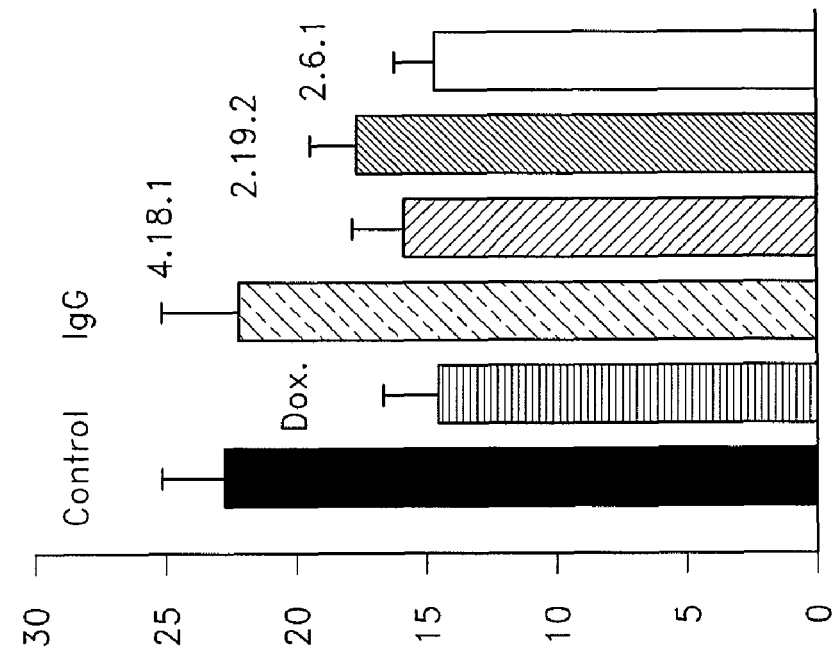

Lung, liver and spleen tissues were similarly treated and tumor cells were identified by fluorescence microscopy and the numbers of metastases were recorded (FIG. 9).

As demonstrated by FIGS. 7-9, the anti-uPAR antibodies inhibited primary tumor growth and significantly inhibited the incidence of metastases to distant organs. Immunohistochemical examination of the primary tumors showed no effect against the proliferation marker Ki67 but there was a consistent inhibition in the levels of pMAPK and pFAK compared to controls. Unexpectedly, CD31 staining also showed some reduction in staining intensity although in the absence of antibody cross reactivity with murine uPAR the mechanism must be assumed to be indirect as a result of local tumor associated uPA activity.

Example 18

Immunohistochemistry

The binding profile of 2.6.1, 2.19.2 and 4.18.1 were evaluated together with an IgG4 isotype control antibody on frozen cell pellets and normal human tissue microarrays (TriStar Technology Group). Mouse anti uPAR from American Diagnostica Inc., (Cat#: 3936, Lot#: 041223) was a positive control Ab in the study. Staining intensity was estimated by eye using a 0-3+ scale (±equivocal staining; 1+ weak staining; 2+ moderate staining; 3+ strong staining). Frozen cell pellets from PC3 human prostate cancer and U937 human histocytic lymphoma U937 cell pellets used as positive controls and both membrane and cytoplasmic staining was observed (See Table 21). Positive staining was reported only when staining was greater than and/or distinguishable from the background if the background staining was observed with the negative control antibody, or staining was in cells within the test tissue that did not stain with the negative control antibody (see Table 23 below).

TABLE 21

Staining Intenstity in Cell Pellets

| Abs | IgG4 control | 2.6.1 | 2.19.2 | 4.18.1 |
|---|---|---|---|---|
| PC-3 | — | 2+ | ± | 3+ |
| U937 | — | 2+ | 2+ | 1+ |

For staining of human tissue microarrays, 2.6.1, 2.19.2 and 4.18.1 were conjugated with Biotin, reassessed for binding to U937 cells (see Table 22 below) and then used to stain tissue microarrays.

TABLE 22

Staining Intenstity in Cell Pellets Using Biotin-Conjugated mAbs

| Abs | IgG4 control | 2.6.1 | 2.19.2 | 4.18.1 |
|---|---|---|---|---|
| U937 | — | 2+ | 2+ | 2+ |

Tissue microarrays were stained at a concentration of 20 μg per ml biotin conjugated antibody. The results are shown in Table 23. Where indicated c=cytoplasmic and m=membrane staining pattern.

TABLE 23

Tissue Microarray Staining Pattern

| Tissue Type | 2.6.1 20 ug | 2.19.2 20 ug | 4.18.1 20 ug |
|---|---|---|---|
| liver | inflammation cells 3 + (c) | inflammation cells 3 + (c) | inflammation cells 2 + (m, c) |
| liver | inflammation cells 3 + (c) | inflammation cells 3 + (c) | inflammation cells 2 + (m, c) |
| liver | inflammation cells 3 + (c) | inflammation cells 2 + (c) | inflammation cells 1 + (c) |
| liver | inflammation cells 2 + (c), stromal+ | inflammation cells 1 + (c), stromal+ | inflammation cells 1 + (c) |
| liver | inflammation cells 3 + (c) | inflammation cells 2 + (c) | inflammation cells 1 + (c) |
| liver | inflammation cells 3 + (c) | inflammation cells 2 + (c) | inflammation cells 1 + (c) |
| pancreas | acinar cells 2 + (c) | acinar cells 2 + (c) | acinar cells 1 + (c) |
| pancreas | acinar cells 3 + (c) | acinar cells 2 + (c) | acinar cells 1 + (c) |
| pancreas | acinar cells 2 + (c) | acinar cells 2 + (c) | acinar cells 1 + (c) |
| pancreas | acinar cells 1 + (c) | acinar cells 2 + (c) | acinar cells 1 + (c) |

TABLE 23-continued

Tissue Microarray Staining Pattern

| Tissue Type | 2.6.1 20 ug | 2.19.2 20 ug | 4.18.1 20 ug |
|---|---|---|---|
| pancreas | acinar cells 1 + (c) | fibroblast 1 + (c) | inflammation cells 2 + (c) |
| pancreas | acinar cells 1 + (c) | acinar cells 1 + (c) | inflammation cells 1 + (c) |
| colon mucosa | epithelium 1+ | negative | inflammation cells 2 + (c) |
| colon mucosa | epithelium 1+ | epithelium 1 + (c) | inflammation cells 2 + (m, c) |
| colon mucosa | negative | negative | negative |
| colon mucosa | epithelium 1+ | inflammation cells 1 + (c) | inflammation cells 2 + (m, c) |
| colon mucosa | epithelium 1+ | epithelium 1 + (c) | epithelium1 + (c), inflammation cells 1 + (c) |
| colon mucosa | epithelium 1+ | epithelium 1 + (c) | epithelium1 + (c), inflammation cells 1 + (c) |
| colon muscularis | negative | negative | inflammation cells 1 + (c) |
| colon muscularis | lymphocytes 1 + (c) | negative | inflammation cells 1 + (c) |
| colon muscularis | negative | inflammation cells 1 + (c) | negative |
| colon muscularis | negative | nerve 1+ | negative |
| colon muscularis | negative | inflammation cells 1 + (c) | inflammation cells 1 + (c) |
| colon muscularis | nerve 1+ | nerve 1+ | negative |
| kidney cortex | negative | negative | negative |
| kidney cortex | negative | negative | negative |
| kidney cortex | glomerulus 1 + (c) | glomerulus 1 + (c) | glomerulus 1 + (c) |
| kidney cortex | glomerulus 1 + (c) | glomerulus 1 + (c) | glomerulus 1 + (c) |
| kidney cortex | glomerulus 1 + (c) | negative | inflammation cells 1 + (c) |
| kidney cortex | glomerulus 1 + (c) | inflammation cells 1 + (c) | inflammation cells 1 + (c) |
| kidney medulla | negative | negative | negative |
| kidney medulla | negative | inflammation cells 1 + (c) | inflammation cells 1 + (c) |
| kidney medulla | negative | negative | negative |
| kidney medulla | negative | negative | negative |
| kidney medulla | negative | negative | negative |
| kidney medulla | negative | negative | inflammation cells 1 + (c) |
| lung alveoli | epithelium 2 + (m) | epithelium 2 + (m, c) | epithelium 1 + (m, c), inflammation cells 1 + (c) |
| lung alveoli | epithelium 3 + (m, c) | epithelium 3 + (m, c) | epithelium 2 + (m, c), inflammation cells 2 + (c) |
| lung alveoli | epithelium 3 + (m, c) | epithelium 3 + (m, c) | epithelium 2 + (m, c), inflammation cells 2 + (c) |
| lung bronchus | | epithelium 1 + (c) | |
| lung bronchus | negative | negative | |
| lung bronchus | epithelium 1 + (c) | epithelium 1 + (c) | inflammation cells 1 + (c) |
| lung bronchus | non-specific staining | inflammation cells 2 + (c) | inflammation cells 1 + (c) |
| lung bronchus | epithelium 1 + (c) | inflammation cells 2 + (c) | inflammation cells 1 + (c) |
| lymph node | lymphocytes 3 + (m · c) | lymphocytes 2 + (m · c) | lymphocytes 1 + (m · c) |
| lymph node | lymphocytes 3 + (m · c) | lymphocytes 3 + (m · c) | lymphocytes 1 + (m · c) |
| lymph node | lymphocytes 2 + (m · c) | lymphocytes 2 + (m · c) | lymphocytes 1 + (m · c) |
| lymph node | lymphocytes 2 + (m · c) | lymphocytes 2 + (m · c) | lymphocytes 1 + (m · c) |
| lymph node | lymphocytes 2 + (m · c) | lymphocytes 3 + (m · c) | lymphocytes 1 + (m · c) |
| heart | negative | negative | negative |
| heart | negative | negative | inflammation cells 1 + (c) |
| heart | negative | negative | inflammation cells 1 + (c) |
| heart | negative | negative | inflammation cells 1 + (c) |
| heart | negative | negative | negative |

Example 19

Inhibition of Tumor Cell Growth in Human Patients

A group of human cancer patients diagnosed with pancreatic cancer is randomized into treatment groups. Each patient group is treated with weekly intravenous injections of mAb 2.6.1, 2.19.2 or 4.18.1 described herein. Each patient is dosed with an effective amount of the antibody ranging from 5 mg/kg/week to 15 mg/kg/week for 4-8 months. A control group is given only the standard chemotherapeutic regimen.

At periodic times during and after the treatment regimen, tumor burden is assessed by magnetic resonance imaging (MRI). It is found that the patients who have received weekly antibody treatment with mAb 2.6.1, 2.19.2 or 4.18.1 show significant reductions in tumor size, time delay to progression or prolonged survival compared to patients that do not receive antibody treatment. In some treated patients, the tumors are no longer detectable. In contrast, tumor size increases or remains substantially the same in the control group.

Example 20

Inhibition of Tumor Cell Growth in a Human Patient

A group of human cancer patients diagnosed with thyroid cancer is randomized into treatment groups. Each patient group is treated 3-weekly with intravenous injections of mAb 2.6.1, 2.19.2 or 4.18.1 described herein and gemcitabine. Each patient is dosed with an effective amount of the antibody ranging from 5 mg/kg/week to 15 mg/kg/week for 4-8 months and an effective therapeutic dose of gemcitabine. A control group is given only the standard chemotherapeutic regimen. At periodic times during and after the treatment regimen, tumor burden is assessed by magnetic resonance imaging (MRI). It is found that the patients who have received 3-weekly antibody treatment with mAb 2.6.1, 2.19.2 or 4.18.1 and gemcitabine show significant reductions in tumor size, time delay to progression or prolonged survival compared to patients that do not receive antibody and gemcitabine treatment. In some treated patients, the tumors are no longer detectable. In contrast, tumor size increases or remains substantially the same in the control group.

Example 21

Inhibition of Tumor Metastasis in Human Patients

A group of human cancer patients diagnosed with non-small cell lung cancer is randomized into treatment groups. In addition to a standard chemotherapeutic regimen, each patient group is treated with weekly intravenous injections of mAb 2.6.1, 2.19.2 or 4.18.1 described herein. Each patient is dosed with an effective amount of the antibody ranging from 5 mg/kg/week to 15 mg/kg/week for 2-8 months. A control group is given only the standard chemotherapeutic regimen.

At periodic times during and after the treatment regimen, metastatic lesions are assessed by positron emission tomography (PET). It is found that the patients who have received weekly antibody treatment with mAb 2.6.1, 2.19.2 or 4.18.1 show significant reductions in the number and size of metastatic lesions, compared to patients that do not receive antibody treatment.

Example 22

Treatment of Estrogen Receptor Positive Breast Cancer in a Human Patient

An adult female is diagnosed with estrogen receptor positive breast cancer. The patient is treated every 2 weeks with intravenous injections of mAb 2.19.2 and an anti-hormonal agent over a period of 2-8 months. As a result, the patient experiences prolonged progression-free survival.

Example 23

Treatment of HER2 Positive Breast Cancer in a Human Patient

An adult female is diagnosed with HER2 positive breast cancer. The patient is treated every week with intravenous injections of mAb 2.19.2 and an anti-her2 agent over a period of 2-8 months. As a result, the patient experiences a significant reduction in tumor size.

Example 24

Treatment Of EGFR-Expressing Lung Cancer in a Human Patient

An adult male is diagnosed with EGFR-expressing lung cancer. The patient is treated weekly with intravenous injections of mAb 2.19.2 and a receptor tyrosine kinase inhibitor over a period of 2-8 months. As a result, the patient experiences a significant delay in time to progression.

Example 25

Treatment of Arthritis in a Human Patient

An adult female is diagnosed with severe arthritis. The patient is treated with intravenous injections every 2 weeks of mAb 2.19.2 over a period of 3 weeks. As a result, the patient experiences a significant reduction in the symptoms of arthritis.

Example 27

Treatment of Atherosclerosis in a Human Patient

An adult male is diagnosed with atherosclerosis. The patient is treated with intravenous injections every other week of mAb 4.18.1 over a period of a year. As a result, the patient experiences a reduction in the symptoms of atherosclerosis, such as angina pectoris.

INCORPORATION BY REFERENCE

All references cited herein, including patents, patent applications, papers, text books, and the like, and the references cited therein, to the extent that they are not already, are hereby incorporated herein by reference in their entirety.

EQUIVALENTS

The foregoing written specification is considered to be sufficient to enable one skilled in the art to practice the invention. The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

---

What is claimed is:

1. An isolated antibody, or binding fragment thereof, that specifically binds to urokinase-type plasminogen activator receptor (uPAR) and inhibits binding of urokinase-type plasminogen activator (uPA) to urokinase-type plasminogen activator receptor (uPAR), wherein said antibody is a monoclonal antibody having the amino acid sequence of the antibody produced by the hybridoma deposited at ATCC under Accession Number PTA-7475.

2. An isolated antibody, or binding fragment thereof, that specifically binds to uPAR, wherein said antibody comprises a heavy chain polypeptide comprising the sequence of SEQ ID NO.: 26 or SEQ ID NO: 26 comprising any one of the combinations of residues indicated by each row of Table 15, and a light chain polypeptide comprising the sequence of SEQ ID NO: 28, or SEQ ID NO: 28 comprising any one of the combinations of residues of SEQ ID NO: 28 indicated by each row of Table 14.

3. The antibody of claim 2, wherein said antibody comprises a heavy chain polypeptide comprising the sequence of SEQ ID NO: 26.

4. The antibody of claim 2, wherein said antibody comprises a light chain polypeptide comprising the sequence of SEQ ID NO: 28.

5. An isolated monoclonal antibody or binding fragment thereof that binds to the same epitope on uPAR as the antibody of any of claims 1 and 2-4.

6. An isolated antibody, or binding fragment thereof, that specifically binds to urokinase-type plasminogen activator receptor (uPAR), wherein the antibody comprises:
   a heavy chain complementarity determining region 1 (CDR1) having the amino acid sequence of TNYMN (SEQ ID NO: 94);
   a heavy chain complementarity determining region 2 (CDR2) having the amino acid sequence of IIYTGGSTSYADSVKG (SEQ ID NO: 95);
   a heavy chain complementarity determining region 3 (CDR3) having the amino acid sequence of EIAVAGYYGMDV (SEQ ID NO: 96);
   a light chain complementarity determining region 1 (CDR1) having the amino acid sequence of RASQGIRNDLG (SEQ ID NO: 103);
   a light chain complementarity determining region 2 (CDR2) having the amino acid sequence of AASSLQS (SEQ ID NO: 104); and
   a light chain complementarity determining region 3 (CDR3) having the amino acid sequence of LQHNSYPLT (SEQ ID NO: 105).

7. The antibody according to claim 6, wherein said antibody is a fully human monoclonal antibody.

8. A conjugate comprising the antibody of any one of claims 1, 2-4, 6 and 7 or a binding fragment thereof, and a therapeutic agent.

9. The conjugate of claim 8, wherein the therapeutic agent is a toxin.

10. The conjugate of claim 8, wherein the therapeutic agent is a radioisotope.

11. The antibody of claim 2, wherein one or more framework residues has been mutated to yield the corresponding germline residue at that position.

12. The antibody of any of claims 1, 2, 4, 6 and 7, wherein said antibody is selected from the group consisting of Fab, Fab', F(ab')2 and Fv.

13. A composition comprising the antibody of claim 1 and a pharmaceutically acceptable carrier.

14. A composition comprising the antibody of any one of claims 2, 4, and 6 and a pharmaceutically acceptable carrier.

15. A composition comprising the antibody of claim 6 and a pharmaceutically acceptable carrier.

16. A conjugate comprising the antibody of claim 5 or a binding fragment thereof, and a therapeutic agent.

17. The antibody of claim 5, wherein said antibody is selected from the group consisting of Fab, Fab', F(ab')2 and Fv.

18. A composition comprising the antibody of claim 5 and a pharmaceutically acceptable carrier.

* * * * *

SEQUENCE LISTING

```
<160> NUMBER OF SEQ ID NOS: 108

<210> SEQ ID NO 1
<211> LENGTH: 384
<212> TYPE: DNA
<213> ORGANISM: Human

<400> SEQUENCE: 1
gaggtgcagc tggtggagtc tgggggaggc ttggtacagc ctgggggtc cctgagactc      60 tcctgtgcag cctctggatt caccttcagt agctacgaca tgcactgggt ccgccaagct     120
acaggaaaag gtctggagtg ggtctcagct attggtactg ctggtgacac atactatcca    180
ggctccgtga agggccgatt caccatctcc agagaaaatg ccaagaactc cttgtatctt    240
caaatgaaca gcctgagagc cggggacacg gctgtgtatt actgtgcaag agaggggac    300
```

```
tacagtaact actttactat ggttcgggga gttacctacg gtatggacgt ctggggccaa    360
gggaccacgg tcaccgtctc ctca                                          384
```

<210> SEQ ID NO 2
<211> LENGTH: 128
<212> TYPE: PRT
<213> ORGANISM: Human

<400> SEQUENCE: 2

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Glu Gly Asp Tyr Ser Asn Tyr Phe Thr Met Val Arg Gly Val Thr
            100                 105                 110

Tyr Gly Met Asp Val Trp Gly Gln Gly Thr Thr Val Thr Val Ser Ser
        115                 120                 125
```

<210> SEQ ID NO 3
<211> LENGTH: 321
<212> TYPE: DNA
<213> ORGANISM: Human

<400> SEQUENCE: 3

```
gacatccagt tgacccagtc tccatcctca ctgtgtgcat ctgttggaga cagaatcacc     60
atcacttgtc gggcgagtca gggcattagc aaatatttag cctggtttca gcagaaacca   120
gggaaagccc ctaagtccct gatctatggt gcatccagtt tgcaaagtgg ggtcccagca   180
aagttcagcg gcagtggatc tgggacagat ttcactctca ccatcagcag cctgcagcct   240
gaagattttg caacttatta ctgccaacag tataatagtt accctctcac tttcggcgga   300
gggaccaagg tggagatcaa a                                             321
```

<210> SEQ ID NO 4
<211> LENGTH: 107
<212> TYPE: PRT
<213> ORGANISM: Human

<400> SEQUENCE: 4

```
Asp Ile Gln Leu Thr Gln Ser Pro Ser Ser Leu Cys Ala Ser Val Gly
 1               5                  10                  15

Asp Arg Ile Thr Ile Thr Cys Arg Ala Ser Gln Gly Ile Ser Lys Tyr
            20                  25                  30

Leu Ala Trp Phe Gln Gln Lys Pro Gly Lys Ala Pro Lys Ser Leu Ile
        35                  40                  45

Tyr Gly Ala Ser Ser Leu Gln Ser Gly Val Pro Ala Lys Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Tyr Asn Ser Tyr Pro Leu
                85                  90                  95
Thr Phe Gly Gly Gly Thr Lys Val Glu Ile Lys
            100                 105
```

<210> SEQ ID NO 5
<211> LENGTH: 363
<212> TYPE: DNA
<213> ORGANISM: Human

<400> SEQUENCE: 5

```
caggtgcagc tggtggagtc tgggggaggc gtggtccagc ctggggaggtc cctgagactc     60
tcctgtgcag cgcctggatt caccttcagt agctatggca tgcactgggt ccgccaggct    120
ccaggcaagg gctggagtg gtggcagtt atatggtatg atggaagtca gaaatactat      180
gcagactccg tgaagggccg attcaccatc tccagagaca attccaagaa cacgctgtat    240
ctgcaaatga acagcctgag agccgaggac acggctgtgt attactgtgc gagagggatg    300
acttactact actactacgg tatggacgtc tggggccaag gaccacggt caccgtctcc     360
tca                                                                 363
```

<210> SEQ ID NO 6
<211> LENGTH: 121
<212> TYPE: PRT
<213> ORGANISM: Human

<400> SEQUENCE: 6

```
Gln Val Gln Leu Val Glu Ser Gly Gly Gly Val Val Gln Pro Gly Arg
 1               5                  10                  15
Ser Leu Arg Leu Ser Cys Ala Ala Pro Gly Phe Thr Phe Ser Ser Tyr
            20                  25                  30
Gly Met His Trp Val Arg Gln Ala Pro Gly Lys Gly Leu Glu Trp Val
        35                  40                  45
Ala Val Ile Trp Tyr Asp Gly Ser Gln Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Gly Met Thr Tyr Tyr Tyr Tyr Tyr Gly Met Asp Val Trp Gly
            100                 105                 110
Gln Gly Thr Thr Val Thr Val Ser Ser
        115                 120
```

<210> SEQ ID NO 7
<211> LENGTH: 321
<212> TYPE: DNA
<213> ORGANISM: Human

<400> SEQUENCE: 7

```
gaaatagtga tgacgcagtc tccagccatc ctgtctgtgt ctccagggga aagagccacc     60
ctctcctgca gggccagtca gagtgttagc agcaagttag actggtacca gcagaaacct    120
ggccaggctc ccaggctcct catctatggt gcatccacca gggccactgg tatcccagcc    180
aggttcagcg gcagtgggtc cgggacagag ttcactctca ccatcagcag cctgcagtct    240
gaagattttg cagtttatta ctgtcagcag tataataact ggccgcggac gttcggccaa    300
gggaccaagg tggaaatcaa a                                              321
```

<210> SEQ ID NO 8
<211> LENGTH: 107
<212> TYPE: PRT
<213> ORGANISM: Human

<400> SEQUENCE: 8

Glu Ile Val Met Thr Gln Ser Pro Ala Ile Leu Ser Val Ser Pro Gly
1               5                   10                  15

Glu Arg Ala Thr Leu Ser Cys Arg Ala Ser Gln Ser Val Ser Ser Lys
            20                  25                  30

Leu Asp Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Arg
                85                  90                  95

Thr Phe Gly Gln Gly Thr Lys Val Glu Ile Lys
            100                 105

<210> SEQ ID NO 9
<211> LENGTH: 384
<212> TYPE: DNA
<213> ORGANISM: Human

<400> SEQUENCE: 9
gaggtgcagc tggtggagtc tgggggaggc ttggtacagc ctggggggtc cctgagactc      60
tcctgtgcag cctctggatt caccttcagt agctacgaca tgcactgggt ccgccaagct     120
acaggaaaag gtctggagtg ggtctcagct attggtactg ctggtgacac atactatcca     180
ggctccgtga agggccgatt caccatctcc agagaaaatg ccaagaactc cttgtatctt     240
caaatgaaca gcctgagagc cggggacacg gctgtgtatt actgtgcaag agaggggggac     300
tacagcaact attttactag ggttcgggga gttacctacg gtatggacgt ctggggccaa     360
gggaccacgg tcaccgtctc ctca                                             384

<210> SEQ ID NO 10
<211> LENGTH: 128
<212> TYPE: PRT
<213> ORGANISM: Human

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Pro Gly Ser Val Lys
50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Glu Gly Asp Tyr Ser Asn Tyr Phe Thr Arg Val Arg Gly Val Thr
            100                 105                 110

Tyr Gly Met Asp Val Trp Gly Gln Gly Thr Thr Val Thr Val Ser Ser
            115                 120                 125

<210> SEQ ID NO 11
<211> LENGTH: 321
<212> TYPE: DNA
<213> ORGANISM: Human

<400> SEQUENCE: 11
gacatccaga tgacccagtc tccatcctca ctgtctgcat ctgtaggaga cagagtcacc    60
atcacttgtc gggcgagtca gggcattagc aaatatttgg cctggtttca gcagaaacca   120
gggaaagccc ctaagtccct gatctatggt gcatccagtt tgcaaagtgg ggtcccatca   180
aagttcagcg gcagtggatc tgggacagat ttcactctca ccatcagcag cctgcagcct   240
gaagattttg caacttatta ctgccaacag tataatagtt accctctcac tttcggcgga   300
gggaccaagg tggagatcaa a                                              321

<210> SEQ ID NO 12
<211> LENGTH: 107
<212> TYPE: PRT
<213> ORGANISM: Human

<400> SEQUENCE: 12

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Lys Tyr
            20                  25                  30

Leu Ala Trp Phe Gln Gln Lys Pro Gly Lys Ala Pro Lys Ser Leu Ile
        35                  40                  45

Tyr Gly Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 13
<211> LENGTH: 351
<212> TYPE: DNA
<213> ORGANISM: Human

<400> SEQUENCE: 13
gaggtgcagc tggtggagtc tgaggaggc ttgatccagc cggggggtc cctgagactc       60 tcctgtgcag cctcagggtt caccgtcaga agcaactaca tgagctgggt ccgccaggct    120
ccagggaagg ggctggagtg gatctcagtt atttataccg gtggtagcac atactacgca    180
gactccgtga agggccgatt ctccatctcc agagacaatt ccaagaacac gctgtatctt    240
caaatgaaca gcctgagagc cgaggacacg gccgtgtatt actgtgcgag agagggagca    300
gtggctggat ttgactactg gggccaggga accctggtca ccgtctcctc a              351

<210> SEQ ID NO 14
<211> LENGTH: 117
<212> TYPE: PRT
<213> ORGANISM: Human

<400> SEQUENCE: 14

-continued

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Arg Ser Asn
            20                  25                  30

Tyr Met Ser Trp Val Arg Gln Ala Pro Gly Lys Gly Leu Glu Trp Ile
        35                  40                  45

Ser Val Ile Tyr Thr Gly Gly Ser Thr Tyr Tyr Ala Asp Ser Val Lys
    50                  55                  60

Gly Arg Phe Ser Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Gly Ala Val Ala Gly Phe Asp Tyr Trp Gly Gln Gly Thr Leu
            100                 105                 110

Val Thr Val Ser Ser
        115

<210> SEQ ID NO 15
<211> LENGTH: 321
<212> TYPE: DNA
<213> ORGANISM: Human

<400> SEQUENCE: 15
gaaatagtga tgacgcagtc tccagccacc ctgtctgtgt ctccagggga aagagccacc    60
ctctcctgca gggccagtca gagtattagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tatactaact ggcctctcac tttcggcgga   300
gggaccaagg tggagatcaa a                                              321

<210> SEQ ID NO 16
<211> LENGTH: 107
<212> TYPE: PRT
<213> ORGANISM: Human

<400> SEQUENCE: 16

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Thr Asn Trp Pro Leu
                85                  90                  95

Thr Phe Gly Gly Gly Thr Lys Val Glu Ile Lys
            100                 105

<210> SEQ ID NO 17
<211> LENGTH: 351
<212> TYPE: DNA
<213> ORGANISM: Human

<400> SEQUENCE: 17

```
gaggtgcagc tggtggagtc tggaggaggc ttgctccagc ctgggggtc cctgagactc       60 tcctgtgcag cctctgggtt caccgtcaga aacaattaca tgaactgggt ccgccaggct      120
ccagggaagg ggctggagtg ggtctcagtt atttataccg gtggtagcac atactacgca      180
gactccgtga agggccgctt caccatctcc agagacaatt ccaagaacac gctgtatctt      240
caaatgaaca gcctgagagc cgaggacacg gccgtgtatt actgtgcgag agaggggaag      300
cttgccggta tggacgtctg gggccaaggg accacggtca ccgtctcctc a               351
```

```
<210> SEQ ID NO 18
<211> LENGTH: 117
<212> TYPE: PRT
<213> ORGANISM: Human

<400> SEQUENCE: 18
```

Glu Val Gln Leu Val Glu Ser Gly Gly Gly Leu Leu Gln Pro Gly Gly
1               5                   10                  15

Ser Leu Arg Leu Ser Cys Ala Ala Ser Gly Phe Thr Val Arg Asn Asn
            20                  25                  30

Tyr Met Asn Trp Val Arg Gln Ala Pro Gly Lys Gly Leu Glu Trp Val
        35                  40                  45

Ser Val Ile Tyr Thr Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Gly Lys Leu Ala Gly Met Asp Val Trp Gly Gln Gly Thr Thr
            100                 105                 110

Val Thr Val Ser Ser
        115

```
<210> SEQ ID NO 19
<211> LENGTH: 321
<212> TYPE: DNA
<213> ORGANISM: Human

<400> SEQUENCE: 19
```

```
gaaacagtga tgacgcagtc tccagccacc ctgtctgtgt ctccagggga aagagccacc       60
ctctcctgca gggccagtca gagtgttagc agcaacttag cctggtacca gcagaaacct      120
ggccaggctc ccaggctcct catctatggt gcatccacca gggccactgg tatcccagcc      180
aggttcagtg gcagtgggtc tgggacagag ttcactctca ccatcagcag cctgcagtct      240
gaagaatttg cagtttatta ctgtcagcag tataataact ggccgctcac tttcggcgga      300
gggaccaagg tggagatcaa a                                                 321
```

```
<210> SEQ ID NO 20
<211> LENGTH: 107
<212> TYPE: PRT
<213> ORGANISM: Human

<400> SEQUENCE: 20
```

Glu Thr Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile

```
                      35                  40                  45
Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Glu Phe Ala Val Tyr Tyr Cys Gln Gln Tyr Asn Asn Trp Pro Leu
                 85                  90                  95

Thr Phe Gly Gly Gly Thr Lys Val Glu Ile Lys
            100                 105

<210> SEQ ID NO 21
<211> LENGTH: 366
<212> TYPE: DNA
<213> ORGANISM: Human

<400> SEQUENCE: 21
caggtgcagc tggtggagtc tgggggaggc gtggtccagc ctggggaggtc cctgagactc       60 tcctgtgcag cgtctggatt caccttcagt agctatggca tgcactgggt ccgccaggct      120
ccaggcaagg ggctggagtg ggtggcagtt atatggtatg atggaagtaa taaatactat      180
gcagactccg tgaagggccg attcaccatc tccagagaca attccaagaa cacgctgtat      240
ctgcaaatga acagcctgag agccgaggac acggctgtgt attactgtgc gagagatcta      300
gcagctctct actactacta cggtatgcac gtctggggcc aagggaccac ggtcaccgtc      360
tcctca                                                                 366

<210> SEQ ID NO 22
<211> LENGTH: 122
<212> TYPE: PRT
<213> ORGANISM: Human

<400> SEQUENCE: 22

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Ala Ala Leu Tyr Tyr Tyr Tyr Gly Met His Val Trp
            100                 105                 110

Gly Gln Gly Thr Thr Val Thr Val Ser Ser
            115                 120

<210> SEQ ID NO 23
<211> LENGTH: 321
<212> TYPE: DNA
<213> ORGANISM: Human

<400> SEQUENCE: 23
gaaatagtga tgacgcagtc tccagccacc ctgtctgtgt ctccagggga aagagccacc       60
ctctcctgca gggccagtca gagttttagc agcaacttag cctggtacca gcagaaacct      120
```

```
ggccaggctc ccaggctcct catctatggt gcatccacca gggccactgg tatcccagcc      180
aggttcagtg gcagtgggtc tgggacagag ttcactctca ccatcagcag cctgcagtct      240
gaagattttg cagtttatta ctgtcagcag aataataact ggcctcggac gttcggccaa      300
gggaccaagg tggaaatcaa a                                                321
```

<210> SEQ ID NO 24
<211> LENGTH: 107
<212> TYPE: PRT
<213> ORGANISM: Human

<400> SEQUENCE: 24

```
Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Phe Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Asn Asn Asn Trp Pro Arg
                85                  90                  95

Thr Phe Gly Gln Gly Thr Lys Val Glu Ile Lys
            100                 105
```

<210> SEQ ID NO 25
<211> LENGTH: 359
<212> TYPE: DNA
<213> ORGANISM: Human

<400> SEQUENCE: 25

```
gaggtgcagc tggtggagtc tggaggaggc ttgatccagc ctgggggtc cctgagactc        60 tcctgtgcag cctctgggtt caccgtcatt accaactaca tgaactgggt ccgccaggct      120
ccaggaaagg gctggagtg gtctcaatt atttataccg gtggtagcac atcctacgca       180
gactccgtga agggccgatt caccgtctcc agagacaatt ccaagaacac gctgtatctt      240
cacatgaaca gcctgagagt cgaggacacg gccgtgtatt actgtgcgag agagatagca      300
gtggctggct actacggtat ggacgtctgg ggccaaggga ccacggtcac cgtctcctc      359
```

<210> SEQ ID NO 26
<211> LENGTH: 119
<212> TYPE: PRT
<213> ORGANISM: Human

<400> SEQUENCE: 26

```
Glu Val Gln Leu Val Glu Ser Gly Gly Gly Leu Ile Gln Pro Gly Gly
 1               5                  10                  15

Ser Leu Arg Leu Ser Cys Ala Ala Ser Gly Phe Thr Val Ile Thr Asn
            20                  25                  30

Tyr Met Asn Trp Val Arg Gln Ala Pro Gly Lys Gly Leu Glu Trp Val
        35                  40                  45

Ser Ile Ile Tyr Thr Gly Gly Ser Thr Ser Tyr Ala Asp Ser Val Lys
    50                  55                  60

Gly Arg Phe Thr Val Ser Arg Asp Asn Ser Lys Asn Thr Leu Tyr Leu
65                  70                  75                  80
```

```
His Met Asn Ser Leu Arg Val Glu Asp Thr Ala Val Tyr Tyr Cys Ala
                85                  90                  95

Arg Glu Ile Ala Val Ala Gly Tyr Tyr Gly Met Asp Val Trp Gly Gln
            100                 105                 110

Gly Thr Thr Val Thr Val Ser
        115

<210> SEQ ID NO 27
<211> LENGTH: 321
<212> TYPE: DNA
<213> ORGANISM: Human

<400> SEQUENCE: 27
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatagtt acccgctcac tttcggcgga   300
gggaccaggg tggagatcaa a                                             321

<210> SEQ ID NO 28
<211> LENGTH: 107
<212> TYPE: PRT
<213> ORGANISM: Human

<400> SEQUENCE: 28

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
 65                 70                  75                  80

Glu Asp Phe Ala Thr Tyr Tyr Cys Leu Gln His Asn Ser Tyr Pro Leu
                85                  90                  95

Thr Phe Gly Gly Gly Thr Arg Val Glu Ile Lys
            100                 105

<210> SEQ ID NO 29
<211> LENGTH: 365
<212> TYPE: DNA
<213> ORGANISM: Human

<400> SEQUENCE: 29
caggtgcagc tggtggagtc tgggggaggc gtggtccagc ctggagggtc cctgagactc    60
tcctgtgcag cgtctggatt caccttcagt agctatggca tgcactgggt ccgccaggct   120
ccaggcaagg ggctggagtg ggtggcagtt atatggtatg atggaagtaa taatactat    180 gcagactccg tgaagggccg attcaccatc tccagagaca attccaagaa cacgctgtat   240
ctgcaaatga acagcctgag agccgaggac acggctgtgt attactgtgc gagagatcag   300
catattgtgg tggtgactgc tattcttgac tactggggcc agggaaccct ggtcaccgtc   360
tcctc                                                               365
```

<210> SEQ ID NO 30
<211> LENGTH: 122
<212> TYPE: PRT
<213> ORGANISM: Human

<400> SEQUENCE: 30

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln His Ile Val Val Thr Ala Ile Leu Asp Tyr Trp
            100                 105                 110

Gly Gln Gly Thr Leu Val Thr Val Ser Ser
        115                 120

<210> SEQ ID NO 31
<211> LENGTH: 341
<212> TYPE: DNA
<213> ORGANISM: Human

<400> SEQUENCE: 31
gacatcgtga tgacccagtc tccagactcc ctgtctgtgt ctctgggcga gagggccacc      60
atcaactgca gtccagcca gagtgtttta tatggctcca acaataggaa ctccttggct     120
tggtaccagc agaaaccagg acagcctccc aagctgctca tttactgggc atctacccgg    180
gaatccgggg tccctgaccg attcagtggc agcgggtctg ggacagattt cactctcacc    240
atcagcagcc tgcaggctga agatgtggca gtttattact gtcagcaata ttatagtatt    300
tttccgtgga cgttcggcca agggaccaag gtggaaatca a                        341

<210> SEQ ID NO 32
<211> LENGTH: 114
<212> TYPE: PRT
<213> ORGANISM: Human

<400> SEQUENCE: 32

Asp Ile Val Met Thr Gln Ser Pro Asp Ser Leu Ser Val Ser Leu Gly
1               5                   10                  15

Glu Arg Ala Thr Ile Asn Cys Lys Ser Ser Gln Ser Val Leu Tyr Gly
            20                  25                  30

Ser Asn Asn Arg Asn Ser Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ile Phe Pro Trp Thr Phe Gly Gln Gly Thr Lys Val Glu
            100                 105                 110

Ile Lys

<210> SEQ ID NO 33
<211> LENGTH: 377
<212> TYPE: DNA
<213> ORGANISM: Human

<400> SEQUENCE: 33

```
gaggtgcagc tggtggagtc tgggggaggc ttggtccagc ctggggggtc cctgagactc      60
tcctgtgcag cctctggatt cacttttagt agctattgga tgagctgggt ccgccaggct     120
ccagggaagg gctggagtg gtggccaac ataaagcaac atggaagtga aaatactat        180
gtggactctg tgaagggccg attcaccatc tccagagaca acgccaagaa ctcactgtat     240
ctgcaaatga acagcctgag agccgaggac acggctgtgt attactgtgc gagagaggag    300
gcttattatt atgataatag tggttactac tggtacttcg atctctgggc tcgtggcacc    360
ctggtcactg tctcctc                                                    377
```

<210> SEQ ID NO 34
<211> LENGTH: 126
<212> TYPE: PRT
<213> ORGANISM: Human

<400> SEQUENCE: 34

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Trp Met Ser Trp Val Arg Gln Ala Pro Gly Lys Gly Leu Glu Trp Val
         35                  40                  45

Ala Asn Ile Lys Gln His Gly Ser Glu Lys Tyr Tyr Val Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Glu Ala Tyr Tyr Tyr Asp Asn Ser Gly Tyr Tyr Trp Tyr
            100                 105                 110

Phe Asp Leu Trp Ala Arg Gly Thr Leu Val Thr Val Ser Ser
        115                 120                 125
```

<210> SEQ ID NO 35
<211> LENGTH: 322
<212> TYPE: DNA
<213> ORGANISM: Human

<400> SEQUENCE: 35

```
gacatccaga tgacccagtc tccatcttcc gtgtctgcat ctataggaga cagagtcacc      60
atcacttgtc gggcgagtca gggtattagc agctggttag cctggtatca gcagaaacca    120
gggaaaaccc ctaagctcct gatctatgct gcatccagtt tacaaagtgg ggtcccatca    180
aggttcagcg gcagtggatc tgggacagat ttcactctca ccatcagcag cctgcagcct    240
gaagattttg caacttacta ttgtcaacag gctgacagtt cccgtggac gttcggccaa    300
gggaccaagg tggaaatcaa ac                                              322
```

<210> SEQ ID NO 36
<211> LENGTH: 107

```
<212> TYPE: PRT
<213> ORGANISM: Human

<400> SEQUENCE: 36

Asp Ile Gln Met Thr Gln Ser Pro Ser Ser Val Ser Ala Ser Ile Gly
 1               5                  10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Thr Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asp Ser Phe Pro Trp
                85                  90                  95

Thr Phe Gly Gln Gly Thr Lys Val Glu Ile Lys
            100                 105

<210> SEQ ID NO 37
<211> LENGTH: 372
<212> TYPE: DNA
<213> ORGANISM: Human

<400> SEQUENCE: 37
caggtgcagc tgcaggagtc gggcccagga ctggtgaagc cttcacagac cctgtccctc     60
acctgcactg tctctggtgg ctccatcagc agtggtggtc actactggag ctggatccgc    120
cagcacccag ggaagggcct ggagtggatt gggtacatct attacagtgg agaaacctac    180
tacaacccgt ccctcaagag tcgagttacc atatcagtag acacgtctaa gaaccagttc    240
tccctgaagc tgagctctgt gactgccgcg gacacggccg tgtattactg tgcgagagat    300
ggggggactg ggattactac tactacggt atggacgtct ggggccaagg gaccacggtc    360
accgtctcct ca                                                       372

<210> SEQ ID NO 38
<211> LENGTH: 123
<212> TYPE: PRT
<213> ORGANISM: Human

<400> SEQUENCE: 38

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
            20                  25                  30

Gly His Tyr Trp Ser Trp Ile Arg Gln His Pro Gly Lys Gly Leu Glu
        35                  40                  45

Trp Ile Gly Tyr Ile Tyr Tyr Ser Gly Arg Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Thr Gly Asp Tyr Tyr Tyr Gly Met Asp Val
            100                 105                 110

Trp Gly Gln Gly Thr Thr Val Thr Val Ser Ser
        115                 120
```

<210> SEQ ID NO 39
<211> LENGTH: 338
<212> TYPE: DNA
<213> ORGANISM: Human

<400> SEQUENCE: 39

| | | | | | |
|---|---|---|---|---|---|
| gacatcgtga tgacccagtc tccaacctcc ctgactgtgt ctctgggcga gagggccacc | | | | | 60 |
| atcaactgca agtccagcca gagtgtttta tacagctcca acaataggaa cttcttagct | | | | | 120 |
| tggtaccagc agaaaccaag acagcctcct aagctgctca tttactgggc atctacccgg | | | | | 180 |
| gaatccgggg tccctgaccg attcagtggc agcgggtctg ggacagattt cactctcacc | | | | | 240 |
| atcagcagcc tgcaggctga agatgtggca gtttattact gtcagcaata ttatactact | | | | | 300 |
| ccgctcactt tcggcggagg gaccaaggtg gagatcaa | | | | | 338 |

<210> SEQ ID NO 40
<211> LENGTH: 113
<212> TYPE: PRT
<213> ORGANISM: Human

<400> SEQUENCE: 40

Asp Ile Val Met Thr Gln Ser Pro Thr Ser Leu Thr Val Ser Leu Gly
 1               5                  10                  15

Glu Arg Ala Thr Ile Asn Cys Lys Ser Ser Gln Ser Val Leu Tyr Ser
             20                  25                  30

Ser Asn Asn Arg Asn Phe Leu Ala Trp Tyr Gln Gln Lys Pro Arg Gln
         35                  40                  45

Pro Pro Lys Leu Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Thr Thr Pro Leu Thr Phe Gly Gly Gly Thr Lys Val Glu Ile
            100                 105                 110

Lys

<210> SEQ ID NO 41
<211> LENGTH: 369
<212> TYPE: DNA
<213> ORGANISM: Human

<400> SEQUENCE: 41

| | | | | | |
|---|---|---|---|---|---|
| gaggtgcagc tggtggagtc tgggggaggc ttggtccagc ctggggggtc cctgagactc | | | | | 60 |
| tcctgtgcag cctctggatt cacctttagt agctattgga tgagctgggt ccgccaggct | | | | | 120 |
| ccagggacgg ggctggattg ggtggccaac ataaaccaag atggaagtga gatactat | | | | | 180 |
| gtggactctg tgaagggccg attcaccatc tccagagaca acgccaagaa ctcaccgcat | | | | | 240 |
| ctgcaaatga acagcctgag agccgaggac acggctgttt attactgtgc gagagggga | | | | | 300 |
| agcggtggca ggtacggagg ctggtacttc gatctctggg gccgtggcac cctggtcact | | | | | 360 |
| gtctcctca | | | | | 369 |

<210> SEQ ID NO 42
<211> LENGTH: 123
<212> TYPE: PRT
<213> ORGANISM: Human

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Thr Gly Leu Asp Trp Val
        35                  40                  45

Ala Asn Ile Asn Gln Asp Gly Ser Glu Arg Tyr Tyr Val Asp Ser Val
    50                  55                  60

Lys Gly Arg Phe Thr Ile Ser Arg Asp Asn Ala Lys Asn Ser Pro His
65                  70                  75                  80

Leu Gln Met Asn Ser Leu Arg Ala Glu Asp Thr Ala Val Tyr Tyr Cys
                85                  90                  95

Ala Arg Glu Gly Ser Gly Gly Arg Tyr Gly Gly Trp Tyr Phe Asp Leu
            100                 105                 110

Trp Gly Arg Gly Thr Leu Val Thr Val Ser Ser
            115                 120

<210> SEQ ID NO 43
<211> LENGTH: 342
<212> TYPE: DNA
<213> ORGANISM: Human

<400> SEQUENCE: 43
gacatcgtga tgacccagtc tccagactcc ctggctgtgt ctctgggcga gagggccacc      60
atcaactgca gtccagcca gagtgtttta tacagttcca acaataagaa cttcttagct     120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagtc tgcaggctga agatgtggca gtttattact gtcagcaata ttatagtact     300
cctccgatca ccttcggcca agggacacga ctggagatta aa                         342

<210> SEQ ID NO 44
<211> LENGTH: 114
<212> TYPE: PRT
<213> ORGANISM: Human

<400> SEQUENCE: 44

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Phe Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Pro Ile Thr Phe Gly Gln Gly Thr Arg Leu Glu
            100                 105                 110

Ile Lys

<210> SEQ ID NO 45
<211> LENGTH: 366
<212> TYPE: DNA

<213> ORGANISM: Human

<400> SEQUENCE: 45

```
gaggtgcagt tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtcttaggt attagtggta gtggtggtag cacatactac     180
gcagactccg tgaagggccg gttcaccatc tccagagaca attccaagaa cacgctgtat     240
ctgcaaatga acagcctgag agccgaggac acggccgtat attactgtgc gaaagatggc     300
tacggtgact acgtaggctg gtatttcgat ctctggggcc gtggcaccct ggtcactgtc     360
tcctca                                                                366
```

<210> SEQ ID NO 46
<211> LENGTH: 122
<212> TYPE: PRT
<213> ORGANISM: Human

<400> SEQUENCE: 46

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Leu Gly Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Gly Tyr Gly Asp Tyr Val Gly Trp Tyr Phe Asp Leu Trp
            100                 105                 110

Gly Arg Gly Thr Leu Val Thr Val Ser Ser
        115                 120
```

<210> SEQ ID NO 47
<211> LENGTH: 339
<212> TYPE: DNA
<213> ORGANISM: Human

<400> SEQUENCE: 47

```
gacatcgtga tgacccagtc tccagactcc ctggctgtgt ctctgggcga gagggccacc      60
atcaactgca gtccagcca gagtgtttta tacagctcca acaataagaa cttcttagct     120
tggtaccagc agaaaccagg acagcctcct aagctactca tttactgggc atctacccgg     180
gaatccgggg tccctgaccg attcagtggc agcgggtctg ggacagattt cactctcacc     240
atcagcaacc tgcaggctga agatgtggca gtttattact gtcaacaatt ttatagtact     300
cctccgacgt tcggccaagg gaccaaggtg gagatcaga                            339
```

<210> SEQ ID NO 48
<211> LENGTH: 113
<212> TYPE: PRT
<213> ORGANISM: Human

<400> SEQUENCE: 48

```
Asp Ile Val Met Thr Gln Ser Pro Asp Ser Leu Ala Val Ser Leu Gly
 1               5                   10                  15
```

```
Glu Arg Ala Thr Ile Asn Cys Lys Ser Ser Gln Ser Val Leu Tyr Ser
            20                  25                  30

Ser Asn Asn Lys Asn Phe Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Asn Leu Gln Ala Glu Asp Val Ala Val Tyr Tyr Cys Gln Gln
                85                  90                  95

Phe Tyr Ser Thr Pro Pro Thr Phe Gly Gln Gly Thr Lys Val Glu Ile
                100                 105                 110

Arg

<210> SEQ ID NO 49
<211> LENGTH: 351
<212> TYPE: DNA
<213> ORGANISM: Human

<400> SEQUENCE: 49
gaggtgcagc tggtggagtc tggaggaggc ttgatccagc ctgggggtc cctgagactc         60 tcctgtgcag cctctgggtt caccgtcagg aataactaca tgaactgggt ccgccaggct       120
ccagggaagg gctggagtg gtctcagtt atttataccg gtggtagcac atactacgca        180
gactccgtga aggccgatt caccatctcc agagacaatt ccaggaacac gctgtatctt       240
caaatgaaca gcctgagagc cgaggacacg gccgtgtatt actgtgcgag agaaggggca       300
gtggctggtt ttgactactg gggccaggga accctggtca ccgtctcttt a               351

<210> SEQ ID NO 50
<211> LENGTH: 117
<212> TYPE: PRT
<213> ORGANISM: Human

<400> SEQUENCE: 50

Glu Val Gln Leu Val Glu Ser Gly Gly Gly Leu Ile Gln Pro Gly Gly
 1               5                  10                  15

Ser Leu Arg Leu Ser Cys Ala Ala Ser Gly Phe Thr Val Arg Asn Asn
            20                  25                  30

Tyr Met Asn Trp Val Arg Gln Ala Pro Gly Lys Gly Leu Glu Trp Val
        35                  40                  45

Ser Val Ile Tyr Thr Gly Gly Ser Thr Tyr Tyr Ala Asp Ser Val Lys
 50                  55                  60

Gly Arg Phe Thr Ile Ser Arg Asp Asn Ser Arg Asn Thr Leu Tyr Leu
 65                  70                  75                  80

Gln Met Asn Ser Leu Arg Ala Glu Asp Thr Ala Val Tyr Tyr Cys Ala
                85                  90                  95

Arg Glu Gly Ala Val Ala Gly Phe Asp Tyr Trp Gly Gln Gly Thr Leu
                100                 105                 110

Val Thr Val Ser Leu
        115

<210> SEQ ID NO 51
<211> LENGTH: 321
<212> TYPE: DNA
<213> ORGANISM: Human

<400> SEQUENCE: 51
```

```
gaaatagtga tgacgcagtt tccagccacc ctgtctatgt ctccagggga aagagccacc    60
ctctcctgca gggccagtca gagtgttagc agcagcttag cctggtacca gcagacacct   120
ggccaggctc ccaggctcct catctatggt gcatccacca ggtccactgg tttcccagcc   180
aggttcagtg gcattgggtc tgggacagag ttcactctca ccatcagcag ccttcagtct   240
gaagattttg cagtttatta ctgtcagcag tatggtaact ggcctctcac cttcggccaa   300
gggacacgac tggagattaa a                                             321
```

\<210\> SEQ ID NO 52
\<211\> LENGTH: 107
\<212\> TYPE: PRT
\<213\> ORGANISM: Human

\<400\> SEQUENCE: 52

```
Glu Ile Val Met Thr Gln Phe Pro Ala Thr Leu Ser Met Ser Pro Gly
 1               5                  10                  15

Glu Arg Ala Thr Leu Ser Cys Arg Ala Ser Gln Ser Val Ser Ser
             20                  25                  30

Leu Ala Trp Tyr Gln Gln Thr Pro Gly Gln Ala Pro Arg Leu Leu Ile
         35                  40                  45

Tyr Gly Ala Ser Thr Arg Ser Thr Gly Phe Pro Ala Arg Phe Ser Gly
 50                  55                  60

Ile Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Gly Asn Trp Pro Leu
                 85                  90                  95

Thr Phe Gly Gln Gly Thr Arg Leu Glu Ile Lys
            100                 105
```

\<210\> SEQ ID NO 53
\<211\> LENGTH: 351
\<212\> TYPE: DNA
\<213\> ORGANISM: Human

\<400\> SEQUENCE: 53

```
gaggtgcagc tggtggagtc tggaggaggc ttgatccagc ctgggggtc cctgagactc     60 tcctgtgcag cctctgggtt ctccgtcagt agcaactaca tgaactgggt ccgccaggct   120
ccagggaagg gctggagtg gtctcagtt atttataccg gtggtagcac atactacgca    180
gactccgtga agggccgatt caccatctcc agagacaatt ccaagaacac cctgtatctt   240
caaatgaaca gcctgagagc cgaggacacg gccgtatatt actgtgcgag agatacttac   300
ctctacggta tggacgtctg gggccaaggg accacggtca ccgtctcctc a            351
```

\<210\> SEQ ID NO 54
\<211\> LENGTH: 117
\<212\> TYPE: PRT
\<213\> ORGANISM: Human

\<400\> SEQUENCE: 54

```
Glu Val Gln Leu Val Glu Ser Gly Gly Gly Leu Ile Gln Pro Gly Gly
 1               5                  10                  15

Ser Leu Arg Leu Ser Cys Ala Ala Ser Gly Phe Ser Val Ser Ser Asn
             20                  25                  30

Tyr Met Asn Trp Val Arg Gln Ala Pro Gly Lys Gly Leu Glu Trp Val
         35                  40                  45

Ser Val Ile Tyr Thr Gly Gly Ser Thr Tyr Tyr Ala Asp Ser Val Lys
```

```
            50                  55                  60
Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Asp Thr Tyr Leu Tyr Gly Met Asp Val Trp Gly Gln Gly Thr Thr
            100                 105                 110

Val Thr Val Ser Ser
            115

<210> SEQ ID NO 55
<211> LENGTH: 321
<212> TYPE: DNA
<213> ORGANISM: Human

<400> SEQUENCE: 55
gaaatagtga tgacgcagtc tccagccacc ctgtctgtgt ctccagggga aagcgccacc      60
ctctcctgca ggaccagtca gagtgttagc agcaacttag cctggtacca gcagaaacct    120
ggccagactc ccaggctcct catctatggt gcatccgcca gggccactgg tgtcccagcc    180
aggttcagtg gcagtgggtc tgggacagag ttcactctca ccatcagcag cctgcagtct    240
gaagattttg cagtttatta ctgtcagcag tattataact ggcctctcac tttcggcgga    300
gggaccaagg tggagatcaa a                                              321

<210> SEQ ID NO 56
<211> LENGTH: 107
<212> TYPE: PRT
<213> ORGANISM: Human

<400> SEQUENCE: 56

Glu Ile Val Met Thr Gln Ser Pro Ala Thr Leu Ser Val Ser Pro Gly
  1               5                  10                  15

Glu Ser Ala Thr Leu Ser Cys Arg Thr Ser Gln Ser Val Ser Ser Asn
                 20                  25                  30

Leu Ala Trp Tyr Gln Gln Lys Pro Gly Gln Thr Pro Arg Leu Leu Ile
             35                  40                  45

Tyr Gly Ala Ser Ala Arg Ala Thr Gly Val Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Tyr Asn Trp Pro Leu
                 85                  90                  95

Thr Phe Gly Gly Gly Thr Lys Val Glu Ile Lys
            100                 105

<210> SEQ ID NO 57
<211> LENGTH: 366
<212> TYPE: DNA
<213> ORGANISM: Human

<400> SEQUENCE: 57
caggtgcagc tggtggagtc tgggggaggc gtggtccagc ctgggaggtc cctgagactc      60
tcctgtgcag cgtctggatt caccttcagt agctatggca tgcactgggt ccgccaggct    120
ccaggcaagg ggctggagtg ggtggcagtt atatggtatg atggaagtaa taaagactat    180
gcagactccg tgaagggccg attcaccatc tccagagaca attccaagaa cacgctgtat    240
ctgcaaatga acagcctgag agccgaggac acggctgtgt attactgtgc gagagatatg    300
```

```
atagtagtgg ttattactta tgcttttgat atctggggcc aagggacaat ggtcaccgtc    360
tcttca                                                               366
```

```
<210> SEQ ID NO 58
<211> LENGTH: 122
<212> TYPE: PRT
<213> ORGANISM: Human

<400> SEQUENCE: 58
```

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Met Ile Val Val Val Ile Thr Tyr Ala Phe Asp Ile Trp
            100                 105                 110

Gly Gln Gly Thr Met Val Thr Val Ser Ser
        115                 120

```
<210> SEQ ID NO 59
<211> LENGTH: 339
<212> TYPE: DNA
<213> ORGANISM: Human

<400> SEQUENCE: 59
gacatcgtga tgacccagtc tccagactcc ctggctgtgt ctctgggcga gagggccacc    60
atcaactgca gtccagcca gagtgtttta tacagctcca acaataagaa ctacttagct    120
tggtaccagc agaaatcagg acagcctcct aagctgctca tttactgggc atctacccgg    180
gaatccgggg tccctgaccg attcagtggc agcgggtctg ggacagattt cactctcacc    240
atcagcagcc tgcaggctga agatgtggca gtttactact gtcagcaata ttataggact    300
cctccgacgt tcggccaagg gaccagggtg gaaatcaaa                           339
```

```
<210> SEQ ID NO 60
<211> LENGTH: 113
<212> TYPE: PRT
<213> ORGANISM: Human

<400> SEQUENCE: 60
```

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Ser Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

-continued

```
Ile Ser Ser Leu Gln Ala Glu Asp Val Ala Val Tyr Tyr Cys Gln Gln
                85                  90                  95

Tyr Tyr Arg Thr Pro Pro Thr Phe Gly Gln Gly Thr Arg Val Glu Ile
            100                 105                 110

Lys

<210> SEQ ID NO 61
<211> LENGTH: 113
<212> TYPE: PRT
<213> ORGANISM: Human

<400> SEQUENCE: 61

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Pro Thr Phe Gly Gln Gly Thr Lys Val Glu Ile
            100                 105                 110

Lys

<210> SEQ ID NO 62
<211> LENGTH: 114
<212> TYPE: PRT
<213> ORGANISM: Human

<400> SEQUENCE: 62

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Pro Ile Thr Phe Gly Gln Gly Thr Arg Leu Glu
            100                 105                 110

Ile Lys

<210> SEQ ID NO 63
<211> LENGTH: 107
<212> TYPE: PRT
<213> ORGANISM: Human

<400> SEQUENCE: 63

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
                100                 105

<210> SEQ ID NO 64
<211> LENGTH: 107
<212> TYPE: PRT
<213> ORGANISM: Human

<400> SEQUENCE: 64

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Arg
                85                  90                  95

Thr Phe Gly Gln Gly Thr Lys Val Glu Ile Lys
                100                 105

<210> SEQ ID NO 65
<211> LENGTH: 107
<212> TYPE: PRT
<213> ORGANISM: Human

<400> SEQUENCE: 65

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys
                100                 105

<210> SEQ ID NO 66
<211> LENGTH: 107
```

```
<212> TYPE: PRT
<213> ORGANISM: Human

<400> SEQUENCE: 66

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Leu
                85                  90                  95

Thr Phe Gly Gln Gly Thr Arg Leu Glu Ile Lys
            100                 105

<210> SEQ ID NO 67
<211> LENGTH: 105
<212> TYPE: PRT
<213> ORGANISM: Human

<400> SEQUENCE: 67

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Thr Phe
                85                  90                  95

Gly Gly Gly Thr Lys Val Glu Ile Lys
            100                 105

<210> SEQ ID NO 68
<211> LENGTH: 111
<212> TYPE: PRT
<213> ORGANISM: Human

<400> SEQUENCE: 68

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95
```

```
Tyr Tyr Ser Thr Thr Phe Gly Gly Gly Thr Lys Val Glu Ile Lys
                100                 105                 110

<210> SEQ ID NO 69
<211> LENGTH: 107
<212> TYPE: PRT
<213> ORGANISM: Human

<400> SEQUENCE: 69

Asp Ile Gln Met Thr Gln Ser Pro Ser Ser Val Ser Ala Ser Val Gly
  1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Trp
                 85                  90                  95

Thr Phe Gly Gln Gly Thr Lys Val Glu Ile Lys
                100                 105

<210> SEQ ID NO 70
<211> LENGTH: 124
<212> TYPE: PRT
<213> ORGANISM: Human

<400> SEQUENCE: 70

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Asp Met His Trp Val Arg Gln Ala Thr Gly Lys Gly Leu Glu Trp Val
         35                  40                  45

Ser Ala Ile Gly Thr Ala Gly Asp Thr Tyr Tyr Pro Gly Ser Val Lys
     50                  55                  60

Gly Arg Phe Thr Ile Ser Arg Glu Asn Ala Lys Asn Ser Leu Tyr Leu
 65                  70                  75                  80

Gln Met Asn Ser Leu Arg Ala Asp Thr Ala Val Tyr Tyr Cys Ala
                 85                  90                  95

Arg Asp Tyr Ser Asn Tyr Thr Met Val Arg Gly Val Tyr Gly Met Asp
                100                 105                 110

Val Trp Gly Gln Gly Thr Thr Val Thr Val Ser Ser
            115                 120

<210> SEQ ID NO 71
<211> LENGTH: 118
<212> TYPE: PRT
<213> ORGANISM: Human

<400> SEQUENCE: 71

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
```

-continued

```
                35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Tyr Gly Asp Tyr Trp Tyr Phe Asp Leu Trp Gly Arg Gly Thr
                100                 105                 110

Leu Val Thr Val Ser Ser
        115

<210> SEQ ID NO 72
<211> LENGTH: 121
<212> TYPE: PRT
<213> ORGANISM: Human

<400> SEQUENCE: 72

Gln Val Gln Leu Val Glu Ser Gly Gly Gly Val Val Gln Pro Gly Arg
 1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
                35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Met Ile Val Val Val Ile Thr Ala Phe Asp Ile Trp Gly
                100                 105                 110

Gln Gly Thr Met Val Thr Val Ser Ser
        115                 120

<210> SEQ ID NO 73
<211> LENGTH: 118
<212> TYPE: PRT
<213> ORGANISM: Human

<400> SEQUENCE: 73

Gln Val Gln Leu Val Glu Ser Gly Gly Gly Val Val Gln Pro Gly Arg
 1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
                35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Tyr Tyr Tyr Tyr Gly Met Asp Val Trp Gly Gln Gly Thr
                100                 105                 110

Thr Val Thr Val Ser Ser
        115
```

<210> SEQ ID NO 74
<211> LENGTH: 114
<212> TYPE: PRT
<213> ORGANISM: Human

<400> SEQUENCE: 74

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Val Ala Phe Asp Tyr Trp Gly Gln Gly Thr Leu Val Thr Val
            100                 105                 110

Ser Ser

<210> SEQ ID NO 75
<211> LENGTH: 112
<212> TYPE: PRT
<213> ORGANISM: Human

<400> SEQUENCE: 75

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Met Asp Val Trp Gly Gln Gly Thr Thr Val Thr Val Ser Ser
            100                 105                 110

<210> SEQ ID NO 76
<211> LENGTH: 117
<212> TYPE: PRT
<213> ORGANISM: Human

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Trp Tyr Trp Tyr Phe Asp Leu Trp Gly Arg Gly Thr Leu
            100                 105                 110

Val Thr Val Ser Ser
            115
```

<210> SEQ ID NO 77
<211> LENGTH: 120
<212> TYPE: PRT
<213> ORGANISM: Human

<400> SEQUENCE: 77

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg His Ile Val Val Thr Ala Ile Leu Asp Tyr Trp Gly Gln
            100                 105                 110

Gly Thr Leu Val Thr Val Ser Ser
             115                 120
```

<210> SEQ ID NO 78
<211> LENGTH: 118
<212> TYPE: PRT
<213> ORGANISM: Human

<400> SEQUENCE: 78

```
Glu Val Gln Leu Val Glu Ser Gly Gly Gly Leu Ile Gln Pro Gly Gly
 1               5                  10                  15

Ser Leu Arg Leu Ser Cys Ala Ala Ser Gly Phe Thr Val Ser Ser Asn
                 20                  25                  30

Tyr Met Ser Trp Val Arg Gln Ala Pro Gly Lys Gly Leu Glu Trp Val
             35                  40                  45

Ser Val Ile Tyr Ser Gly Gly Ser Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Ile Ala Val Ala Gly Tyr Tyr Gly Met Asp Val Trp Gly Gln Gly
            100                 105                 110

Thr Thr Val Thr Val Ser
             115
```

<210> SEQ ID NO 79
<211> LENGTH: 123

<212> TYPE: PRT
<213> ORGANISM: Human

<400> SEQUENCE: 79

Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Ser Ser Tyr
             20                  25                  30
Trp Met Ser Trp Val Arg Gln Ala Pro Gly Lys Gly Leu Glu Trp Val
         35                  40                  45
Ala Asn Ile Lys Gln Asp Gly Ser Glu Lys Tyr Tyr Val Asp Ser Val
     50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                 85                  90                  95
Ala Arg Tyr Tyr Tyr Asp Ser Ser Gly Tyr Tyr Trp Tyr Phe Asp Leu
            100                 105                 110
Trp Gly Arg Gly Thr Leu Val Thr Val Ser Ser
        115                 120

<210> SEQ ID NO 80
<211> LENGTH: 119
<212> TYPE: PRT
<213> ORGANISM: Human

<400> SEQUENCE: 80

Gln Val Gln Leu Gln Glu Ser Gly Pro Gly Leu Val Lys Pro Ser Gln
 1               5                  10                  15
Thr Leu Ser Leu Thr Cys Thr Val Ser Gly Gly Ser Ile Ser Ser Gly
             20                  25                  30
Gly Tyr Tyr Trp Ser Trp Ile Arg Gln His Pro Gly Lys Gly Leu Glu
         35                  40                  45
Trp Ile Gly Tyr Ile Tyr Tyr Ser Gly Ser Thr Tyr Tyr Asn Pro Ser
     50                  55                  60
Leu Lys Ser Arg Val Thr Ile Ser Val Asp Thr Ser Lys Asn Gln Phe
65                  70                  75                  80
Ser Leu Lys Leu Ser Ser Val Thr Ala Ala Asp Thr Ala Val Tyr Tyr
                 85                  90                  95
Cys Ala Arg Thr Tyr Tyr Tyr Tyr Gly Met Asp Val Trp Gly Gln Gly
            100                 105                 110
Thr Thr Val Thr Val Ser Ser
        115

<210> SEQ ID NO 81
<211> LENGTH: 990
<212> TYPE: DNA
<213> ORGANISM: Cynomolgus

<400> SEQUENCE: 81
atgggtcacc cgctgctgct gccactgctg ctgctgctcc acacctgcgt cccagcctct    60
tggggcctgc ggtgcatgca gtgtaagagc aacgggggatt gccgggtgga agagtgcgcc   120
ctaggacagg acctctgcag gaccacgatc gtgcgcatgt gggaagaagg ggaagagctg   180
gagctggtgg agaaaagctg tacccactca gagaagacca caggaccat gagctatcgg   240 actggcttga agatcaccag ccttaccgag gttgtgtgtg gttagactt gtgcaaccag   300 ggcaactctg gccgggctgt cacctttttcc cgaagccgtt accttgaatg catttcctgt   360

```
ggctcatcag acatgagctg tgagaggggc cggcaccaga gcctgcaatg ccgcagccct      420
gaagaacagt gcctggacgt ggtgacccac tggatccagg agggtgaaga agggcgtcca      480
aaggatgacc gccacctccg aggctgtggc taccttccca gctgcccagg ctccagtggt      540
ttccacaaca cgacaccttt ccacttcctg aagtgttgca acaccaccaa atgcaacgag      600
ggcccaatcc tggagcttga aaatctgcca cagaatggcc accagtgtta cagctgcaag      660
gggaacagca cccatggatg ctcctctgaa gagactttcc tcattgactg ccgaggcccc      720
atgaatcaat gtctggtagc caccggcact tacgaaccga aaaccaaag ctatatggta       780 agaggctgtg taactgcctc aatgtgccaa cgtgcccacc tgggtgacgc cttcagcatg      840
caccacatca atgtctcctg ctgtactgaa agtggctgta accacccaga cctggatatc      900
cagtaccgcg ctcgaggagg gcccgaacaa aaactcatct cagaagagga tctgaatagc      960
gccgtcgacc atcatcatca tcatcattga                                       990
```

<210> SEQ ID NO 82
<211> LENGTH: 329
<212> TYPE: PRT
<213> ORGANISM: Cynomolgus

<400> SEQUENCE: 82

```
Met Gly His Pro Leu Leu Pro Leu Leu Leu Leu His Thr Cys
 1               5                  10                  15

Val Pro Ala Ser Trp Gly Leu Arg Cys Met Gln Cys Lys Ser Asn Gly
                20                  25                  30

Asp Cys Arg Val Glu Glu Cys Ala Leu Gly Gln Asp Leu Cys Arg Thr
            35                  40                  45

Thr Ile Val Arg Met Trp Glu Glu Gly Glu Glu Leu Glu Leu Val Glu
        50                  55                  60

Lys Ser Cys Thr His Ser Glu Lys Thr Asn Arg Thr Met Ser Tyr Arg
65                  70                  75                  80

Thr Gly Leu Lys Ile Thr Ser Leu Thr Glu Val Val Cys Gly Leu Asp
                85                  90                  95

Leu Cys Asn Gln Gly Asn Ser Gly Arg Ala Val Thr Phe Ser Arg Ser
            100                 105                 110

Arg Tyr Leu Glu Cys Ile Ser Cys Gly Ser Ser Asp Met Ser Cys Glu
        115                 120                 125

Arg Gly Arg His Gln Ser Leu Gln Cys Arg Ser Pro Glu Glu Gln Cys
    130                 135                 140

Leu Asp Val Val Thr His Trp Ile Gln Glu Gly Glu Glu Gly Arg Pro
145                 150                 155                 160

Lys Asp Asp Arg His Leu Arg Gly Cys Gly Tyr Leu Pro Ser Cys Pro
                165                 170                 175

Gly Ser Ser Gly Phe His Asn Asn Asp Thr Phe His Phe Leu Lys Cys
            180                 185                 190

Cys Asn Thr Thr Lys Cys Asn Glu Gly Pro Ile Leu Glu Leu Glu Asn
        195                 200                 205

Leu Pro Gln Asn Gly His Gln Cys Tyr Ser Cys Lys Gly Asn Ser Thr
    210                 215                 220

His Gly Cys Ser Ser Glu Glu Thr Phe Leu Ile Asp Cys Arg Gly Pro
225                 230                 235                 240

Met Asn Gln Cys Leu Val Ala Thr Gly Thr Tyr Glu Pro Lys Asn Gln
                245                 250                 255

Ser Tyr Met Val Arg Gly Cys Val Thr Ala Ser Met Cys Gln Arg Ala
```

```
              260                 265                 270
His Leu Gly Asp Ala Phe Ser Met His His Ile Asn Val Ser Cys Cys
            275                 280                 285

Thr Glu Ser Gly Cys Asn His Pro Asp Leu Asp Ile Gln Tyr Arg Ala
            290                 295                 300

Arg Gly Gly Pro Glu Gln Lys Leu Ile Ser Glu Glu Asp Leu Asn Ser
305                 310                 315                 320

Ala Val Asp His His His His His His
                325
```

<210> SEQ ID NO 83
<211> LENGTH: 996
<212> TYPE: DNA
<213> ORGANISM: Chimera

<400> SEQUENCE: 83

```
atgggactcc caaggcggct gctgctgctg ctgttgctgg cgactacctg tgtcccagcc      60
tcccagggcc tgcagtgcat gcagtgtgag agtaaccaga gctgcctggt agaggagtgt     120
gctctgggcc aggacctctg caggactacc gtgcttcggg aatggcaaga tgatagagag     180
ctggaggtgg tgacaagagg ctgtgcccac agcgaaaaga ccaacaggac catgagttac     240
cgcatgggct ccatgatcat cagcctgaca gagaccgtgt gcgccacaaa cctctgcaac     300
aggcccagac ccggagcccg aggccgtgct ttccctcagg ccgttacct cgagtgtatt      360
tcctgtggct catcagacat gagctgtgag aggggccggc accagagcct gcagtgccgc     420
agccctgaag aacagtgcct ggatgtggtg acccactgga tccaggaagg tgaagaaggg     480
cgtccaaagg atgaccgcca cctccgtggc tgtggctacc ttcccggctg cccgggctcc     540
aatggttttc caacaacga caccttccac ttcctgaaat gctgcaacac caccaaatgc      600
aacgagggcc caatcctgga gcttgaaaat ctgccgcaga tggccgcca gtgttacagc      660
tgcaagggga cagcaccca tggatgctcc tctgaagaga ctttcctcat tgactgccga      720
ggccccatga tcaatgtctc ggtagccacc ggcactcacg aaccgaaaaa ccaaagctat     780
atggtaagag gctgtgcaac cgcctcaatg tgccaacatg cccacctggg tgacgccttc     840
agcatgaacc acattgatgt ctcctgctgt actaaaagtg gctgtaacca cccagacctg     900
gatatccagt accgcgctca aggagggccc gaacaaaaac tcatctcaga agaggatctg     960
aatagcgccg tcgaccatca tcatcatcat cattga                               996
```

<210> SEQ ID NO 84
<211> LENGTH: 331
<212> TYPE: PRT
<213> ORGANISM: Chimera

<400> SEQUENCE: 84

```
Met Gly Leu Pro Arg Arg Leu Leu Leu Leu Leu Leu Ala Thr Thr
  1                 5                  10                  15

Cys Val Pro Ala Ser Gln Gly Leu Gln Cys Met Gln Cys Glu Ser Asn
             20                  25                  30

Gln Ser Cys Leu Val Glu Glu Cys Ala Leu Gly Gln Asp Leu Cys Arg
         35                  40                  45

Thr Thr Val Leu Arg Glu Trp Gln Asp Asp Arg Glu Leu Glu Val Val
     50                  55                  60

Thr Arg Gly Cys Ala His Ser Glu Lys Thr Asn Arg Thr Met Ser Tyr
 65                  70                  75                  80

Arg Met Gly Ser Met Ile Ile Ser Leu Thr Glu Thr Val Cys Ala Thr
```

|  |  |  |  | 85 |  |  |  | 90 |  |  |  | 95 |  |
|---|---|---|---|---|---|---|---|---|---|---|---|---|---|
Asn | Leu | Cys | Asn | Arg | Pro | Arg | Pro | Gly | Ala | Arg | Gly | Arg | Ala | Phe | Pro
| | | | 100 | | | | | 105 | | | | | 110

Gln Gly Arg Tyr Leu Glu Cys Ile Ser Cys Gly Ser Ser Asp Met Ser
          115                    120                  125

Cys Glu Arg Gly Arg His Gln Ser Leu Gln Cys Arg Ser Pro Glu Glu
    130                    135                    140

Gln Cys Leu Asp Val Val Thr His Trp Ile Gln Glu Gly Glu Gly
145                  150                    155                  160

Arg Pro Lys Asp Arg His Leu Arg Gly Cys Gly Tyr Leu Pro Gly
              165                    170                  175

Cys Pro Gly Ser Asn Gly Phe His Asn Asn Asp Thr Phe His Phe Leu
          180                    185                  190

Lys Cys Cys Asn Thr Thr Lys Cys Asn Glu Gly Pro Ile Leu Glu Leu
          195                    200                  205

Glu Asn Leu Pro Gln Asn Gly Arg Gln Cys Tyr Ser Cys Lys Gly Asn
          210                    215                  220

Ser Thr His Gly Cys Ser Ser Glu Glu Thr Phe Leu Ile Asp Cys Arg
225                  230                    235                  240

Gly Pro Met Asn Gln Cys Leu Val Ala Thr Gly Thr His Glu Pro Lys
              245                    250                  255

Asn Gln Ser Tyr Met Val Arg Gly Cys Ala Thr Ala Ser Met Cys Gln
          260                    265                  270

His Ala His Leu Gly Asp Ala Phe Ser Met Asn His Ile Asp Val Ser
              275                    280                  285

Cys Cys Thr Lys Ser Gly Cys Asn His Pro Asp Leu Asp Ile Gln Tyr
    290                    295                    300

Arg Ala Gln Gly Gly Pro Glu Gln Lys Leu Ile Ser Glu Glu Asp Leu
305                  310                    315                  320

Asn Ser Ala Val Asp His His His His His
              325                    330

<210> SEQ ID NO 85
<211> LENGTH: 972
<212> TYPE: DNA
<213> ORGANISM: Chimera

<400> SEQUENCE: 85

| | | | | | |
|---|---|---|---|---|---|
| atgggtcacc cgctgctgct gccgctgctg ctgctgctcc acacctgcgt cccagcctct | 60 |
| tggggcctgc ggtgcatgca gtgtaagacc aacggggatt gccgtgtgga agagtgcgcc | 120 |
| ctggacaggg acctctgcag gaccacgatc gtgcgcttgt gggaagaagg agaagagctg | 180 |
| gagctggtgg agaaaagctg tacccactca gagaagacca caggaccct gagctatcgg | 240 |
| actggcttga agatcaccag ccttaccgag gttgtgtgtg gttagactt gtgcaaccag | 300 |
| ggcaactctg gccgggctgt cacctattcc cgaagccgtt acctcgaatg catttcctgt | 360 |
| ggctcatcag acatgagctg tgagagggc cggcaccaga gcctgcagtg ccgcagccct | 420 |
| gaagaacagt gcctggatgt ggtgacccac tggatccagg aaggtgaaga agggcgtcca | 480 |
| aaggatgacc gccacctccg tggctgtggc taccttcccg gctgcccggg ctccaatggt | 540 |
| ttccacaaca acgacacctt ccacttcctg aaatgctgca caccaccaa atgcaacgag | 600 |
| ggcccaatcc tggagcttga aaatctgccg cagaatggcc gccagtgtta cagctgtgag | 660 |
| gggaacaata cccttgggtg ttcctccgaa gaggcgtctc tcatcaactg ccggggacca | 720 |
| atgaatcagt gcctggtggc tacaggctta gatgtgctgg gaaaccggag ttataccgta | 780 |

```
agaggctgcg ccacggcttc ctggtgccaa ggctcccacg tggcagactc cttcccgacc    840
cacctcaacg tctctgtctc ctgctgccac ggcagcggct gtaacagccc cacacgagga    900
gggcccgaac aaaaactcat ctcagaagag gatctgaata gcgccgtcga ccatcatcat    960
catcatcatt ga                                                        972
```

<210> SEQ ID NO 86
<211> LENGTH: 323
<212> TYPE: PRT
<213> ORGANISM: Chimera

<400> SEQUENCE: 86

```
Met Gly His Pro Leu Leu Pro Leu Leu Leu Leu His Thr Cys
 1               5                  10                  15

Val Pro Ala Ser Trp Gly Leu Arg Cys Met Gln Cys Lys Thr Asn Gly
            20                  25                  30

Asp Cys Arg Val Glu Glu Cys Ala Leu Gly Gln Asp Leu Cys Arg Thr
        35                  40                  45

Thr Ile Val Arg Leu Trp Glu Glu Gly Glu Glu Leu Glu Leu Val Glu
    50                  55                  60

Lys Ser Cys Thr His Ser Glu Lys Thr Asn Arg Thr Leu Ser Tyr Arg
65                  70                  75                  80

Thr Gly Leu Lys Ile Thr Ser Leu Thr Glu Val Val Cys Gly Leu Asp
                85                  90                  95

Leu Cys Asn Gln Gly Asn Ser Gly Arg Ala Val Thr Tyr Ser Arg Ser
            100                 105                 110

Arg Tyr Leu Glu Cys Ile Ser Cys Gly Ser Ser Asp Met Ser Cys Glu
        115                 120                 125

Arg Gly Arg His Gln Ser Leu Gln Cys Arg Ser Pro Glu Glu Gln Cys
    130                 135                 140

Leu Asp Val Val Thr His Trp Ile Gln Glu Gly Glu Glu Gly Arg Pro
145                 150                 155                 160

Lys Asp Asp Arg His Leu Arg Gly Cys Gly Tyr Leu Pro Gly Cys Pro
                165                 170                 175

Gly Ser Asn Gly Phe His Asn Asn Asp Thr Phe His Phe Leu Lys Cys
            180                 185                 190

Cys Asn Thr Thr Lys Cys Asn Glu Gly Pro Ile Leu Glu Leu Glu Asn
        195                 200                 205

Leu Pro Gln Asn Gly Arg Gln Cys Tyr Ser Cys Glu Gly Asn Asn Thr
    210                 215                 220

Leu Gly Cys Ser Ser Glu Glu Ala Ser Leu Ile Asn Cys Arg Gly Pro
225                 230                 235                 240

Met Asn Gln Cys Leu Val Ala Thr Gly Leu Asp Val Leu Gly Asn Arg
                245                 250                 255

Ser Tyr Thr Val Arg Gly Cys Ala Thr Ala Ser Trp Cys Gln Gly Ser
            260                 265                 270

His Val Ala Asp Ser Phe Pro Thr His Leu Asn Val Ser Val Ser Cys
        275                 280                 285

Cys His Gly Ser Gly Cys Asn Ser Pro Thr Arg Gly Gly Pro Glu Gln
    290                 295                 300

Lys Leu Ile Ser Glu Glu Asp Leu Asn Ser Ala Val Asp His His His
305                 310                 315                 320

His His His
```

<210> SEQ ID NO 87
<211> LENGTH: 978
<212> TYPE: DNA
<213> ORGANISM: Chimera

<400> SEQUENCE: 87

| | | | | | |
|---|---|---|---|---|---|
| atgggactcc | caaggcggct | gctgctgctg | ctgttgctgg | cgactacctg | tgtcccagcc | 60 |
| tcccagggcc | tgcagtgcat | gcagtgtgag | agtaaccaga | gctgcctggt | agaggagtgt | 120 |
| gctctgggcc | aggacctctg | caggactacc | gtgcttcggg | aatggcaaga | tgatagagag | 180 |
| ctggaggtgg | tgacaagagg | ctgtgcccac | agcgaaaaga | ccaacaggac | catgagttac | 240 |
| cgcatgggct | ccatgatcat | cagcctgaca | gagaccgtgt | gcgccacaaa | cctctgcaac | 300 |
| aggcccagac | ccggagcccg | aggccgtgct | ttccctcagg | gccgttacct | cgagtgtatt | 360 |
| tcctgtggct | catcagacat | gagctgtgag | aggggccggc | accagagcct | gcagtgccgc | 420 |
| agccctgaag | aacagtgcct | ggatgtggtg | acccactgga | tccaggaagg | tgaagaaggg | 480 |
| cgtccaaagg | atgaccgcca | cctccgtggc | tgtggctacc | ttcccggctg | cccgggctcc | 540 |
| aatggtttcc | acaacaacga | caccttccac | ttcctgaaat | gctgcaacac | caccaaatgc | 600 |
| aacgagggcc | aatcctgga | gcttgaaaat | ctgccgcaga | atggccgcca | gtgttacagc | 660 |
| tgtgagggga | caatacccct | tgggtgttcc | tccgaagagg | cgtctctcat | caactgccgg | 720 |
| ggaccaatga | atcagtgcct | ggtggctaca | ggcttagatg | tgctgggaaa | ccggagttat | 780 |
| accgtaagag | gctgcgccac | ggcttcctgg | tgccaaggct | cccacgtggc | agactccttc | 840 |
| ccgacccacc | tcaacgtctc | tgtctcctgc | tgccacggca | gcggctgtaa | cagccccaca | 900 |
| cgaggagggc | ccgaacaaaa | actcatctca | gaagaggatc | tgaatagcgc | cgtcgaccat | 960 |
| catcatcatc | atcattga | | | | | 978 |

<210> SEQ ID NO 88
<211> LENGTH: 325
<212> TYPE: PRT
<213> ORGANISM: Chimera

<400> SEQUENCE: 88

| Met | Gly | Leu | Pro | Arg | Leu | Leu | Leu | Leu | Leu | Leu | Leu | Ala | Thr | Thr |
|---|---|---|---|---|---|---|---|---|---|---|---|---|---|---|
| 1 | | | | 5 | | | | | 10 | | | | | 15 |

| Cys | Val | Pro | Ala | Ser | Gln | Gly | Leu | Gln | Cys | Met | Gln | Cys | Glu | Ser | Asn |
|---|---|---|---|---|---|---|---|---|---|---|---|---|---|---|---|
| | | | 20 | | | | | 25 | | | | | 30 | | |

Gln Ser Cys Leu Val Glu Glu Cys Ala Leu Gly Gln Asp Leu Cys Arg
         35                  40                  45

Thr Thr Val Leu Arg Glu Trp Gln Asp Asp Arg Glu Leu Glu Val Val
 50                  55                  60

Thr Arg Gly Cys Ala His Ser Glu Lys Thr Asn Arg Thr Met Ser Tyr
 65                  70                  75                  80

Arg Met Gly Ser Met Ile Ile Ser Leu Thr Glu Thr Val Cys Ala Thr
                 85                  90                  95

Asn Leu Cys Asn Arg Pro Arg Pro Gly Ala Arg Gly Arg Ala Phe Pro
             100                 105                 110

Gln Gly Arg Tyr Leu Glu Cys Ile Ser Cys Gly Ser Ser Asp Met Ser
         115                 120                 125

Cys Glu Arg Gly Arg His Gln Ser Leu Gln Cys Arg Ser Pro Glu Glu
     130                 135                 140

Gln Cys Leu Asp Val Val Thr His Trp Ile Gln Glu Gly Glu Glu Gly
145                 150                 155                 160

Arg Pro Lys Asp Asp Arg His Leu Arg Gly Cys Gly Tyr Leu Pro Gly

```
                    165                 170                 175
Cys Pro Gly Ser Asn Gly Phe His Asn Asp Thr Phe His Phe Leu
        180                 185                 190

Lys Cys Cys Asn Thr Thr Lys Cys Asn Glu Gly Pro Ile Leu Glu Leu
            195                 200                 205

Glu Asn Leu Pro Gln Asn Gly Arg Gln Cys Tyr Ser Cys Glu Gly Asn
        210                 215                 220

Asn Thr Leu Gly Cys Ser Ser Glu Glu Ala Ser Leu Ile Asn Cys Arg
225                 230                 235                 240

Gly Pro Met Asn Gln Cys Leu Val Ala Thr Gly Leu Asp Val Leu Gly
            245                 250                 255

Asn Arg Ser Tyr Thr Val Arg Gly Cys Ala Thr Ala Ser Trp Cys Gln
        260                 265                 270

Gly Ser His Val Ala Asp Ser Phe Pro Thr His Leu Asn Val Ser Val
            275                 280                 285

Ser Cys Cys His Gly Ser Gly Cys Asn Ser Pro Thr Arg Gly Gly Pro
        290                 295                 300

Glu Gln Lys Leu Ile Ser Glu Glu Asp Leu Asn Ser Ala Val Asp His
305                 310                 315                 320

His His His His
            325

<210> SEQ ID NO 89
<211> LENGTH: 987
<212> TYPE: DNA
<213> ORGANISM: Chimera

<400> SEQUENCE: 89
atgggactcc caaggcggct gctgctgctg ctgttgctgg cgactacctg tgtcccagcc      60
tcccagggcc tgcagtgcat gcagtgtgag agtaaccaga gctgcctggt agaggagtgt     120
gctctgggcc aggacctctg caggactacc gtgcttcggg aatggcaaga tgatagagag     180
ctggaggtgg tgacaagagg ctgtgcccac agcgaaaaga ccaacaggac catgagttac     240
cgcatgggct ccatgatcat cagcctgaca gagaccgtgt gcgccacaaa cctctgcaac     300
aggcccagac ccggagcccg aggccgtgct ttccctcagg ccgttacctc gagtgtgcg     360 tcctgcacct ctttggacca gagctgtgag aggggccggg agcaaagcct gcaatgccgc     420
tatcctacag agcactgtat tgaagtggtg accctccaga gcacagaaag gagcttgaag     480
gatgaggact acacccgagg ctgtggcagt cttcccggat gcccaggcac agcaggtttc     540
catagcaacc agaccttca cttcctgaag tgttgcaact acacccactg caatggtggc     600
ccagttctgg atcttcagag cttcaccg aatggcttcc agtgttacag ctgcaagggg     660
aacagcaccc atggatgctc ctctgaagag actttcctca ttgactgccg aggccccatg     720
aatcaatgtc tggtagccac cggcactcac gaaccgaaaa accaaagcta tatggtaaga     780
ggctgtgcaa ccgcctcaat gtgccaacat gcccacctgg tgacgccttc agcatgaac     840 cacattgatg tctcctgctg tactaaaagt ggctgtaacc acccagacct ggatatccag     900
taccgcgctc taggagggcc cgaacaaaaa ctcatctcag aagaggatct gaatagcgcc     960
gtcgaccatc atcatcatca tcattga                                         987

<210> SEQ ID NO 90
<211> LENGTH: 328
<212> TYPE: PRT
<213> ORGANISM: Chimera
```

```
<400> SEQUENCE: 90

Met Gly Leu Pro Arg Arg Leu Leu Leu Leu Leu Leu Ala Thr Thr
  1               5                  10                  15

Cys Val Pro Ala Ser Gln Gly Leu Gln Cys Met Gln Cys Glu Ser Asn
             20                  25                  30

Gln Ser Cys Leu Val Glu Glu Cys Ala Leu Gly Gln Asp Leu Cys Arg
         35                  40                  45

Thr Thr Val Leu Arg Glu Trp Gln Asp Asp Arg Glu Leu Glu Val Val
 50                  55                  60

Thr Arg Gly Cys Ala His Ser Glu Lys Thr Asn Arg Thr Met Ser Tyr
 65                  70                  75                  80

Arg Met Gly Ser Met Ile Ile Ser Leu Thr Glu Thr Val Cys Ala Thr
                 85                  90                  95

Asn Leu Cys Asn Arg Pro Arg Pro Gly Ala Arg Gly Arg Ala Phe Pro
            100                 105                 110

Gln Gly Arg Tyr Leu Glu Cys Ala Ser Cys Thr Ser Leu Asp Gln Ser
            115                 120                 125

Cys Glu Arg Gly Arg Glu Gln Ser Leu Gln Cys Arg Tyr Pro Thr Glu
130                 135                 140

His Cys Ile Glu Val Val Thr Leu Gln Ser Thr Glu Arg Ser Leu Lys
145                 150                 155                 160

Asp Glu Asp Tyr Thr Arg Gly Cys Gly Ser Leu Pro Gly Cys Pro Gly
                165                 170                 175

Thr Ala Gly Phe His Ser Asn Gln Thr Phe His Phe Leu Lys Cys Cys
            180                 185                 190

Asn Tyr Thr His Cys Asn Gly Gly Pro Val Leu Asp Leu Gln Ser Phe
        195                 200                 205

Pro Pro Asn Gly Phe Gln Cys Tyr Ser Cys Lys Gly Asn Ser Thr His
210                 215                 220

Gly Cys Ser Ser Glu Glu Thr Phe Leu Ile Asp Cys Arg Gly Pro Met
225                 230                 235                 240

Asn Gln Cys Leu Val Ala Thr Gly Thr His Glu Pro Lys Asn Gln Ser
                245                 250                 255

Tyr Met Val Arg Gly Cys Ala Thr Ala Ser Met Cys Gln His Ala His
            260                 265                 270

Leu Gly Asp Ala Phe Ser Met Asn His Ile Asp Val Ser Cys Cys Thr
        275                 280                 285

Lys Ser Gly Cys Asn His Pro Asp Leu Asp Ile Gln Tyr Arg Ala Leu
290                 295                 300

Gly Gly Pro Glu Gln Lys Leu Ile Ser Glu Glu Asp Leu Asn Ser Ala
305                 310                 315                 320

Val Asp His His His His His His
                325

<210> SEQ ID NO 91
<211> LENGTH: 5
<212> TYPE: PRT
<213> ORGANISM: Homo sapiens

<400> SEQUENCE: 91

Ser Tyr Gly Met His
  1               5

<210> SEQ ID NO 92
<211> LENGTH: 17
<212> TYPE: PRT
```

<213> ORGANISM: Homo sapiens

<400> SEQUENCE: 92

Val Ile Trp Tyr Asp Gly Ser Asn Lys Tyr Tyr Ala Asp Ser Val Lys
1               5                   10                  15
Gly

<210> SEQ ID NO 93
<211> LENGTH: 13
<212> TYPE: PRT
<213> ORGANISM: Homo sapiens

<400> SEQUENCE: 93

Asp Gln His Ile Val Val Val Thr Ala Ile Leu Asp Tyr
1               5                   10

<210> SEQ ID NO 94
<211> LENGTH: 5
<212> TYPE: PRT
<213> ORGANISM: Homo sapiens

<400> SEQUENCE: 94

Thr Asn Tyr Met Asn
1               5

<210> SEQ ID NO 95
<211> LENGTH: 16
<212> TYPE: PRT
<213> ORGANISM: Homo sapiens

<400> SEQUENCE: 95

Ile Ile Tyr Thr Gly Gly Ser Thr Ser Tyr Ala Asp Ser Val Lys Gly
1               5                   10                  15

<210> SEQ ID NO 96
<211> LENGTH: 12
<212> TYPE: PRT
<213> ORGANISM: Homo sapiens

<400> SEQUENCE: 96

Glu Ile Ala Val Ala Gly Tyr Tyr Gly Met Asp Val
1               5                   10

<210> SEQ ID NO 97
<211> LENGTH: 5
<212> TYPE: PRT
<213> ORGANISM: Homo sapiens

<400> SEQUENCE: 97

Asn Asn Tyr Met Asn
1               5

<210> SEQ ID NO 98
<211> LENGTH: 16
<212> TYPE: PRT
<213> ORGANISM: Homo sapiens

<400> SEQUENCE: 98

Val Ile Tyr Thr Gly Gly Ser Thr Tyr Tyr Ala Asp Ser Val Lys Gly
1               5                   10                  15

<210> SEQ ID NO 99
<211> LENGTH: 9
<212> TYPE: PRT

```
<400> SEQUENCE: 99

Glu Gly Ala Val Ala Gly Phe Asp Tyr
1               5

<210> SEQ ID NO 100
<211> LENGTH: 17
<212> TYPE: PRT
<213> ORGANISM: Homo sapiens

<400> SEQUENCE: 100

Lys Ser Ser Gln Ser Val Leu Tyr Gly Ser Asn Asn Arg Asn Ser Leu
1               5                   10                  15

Ala

<210> SEQ ID NO 101
<211> LENGTH: 7
<212> TYPE: PRT
<213> ORGANISM: Homo sapiens

<400> SEQUENCE: 101

Trp Ala Ser Thr Arg Glu Ser
1               5

<210> SEQ ID NO 102
<211> LENGTH: 10
<212> TYPE: PRT
<213> ORGANISM: Homo sapiens

<400> SEQUENCE: 102

Gln Gln Tyr Tyr Ser Ile Phe Pro Trp Thr
1               5                   10

<210> SEQ ID NO 103
<211> LENGTH: 11
<212> TYPE: PRT
<213> ORGANISM: Homo sapiens

<400> SEQUENCE: 103

Arg Ala Ser Gln Gly Ile Arg Asn Asp Leu Gly
1               5                   10

<210> SEQ ID NO 104
<211> LENGTH: 7
<212> TYPE: PRT
<213> ORGANISM: Homo sapiens

<400> SEQUENCE: 104

Ala Ala Ser Ser Leu Gln Ser
1               5

<210> SEQ ID NO 105
<211> LENGTH: 9
<212> TYPE: PRT
<213> ORGANISM: Homo sapiens

<400> SEQUENCE: 105

Leu Gln His Asn Ser Tyr Pro Leu Thr
1               5

<210> SEQ ID NO 106
<211> LENGTH: 11
<212> TYPE: PRT
<213> ORGANISM: Homo sapiens
```

-continued

```
<400> SEQUENCE: 106

Arg Ala Ser Gln Ser Val Ser Ser Ser Leu Ala
1               5                   10

<210> SEQ ID NO 107
<211> LENGTH: 7
<212> TYPE: PRT
<213> ORGANISM: Homo sapiens

<400> SEQUENCE: 107

Gly Ala Ser Thr Arg Ser Thr
1               5

<210> SEQ ID NO 108
<211> LENGTH: 9
<212> TYPE: PRT
<213> ORGANISM: Homo sapiens

<400> SEQUENCE: 108

Gln Gln Tyr Gly Asn Trp Pro Leu Thr
1               5
```